Figure 3:
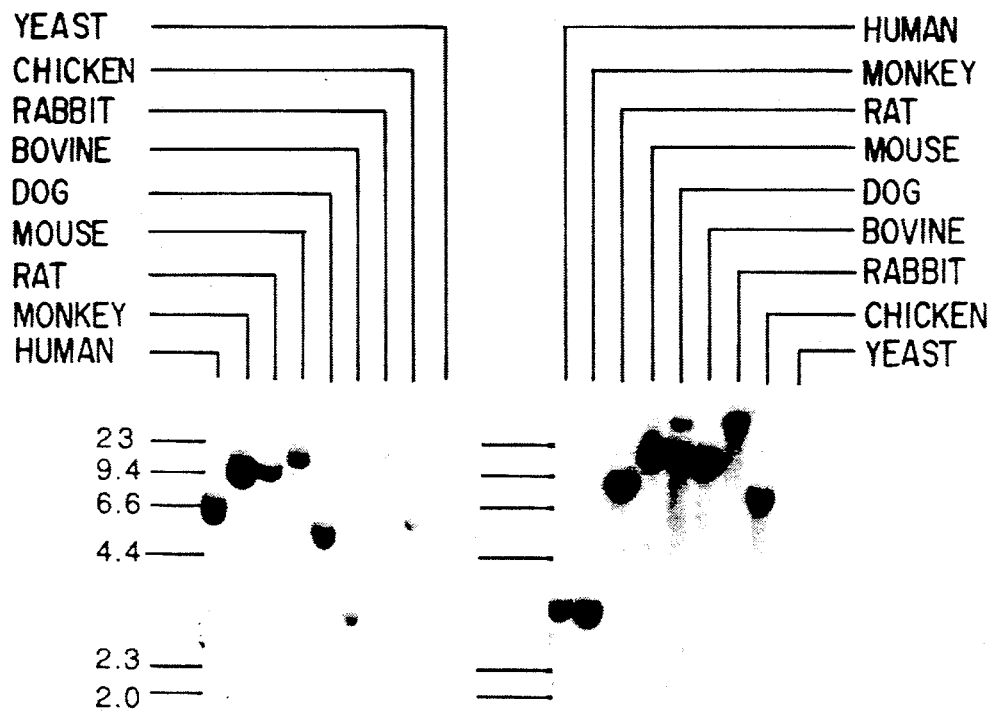

United States Patent [19]

Barde et al.

[11] Patent Number: 5,180,820
[45] Date of Patent: Jan. 19, 1993

[54] BRAIN-DERIVED NEUROTROPHIC FACTOR

[76] Inventors: Yves-Alain Barde, Stiftsbogen 18, Munich 70, Fed. Rep. of Germany, D-8000; Joachim Leibrock, Hangstrasse 32 A, Gauting, Fed. Rep. of Germany, D-8035; Friedrich Lottspeich, Drosselweg 1, Neuried, Austria, D-8021; George Yancopoulos, 100 Haven Ave., Apt. 4A, New York, N.Y. 10032; Hans Thoenen, Kraepelinstrasse 4A, Munich 2, Fed. Rep. of Germany, D-8000

[21] Appl. No.: 400,591

[22] Filed: Aug. 30, 1989

[51] Int. Cl.$^5$ ............. C12P 21/06; C12N 15/00; A61K 37/24; C07H 15/12
[52] U.S. Cl. ............. 536/23.51; 435/69.1; 435/69.3; 435/172.3; 435/320.1; 530/399; 530/412
[58] Field of Search ............. 424/520, 574; 435/69.1, 435/69.3, 172.3, 253, 255; 530/399, 412; 536/27; 800/2

[56] References Cited

U.S. PATENT DOCUMENTS

| | | | |
|---|---|---|---|
| 4,935,370 | 7/1990 | Franke | 435/252.33 |
| 4,945,046 | 7/1990 | Horii et al. | 435/69.3 |

OTHER PUBLICATIONS

Barde et al. (1982) The EMBO Jounal, vol. 5, pp. 549-553.
Hofer et al., (Jan. 1988) Nature, vol. 331, pp. 261-262.
Walz et al, (1987) Biochemical and Biophysical Research Communications vol. 149, pp. 755-761.
Wion et al. (1986) FEBS Letters, vol. 203, pp. 82-86.
Jaenisch (Jun. 10, 1988) Science, vol. 240. pp. 1468-2474.
Hofer and Barde, Nature 331:261-262 (1988).
Rodrigeuz-Tébar and Barde, J. Neurosci. 8(9):3337-3342 (1988).
Barde et al., Prog. Brain Res. 71:185-189 (1987).
Davies et al., Nature 319: 497-499 (1986).
Lindsay and Rohrer, Dev. Biol. 112: 30-48 (1985).
Barde et al., Ann. Rev. Physiol. 45: 601-612 (1983).
Barde et al., EMBO J. 1(5): 549-553 (1982).
Lindsay and Tarbit, Neurosci. Lett. 12: 195-200 (1979).
Thanos et al., 1989, Eur. J. Neurosci. 1: 19-26.
Kalcheim and Gendreau, 1988, Develop. Brain Res. 41: 79-86.
Lindsay, 1988, J. Neurosci. 8:2394-2405.
Kalcheim et al., 1987, EMBO J. 6:2871-2873.
Davies et al., 1986, J. Neurosci. 6:1897-1904.
Johnson et al., 1986, J. Neurosci. 6:3031-3038.
Kalcheim & LeDouarin, 1986, Develop. Biol. 116:451-466.
Barde & Thoenen, "1985 in Hormones and Cell Regulation", vol. 9, Dumont et al., eds., Elsevier Science Publishers, pp. 385-390.

(List continued on next page.)

*Primary Examiner*—David L. Lacey
*Assistant Examiner*—Gian P. Wang

[57] ABSTRACT

The present invention relates to nucleic acid sequences encoding brain derived neurotrophic factor (BDNF), as well as BDNF protein produced in quantity using these nucleic acid sequences, as well as fragments and derivatives thereof. In addition, the invention relates to pharmacologic compositions and therapeutic uses of BDNF, having provided, for the first time, the ability to generate sufficient quantities of substantially pure BDNF for clinical use. The invention also relates to antibodies directed toward BDNF or fragments thereof, having provided a method for generating sufficient immunogen. Further, by permitting a comparison of the nucleic acid sequences of BDNF and NGF, the present invention provides for the identification of homologous regions of nucleic acid sequence between BDNF and NGF, thereby defining a BDNF/NGF gene family; the invention provides a method for identifying an disolating additional members of this gene family.

1 Claim, 26 Drawing Sheets

```
HBDNF      ----100+----200+----300+----400+----500+----600+----700+----800+----900+---1000+---1100+---1200+---1300+---1400+---1500+---1600+

PRE-PRO FORM OF BDN               --------------------------)

MATURE FORM OF BDNF                                              --------------------------)

RBDNF    (3724)          -+----------------+------------------------------------,---------------)   .

RBDNF    (3616)          -------,------------+------------------------------------,---------------)

CKBDNF   ( 414)                                                           -----------)
```

OTHER PUBLICATIONS

Davies and Lindsay, 1985, Develop. Biol. 111:62–72.
Lindsay et al., 1985, J. Cell. Sci. Supp. 3:115–129.
Lindsay & Rohrer, 1985, Develop. Biol. 112:30–48.
Lindsay et al., 1985, Develop. Biol. 112:319–328.
Lindsay & Peters, 1984, Neurosci. 12:45–51.
Pearson et al., 1983, Develop. Biol. 96:32–36.
Sarthy et al., 1983, J. Neurosci. 3:2532–2544.
Turner et al., 1983, Dev. Brain Res. 6:77–83.
Lindsay et al., 1982, Brain Res. 243:329–343.
McCaffery et al., 1982, Exp. Brain Res. 48:377–386.
Barde et al., 1980, PNAS 77:1199–1203.
Johnson et al., 1980, Science 210:916–918.
Lindsay, 1979, Nature 282:80–82.
Barde et al., 1978, Nature 274:818.
Levi-Montalcini, 1966, The Harvey Lectures 60:217–259.

FIG. 1

```
                                                                    AAACCGGG    8

CACCAAAGATTCCCCCCTACCCCTTCTTTTTGACCAAAGGGAACGTGAAAAAATAATAGAGTCTGGGGATTTCGGGGCC   84

GAAGTCTTCCCCAGAGCAGCTGCCTTGATGTTTACTTTGACAAGTAGTGACTGAAAAGTTCCACCAGGTGAGAAGAGTG  166
1                                  10                                 20
Met Thr Ile Leu Phe Leu Thr Met Val Ile Ser Tyr Phe Gly Cys Met Lys Ala Ala Pro
ATG ACC ATC CTT TTC CTT ACT ATG GTT ATT TCA TAC TTC GGT TGC ATG AAG GCT GCC CCC  226
                                  30                                 40
Met Lys Glu Ala Asn Val Arg Gly Gln Gly Ser Leu Ala Tyr Pro Gly Val Arg Thr His
ATG AAA GAA GCC AAC GTC CGA GGA CAA GGC AGC TTG GCC TAC CCA GGT GTG CGG ACC CAT  286
                                  50                                 60
Gly Thr Leu Glu Ser Val Asn Gly Pro Lys Ala Gly Ser Arg Gly Leu Thr Ser Ser Ser
GGG ACT CTG GAG AGC GTG AAT GGG CCC AAG GCA GGT TCA AGA GGC CTG ACA TCG TCG TCA  346
                                  70                                 80
Ser Ser Ser Leu Ala Asp Thr Phe Glu His Val Ile Glu Glu Leu Leu Asp Glu Asp Gln
TCG TCG TCG TTG GCG GAC ACT TTT GAA CAC GTG ATC GAG GAG CTG TTG GAC GAG GAC CAG  406
                                  90                                 90
Lys Val Arg Pro Asn Glu Glu Asn Asn Lys Asp Ala Asp Met Tyr Thr Ser Arg Val Met
AAA GTT CGG CCC AAT GAG GAA AAC AAT AAG GAC GCG GAC ATG TAT ACG TCC CGA GTC ATG  466
                                  110                                120
Leu Ser Ser Gln Val Pro Leu Glu Pro Pro Leu Leu Phe Leu Leu Glu Glu Tyr Lys Asn
CTC AGC AGT CAA GTG CCT TTG GAG CCT CCT CTT CTC TTT CTG CTG GAG GAA TAC AAA AAT  526
                                  130                                140
Tyr Leu Asp Ala Ala Asn Met Ser Met Arg Val Arg Arg His Ser Asp Pro Ala Arg Arg
TAC CTG GAT GCT GCA AAC ATG TCC ATG AGG GTC CGG CGC CAC TCG GAC CCC GCC CGC CGC  586
                                  150                                160
Gly Glu Leu Ser Val Cys Asp Ser Ile Ser Glu Trp Val Thr Ala Ala Asp Lys Lys Thr
GGG GAG CTG AGC GTG TGC GAC AGC ATT AGC GAG TGG GTG ACG GCG GCG GAT AAA AAG ACG  646
                                  170                                180
Ala Val Asp Met Ser Gly Gly Thr Val Thr Val Leu Glu Lys Val Pro Val Ser Lys Gly
GCA GTG GAC ATG TCG GGT GGC ACG GTC ACG GTC CTC GAA AAA GTC CCC GTC TCG AAA GGC  706
                                  190                                200
Gln Leu Lys Gln Tyr Phe Tyr Glu Thr Lys Cys Asn Pro Met Gly Tyr Thr Lys Glu Gly
CAA CTG AAG CAG TAC TTC TAC GAG ACC AAG TGC AAT CCT ATG GGG TAC ACA AAG GAG GGC  766
                                  210                                220
```

FIG. 1 (cont.)

```
Cys Arg Gly Ile Asp Lys Arg His Trp Asn Ser Gln Cys Arg Thr Thr Gln Ser Tyr Val
TGC AGG GGC ATA GAC AAG AGG CAC TGG AAC TCC CAG TGC CGA ACT ACC CAG TCG TAT GTG    826
                                230                                       240
Arg Ala Leu Thr Met Asp Ser Lys Lys Arg Ile Gly Trp Arg Phe Ile Arg Ile Asp Thr
CGG GCC CTC ACC ATG GAT AGC AAA AAA CGA ATT GGC TGG CGG TTC ATA AGG ATA GAC ACT    886
                                250
Ser Cys Val Cys Thr Leu Thr Ile Lys Arg Gly Arg End
TCC TGT GTA TGT ACT TTG ACC ATT AAG AGG GGA AGA TAG TGGCTTTATGTTGTATAGATTATATTG    952

AGACAAAAATTATCTATTTGTATATATACATAACAGGGTAAATTATTCAGTTAAGAAAAAAAATAATTTTATGAACTGC    1031

ATGTATAAATGAAGTTTATACAGTACAGTGGTTCTACAATCTATTTATTGGACATTTCCATGACCAGAGGGAAACAGTC    1110

ATTTTTTGCGCACAACTTTAAAAAAAAAAGTCTGCATTACATTCCTCGATAATGTTGTGGTTTGTTGCCGTTGCT    1184
```

FIG. 2

```
HSDPARRGELSVCDSISEWVTAADKKTAVDMSGGTVTVLEKVPVSKGQLKQYFYETKCNP    pig BDNF
SSSHPIFHRGEFSVCDSVSVWV..GDKTTATDIKGKEVMVLGEVNINNSVFKQYFFETKCRD   human NGF
SSSHPVFHRGEFSVCDSISVWV..GDKTTATDIKGKEVMVLGEVNINNSVFKQYFFETKCRD   bovine NGF
SSTHPVFHMGEFSVCDSVSVWV..ADKTTATDIKGKEVTVLAEVNVNNNVFKQYFFETKCRD   g. pig NGF
SSTHPVFHMGEFSVCDSVSVWV..GDKTTATDIKGKEVTVLAEVNINNSVFRQYFFETKCRA   mouse NGF
TAHPVLHRGEFSVCDSVSMWV..GDKTTATDIKGKEVTVLGEVNINNNVFKQYFFETKCRD    chick NGF
EDHPVHNLGEHSVCDSVSAWV...TKTTATDIKGNTVTVMENVNLDNKVYKQYFFETKCKN    snake NGF MGYTKEGCRGIDKRHVNSQCRTTQSYVRALTMDSKKRIGVRFIRIDTSCVCILTIKRGR      pig BDNF
PNPVDSGCRGIDSKHVNSYCTTTHTFVKALTMDGKQ.AAVRFIRIDTACVCVLSRKAVRRA    human NGF
PNPVDSGCRGIDAKHVNSYCTTTHTFVKALTMDGKQ.AAVRFIRIDTACVCVLSRKTGQRA    bovine NGF
PSPYESGCRGIDSKHVNSYCTTTHTFVKALTTDNKQ.AAVRFIRIDTACVCVLNRKAARRG    g. pig NGF
SNPVESGCRGIDSKHVNSYCTTTHTFVKALTTDEKQ.AAVRFIRIDTACVCVLSRKATRRG    mouse NGF
PRPVSSGCRGIDAKHVNSYCTTTHTFVKALTMCGKQ.AAVRFIRIDTACVCVLSRKSGRP     chick NGF
PNPEPSGCRGIDSSHVNSYCTETDTFIKALTMEGNQ.ASVRFIRIETACVCVITKKKGN      snake NGF
```

FIG.5B

```
            10         20         30         40         50         60         70         80         90        100        110        120
             .          .          .          .          .          .          .          .          .          .          .          .
HUMAN  AAGCTTGATATCGAATTCCGGTTCCCAACTGCTGTTTATTGTGCTATTCATGCTAGAGATCACATAGCTAGAAAGGCCCATCAGAGACCCTCAGGCCACTGCTGTTCCTGTCACACATTC
       TTCGAACTATAGCTTAAGGCCTTAAGGCAAGGGTTGACGACAAAATAACACGATAAGTACGATCGTAGTGTATCGATCTTCCGGGTAGTCTGGGAGTCCGGTGACGACAAGGACAGTGTGTAAG 130        140        150        160        170        180        190        200        210        220        230        250
             .          .          .          .          .          .          .          .          .          .          .          .
HUMAN  CTGCAAAGGACCATGTTGCTAACTTGAAAAAATTACTATTAATTACACTGCAGTTGTTGCTTAGTAACATTTATGATTTGTTGTTTCTCGTGACAGCATGAGCAGAGATCATTAAAAATTAAACTTA
       GACGTTTCCTGGTACAAGCGATTGAACTTTTTTAATGATAATTAATTAATGTGAACGTCAACAACGAATCATTGTAAATACTAAAACACAAAGAGCACTGTCTGCTACTCGTCTCTAGTAATTTTAATTTGAAT 260        270        280        290        300        310        320        330        340        350        360        370        380
             .          .          .          .          .          .          .          .          .          .          .          .          .
HUMAN  CAAAGCTGCTAAAGTGGGAAGAAGGAGAACTTGAAGCCACAATTTTTGCACTTGCTTAGAAGCCATCTAATCTCAGGTTATATGCTAGATCTTGGGGGCAAACACTGCATGTCTCTGGTTATATTAAA
       GTTTCGACGATTTCACCCTTCCTCCTCTTGAACTTCGGTGTTAAAAACGTGAACAATCTTCGGTAGAATTAGAGTCCAATATACGATCTAGAGAATCTAGAGACCAAATATAATTT
                                                                                          HBDNF 390        400        410        420        430        440        450        460        470        480        490        500        510
             .          .          .          .          .          .          .          .          .          .          .          .          .
HUMAN  CCACATACAGCACACTACTGACACTGCATTTGTGTCTGGTGCAGCTGGAGTTTATCACCAAGACATAAAAAAAACCTTGACCCTGCGAGAATGGCCTGGAATTACAATCAGATGGGCCACATGGCATCCGG
       GGTGTATGTCGTGTGATGACTGTGACGTAAACAGACAGACCACGTCGACCTCAAATAGTGGTTCTGTATTTTTTTGGAACTGGGACGTCTTAATGTTAGTCTACCGGTGTACCGTAGGGCC

C

..A..T...>
RAT     4                                                                      ...CA..GGG....G.G..AAAATA.T.GA.T.TG..G...----..-...... G.A.T.T....-C
PIG    39
```

```
HUMAN  520        530        540        550        560        570        580        590        600        610        620        630
       TGAAGAAAGCCCTAACCAGTTTTCTGTCTTGTTCTGCTTTCTCCCTACAGTTCCACCAGGTGAGAAGAGTG ATG ACC ATC CTT TTC CTT ACT ATG GTT ATT TCA TAC TTT GGT
       ACTTCTTTCGGGATTGGTCAAAGACAGAGAAACAAAGAGACGAAAGAGGGATGTCAAGGTGGTCCACTCTTCTCAC TAC TGG TAG GAA AAG TGA GAA TAC CAA TAA AGT ATG AAA CCA
                                                                              Met Thr Ile Leu Phe Leu Thr Met Val Ile Ser Tyr Phe Gly)
                                                                              ─────────────── PRE-PRO FORM OF BDNF ──────────────>
                                            HBDNF

RAT 17 CCTTG..C..AG.-C.G.G.A...G.-C.GA.G.GG.-AG.A..T.A.C.........................................C....>
PIG 99 A..GCAGCT...T.G.-T....A..-.-.GACAAG.AG.GA.-AAA.A..............................................C....>
```

FIG. 5C

```
          640              650              660              670              680              690              700              710              720
HUMAN     TGC ATG AAG GCT GCC CCC ATG AAA GAA AAC ATC CGA GCA AAC ATC CGA GGA CAA GGT GGC TTG GCC TAC CCA GGT GTG CGG ACC CAT GGG ACT CTG GAG AGC GTG
          ACG TAC TTC CGA CGG GGG TAC TTT CTT CGT TAG GCT CCT GTT CCA GAC CGG ATG CCG GGT GGG GTG CCC GCC ATG TGG GTA CCC TGA CTC CAC
          Cys Met Lys Ala Ala Pro Met Lys Glu Asn Ile Arg Ala Asn Ile Arg Gly Gln Gly Gly Leu Ala Tyr Pro Gly Val Arg Thr His Gly Thr Leu Glu Ser Val
                                                                                              ␣␣PRE-PRO FORM OF BDNF␣␣

RAT  129  .................................G................................G....AC...........C.........................
PIG  209  ...........................................................................C....C AA...........................
                                                                                         C A........................

730              740              750              760              770              780              790              800              810              820
HUMAN     AAT GGG CCC AAG GCA GGT TCA AGA GGC TTG ACA TCA TTG GCT GAC ACT TTC GAA CAC GTG ATA GAA GAG TTG TTG GAT GAG CAG AAA GTT CGG
          TTA CCC GGG TTC CGT CCA AGT TCT CCG AAC CTG TGA AAG CGA CTG TGT GCA CTA TCT TCT CTC AAC AAC CTA CTC GTC TTT CAA GCC
          Asn Gly Pro Lys Ala Gly Ser Arg Gly Leu Thr Ser Leu Ala Asp Thr Phe Glu His Val Ile Glu Glu Leu Leu Asp Glu Gln Lys Val Arg
                                                                                                         ␣␣PRE-PRO FORM OF BDNF␣␣

CGACGA
                                   ^
                       ATCGTGTCATCGTC
                                ^
RAT  225  .........G..............G........TC...G..C.C.............T..G............C............C.........
PIG  305  ...................C..G..G..............G...........T...............C..G..........C.........
```

FIG.5D

```
                                                                |HBDNF|
         830        840        850        860        870        880        890        900        910
HUMAN    CCC AAT GAA AAC AAT AAG GAC GCA GAC TTG TAC ACG TCC AGG GTG ATG CTC AGT AGT CAA GTG CCT TTG GAG CCT CCT CTT CTC TTT CTG CTG
         GGG TTA CTT TTA TTC CTG CGT CTG AAC ATG TGC AGG TCC CAC TAC GAG TCA TCA GTT CAC GGA AAC CTC GGA GGA GAA GAG AAA GAC GAC
         Pro Asn Glu Asn Asn Lys Asp Ala Asp Leu Tyr Thr Ser Arg Val Met Leu Ser Ser Gln Val Pro Leu Glu Pro Pro Leu Leu Phe Leu Leu
         a   a   a   a   a   a   a   a   a   a   a   a   a   a   a_a_PRE-PRO FORM OF BDNF_a_____a_____a_____a_____a_____a_____a_____a
RAT  327 ....C.. ........ ........ ........ ........ ..T ....C.. ........ ........ ........ ........ ........ ....G.. ........ ........
PIG  416 ........ ..G..... ....G... ....A... ..T ....C.A ..C ........ ........ ........ ........ ........ ........ ........ ........
```

FIG. 5E

```
                 920         930         940         950         960         970         980         990         1000        1010
HUMAN   GAG GAA TAC AAA AAT TAC CTA GAT GCT GCA AAC ATG TCC ATG AGG GTC CGG CGC CAC TCT GAC CCT GCC CGC CGA GGG GAG CTG AGC GTG TGT GAC
        CTC CTT ATG TTT TTA GAT CTA CGA CGT TTG TAC AGG TAC TCC CAG GCC GTG CTG GGA CGG GCT CCC CTC GAC CTG
        GAG GAG TGG CGT CAG CGA CGA CGA CGA CGA CGA
        Glu Glu Ser Lys Asn Tyr Leu Asp Ala Ala Asn Met Ser Met Arg Val Arg Arg    His Ser Asp Pro Ala Arg Arg Gly Glu Leu Ser Val Cys Asp
                                                    a  a  a  a  a PRE-PRO FORM OF BDNF a  a  a  a  a  a  a   b  b  b  b MATURE FORM OF BDNF b  b  b  b
                                                         └─────────────────────HBDNF─────────────────────┘
RAT 423 ... ... ... ... ... ..C ... ... ..G ... ... ... ... ... ..T ... ... ... ... ..C ... ... ... ... ..T ... ... ... ... ...
PIG 512 ..C ... ... ... ..C ... ... ..G ... ..G ... ... ... ... ... ... ..G ... ... ..C ... ... ... ... ... ... ... ... ... ...

1020        1030        1040        1050        1060        1070        1080        1090        1100        1110
HUMAN   AGT ATT AGT GAG TGG GTA ACG GCG GCA GAC AAA AAG ACT CTG TTT TTC TGA CGT CTG CTG GGG ACG GTC CTT GAA AAG GTC CCT GTA TCA AAA
        TCA TAA TCA CTC ACC CAT TGC CGC CGT CTG TTT GAG ACA AAG ACG GCA ATG TCG GGC CCG TGC CAG CTT CAG GAA CTT CAG CAT AGT TTT
        Ser Ile Ser Glu Trp Val Thr Ala Ala Asp Lys Lys Thr Val Phe   Arg Leu Leu Gly Thr Val His Cys Gln Leu Gln Asp Met Ser Gly Gly Thr Val Leu Glu Lys Val Pro Val Ser Lys
                                                                      b  b  b  b  b  b  b  b  b  b MATURE FORM OF BDNF b  b  b  b  b  b  b  b  b  b  b  b  b  b  b  b  b  b
                                                                      └────────────────────────HBDNF────────────────────────┘
RAT 519 ... ... ... ... ..C ... ..C ..A ... ... ... ..T ... ... ..C ..T ... ... ... ... ... ... ... ..G ... ..A ... ..G ... ... ..G
PIG 608 ..C ..C ... ... ..G ..G ... ... ... ..G ... ..T ... ..G ... ..T ..C ..G ... ... ... ... ..C ..G ... ..A ... ..C ..C ..G
```

FIG.5F

FIG. 5G

HUMAN

```
        1120            1130            1140            1150            1160            1170            1180            1190            1200
         |               |               |               |               |               |               |               |               |
                                                                         ├─HBDNF
        GGC CAA CTG AAG CAA TAC TTC TAC GAG ACC AAG TGC AAT CCC ATG GGT TAC ACA AAA GAA GGC TGC AGG GGC ATA GAC AAA AGG CAT AAC TCC
        CCG GTT GAC TTC GTT ATG AAG ATG CTC ACG TTC CCA ATG TTA GGG TAC TTC ACG TGT CTT CCG ACG TCC CCG TAT CTG TTT TCC GTA ACC TTG AGG
        Gly Gln Leu Lys Gln Tyr Phe Tyr Glu Thr Lys Cys Asn Pro Met Gly Tyr Thr Lys Glu Gly Cys Arg Gly Ile Asp Lys Arg His Asn Ser
         b   b   b   b   b   b   b   b   b   b   b   b   b   b   b   b   b   b   b  b_MATURE FORM OF BDNF  b   b   b   b   b   b   b
```

```
RAT     615 ..... ..... ..... ..... ....T ..... ..... ..... ..... ..... ..... ..... ..... ....C .....
PIG     704 ..... ..... ..... ..... ..... ....G ....T ..... ...G. ..... ....G. ..... ..... ....C .....
CHICKEN  1  ..... ..... ..... ..... ....T ...A. ..A.. ....T ..G.. ..A.. ....G ..... ..... ....C ....A
```

HUMAN

```
        1210            1220            1230            1240            1250            1260            1270            1280            1290            1300
         |               |               |               |               |               |               |               |               |               |
                                                                                         ├─HBDNF
        CAG TGC CGA ACT ACC CAG TCG TAC GTG CGG GCC CTT ACC ATG GAT AGC AAA AAG AGA ATT GGC TGG CGA TTC ATA AGG ATA GAC ACT TCT TGT GTA
        GTC ACG GCT TGA TGG GTC AGC ATG AGC CGG CCG GAA TGG ACC TAC CTA TCG TTT TCT TAA CCG ACC GCT AAG TAT TCC TAT CTG TGA AGA ACA CAT
        Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val
         b   b   b   b   b   b   b   b   b   b   b   b   b   b   b  b_MATURE FORM OF BDNF  b   b   b   b   b   b   b   b   b   b   b   b
```

FIG. 5H

```
                                                                        HBDNF
          1430      1440      1450      1460      1470      1480      1490      1500      1510      1520      1530      1540      1550
HUMAN     AAAATAATTTTATGAACTGCATGTATAAATGAAGTTTATACAGTACAGTGGTTCTACAATCTATTTATTGGACATGTCCATGACCAGAAGGGAAACAGTCATTTGCGCACAACTTAAAAAGTCTGCATT
          TTTTATTAAAATACTTGACGTACATATTTACTTCAAATATGTCATGTCACCAAGATGTTAGATAAATAACCTGTACAGGTACTGGTCTTCCCTTTGTCAGTAAACGCGTGTTGAATTTTTCAGACGTAA

RAT   922 ..G.....................................................................A..............._A........................T...........
                                                                                                     TTT        TTTAA
                                                                                                      ^           ^
PIG  1012 ....................................................................T..........._.......................AA.............

HBDNF
           1560      1570      1580      1590      1600      1610
HUMAN     ACATTCCTTGATAATGTTGTGGTTTGTTGCCGTTGCCAAGAACTGAAAACGGAATTCCTGCAG
          TGTAAGGAACTATTACAACACCAAACAACGGCAACGGTTCTTGACTTTTGCCTTAAGGACGTC

RAT  1050 ........C..................................T......AA..

PIG  1140 ........C.........................
```

FIG.5I

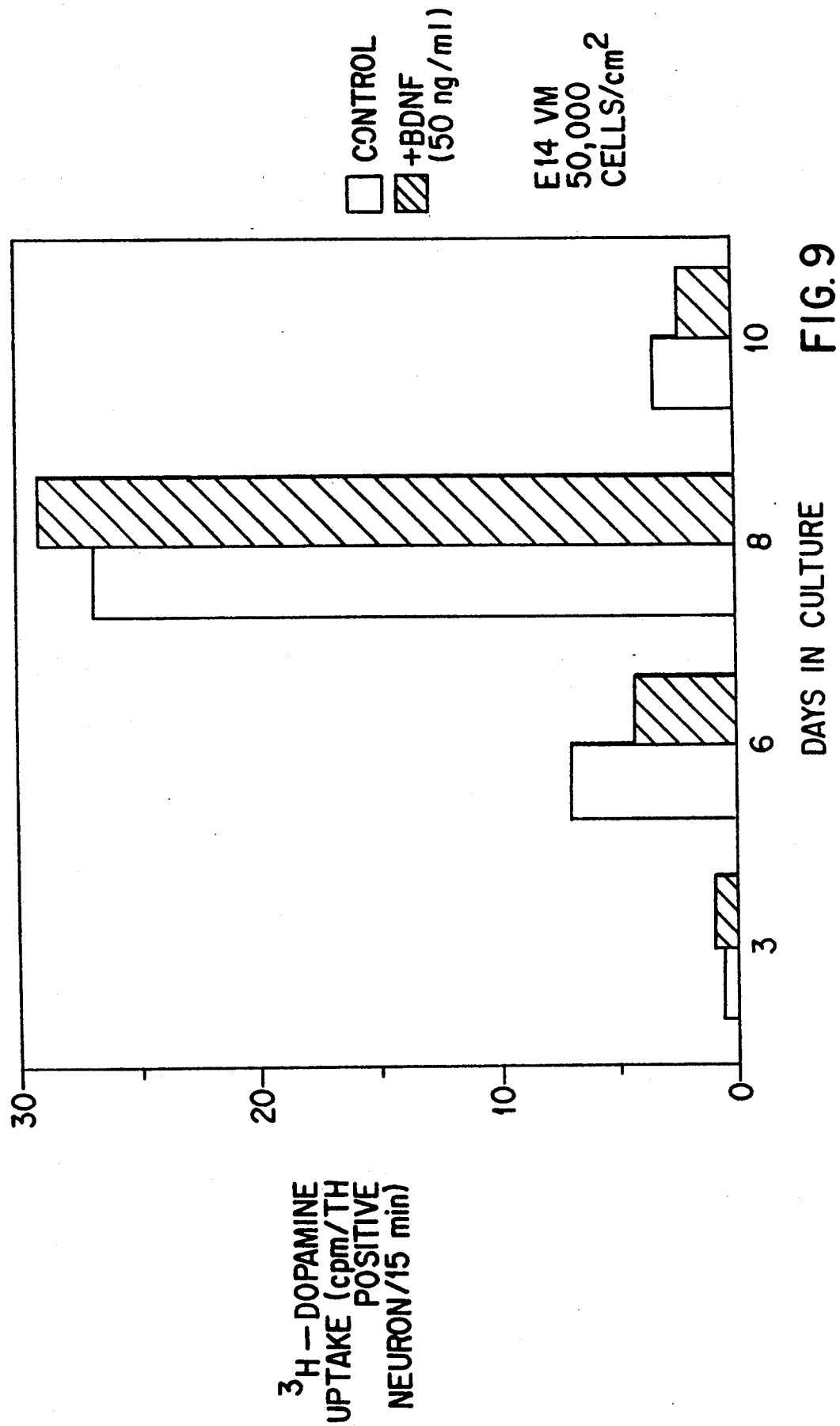

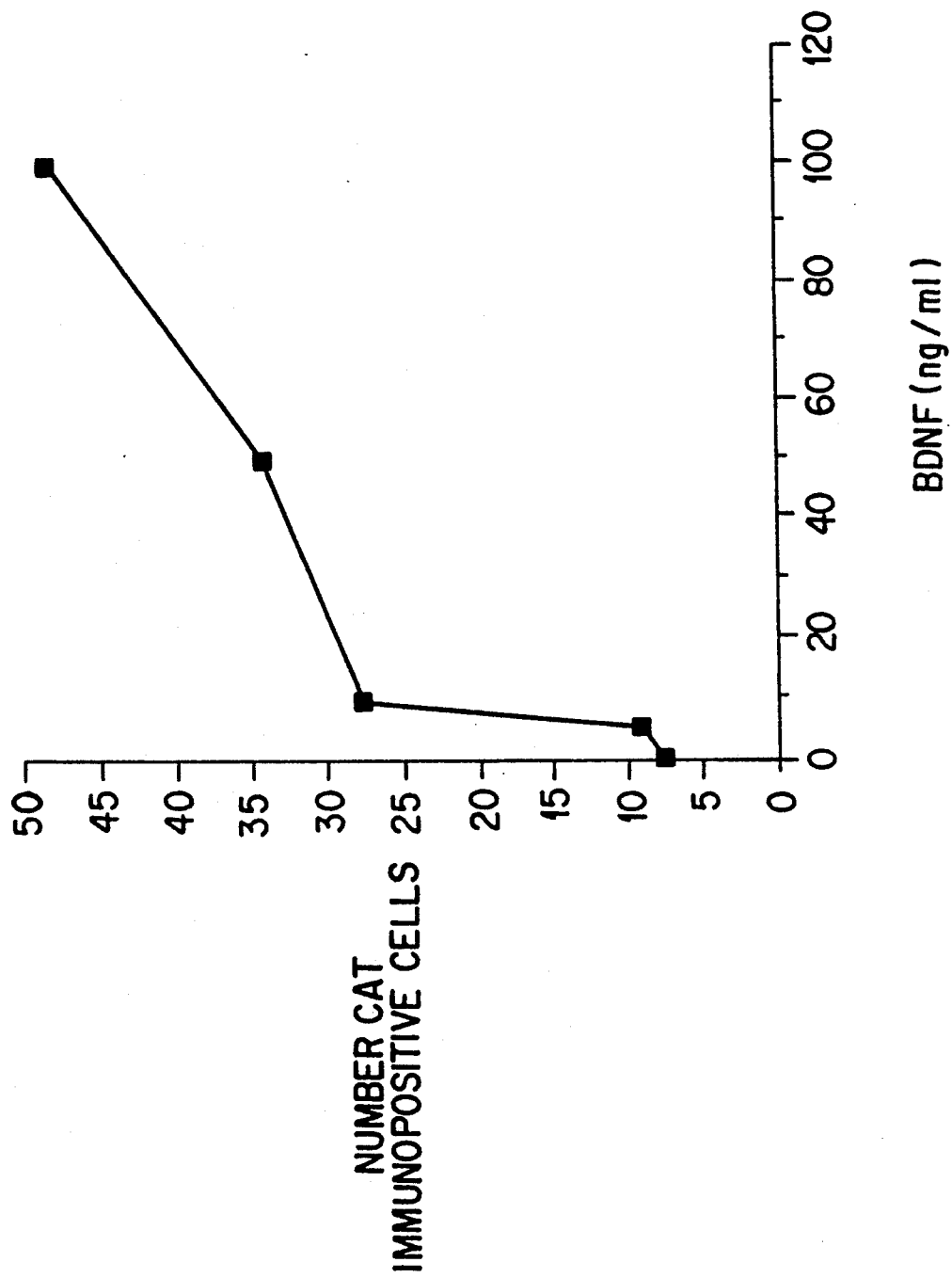

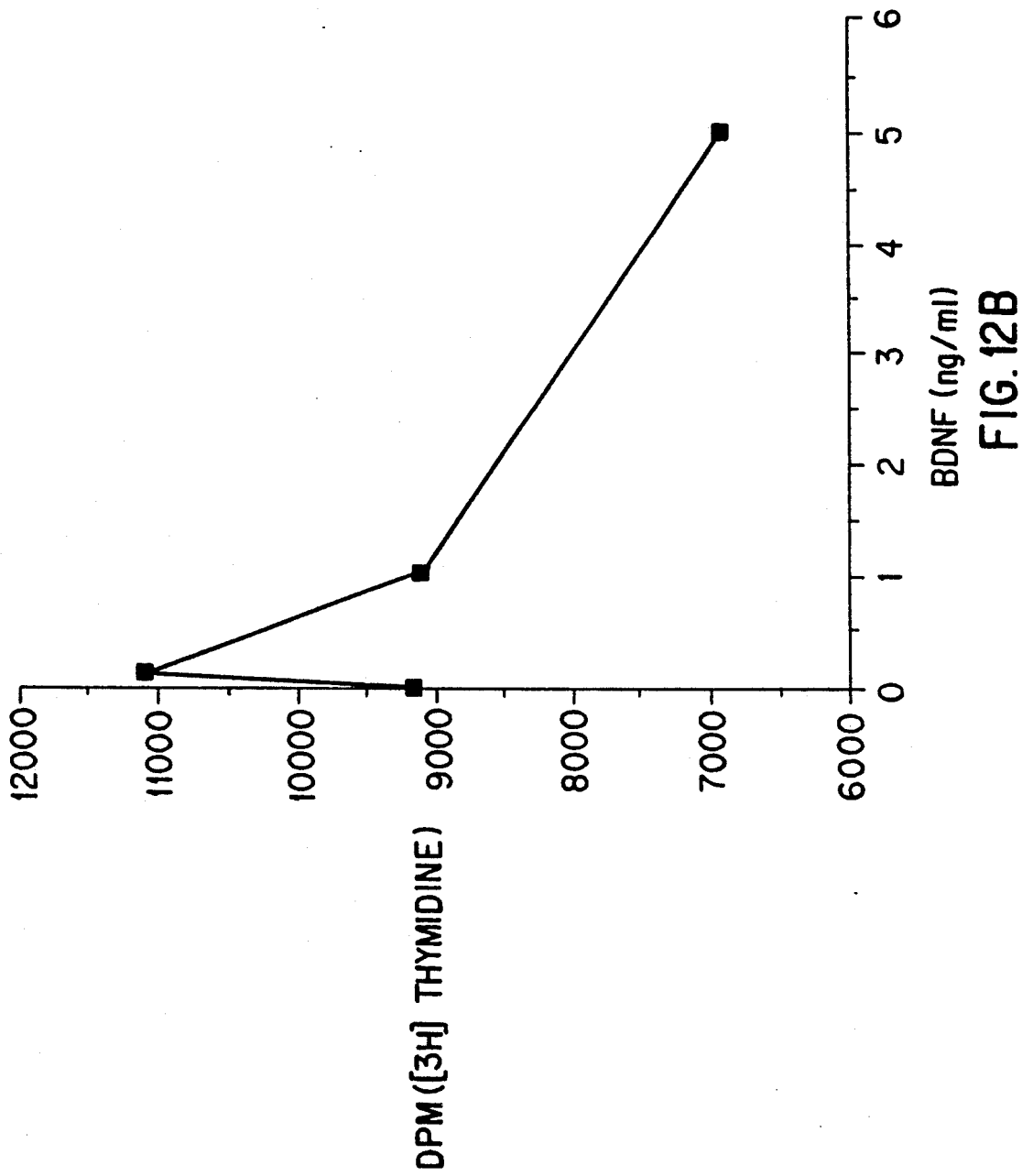

```
M3/4    GAT GAC AAA CAC TGG AAC TCT CAG TGC AAA ACT TCG CAA ACC
        Asp Asp Lys His Trp Asn Ser Gln Cys Lys Thr Ser Gln Thr

MuNGF   Asp Ser Lys His Trp Asn Ser Tyr Cys Thr Thr Thr His Thr

HuBDNF  Asp Lys Arg His Trp Asn Ser Gln Cys Arg Thr Thr Gln Ser

M3/4    TAT GTC CGA GCA CTG ACT TCA GAA AAC AAC AAA CTC GTA GGC
        Tyr Val Arg Ala Leu Thr Ser Glu Asn Asn Lys Leu Val Gly

MuNGF   Phe Val Lys Ala Leu Thr Thr Asp --- Glu Lys Gln Ala Ala

HuBDNF  Tyr Val Arg Ala Leu Thr Met Asp Ser Lys Lys Arg Ile Gly

M3/4    TGG CGC TGG ATA CGA ATA GAC ACT TCC TGT GTG TGT GCC TTG
        Trp Arg Trp Ile Arg Ile Asp Thr Ser Cys Val Cys Ala Leu

MuNGF   Trp Arg Phe Ile Arg Ile Asp Thr Ala Cys Val Cys Val Leu

HuBDNF  Trp Arg Phe Ile Arg Ile Asp Thr Ser Cys Val Cys Thr Leu

M3/4    TCG AGA AAA ATT GGA AGA ACA TGA ATT GGC ATC TGT CCC CAC
        Ser Arg Lys Ile Gly Arg Thr End

MuNGF   Ser Arg Lys Ala Thr Arg Arg Gly END

HuBDNF  Thr Ile Lys Arg Gly Arg END

M3/4    ATA TAA ATT GAT TGG ACT NNA AAT TAT ATG ATA TGC ATG TAG

M3/4    CAT ATA AAT GTT TAT ATT TTT ATA TAT TAT AAG TTG ACC TCT

M3/4    ATT TAT TAA ACT TCA GCA ACC CTT
```

FIG. 14

```
        18S 28S
         |   |
              CHP100
              CHP126
              CHP134
           ●  CHP234
              LAN1
           ●  LAN5
              NB9
              SY5Y
              Y79
              FO1
              BU2
              HO1
              HL60
              COL320
```

FIG. 15

BRAIN-DERIVED NEUROTROPHIC FACTOR

TABLE OF CONTENTS

Figure 5A:
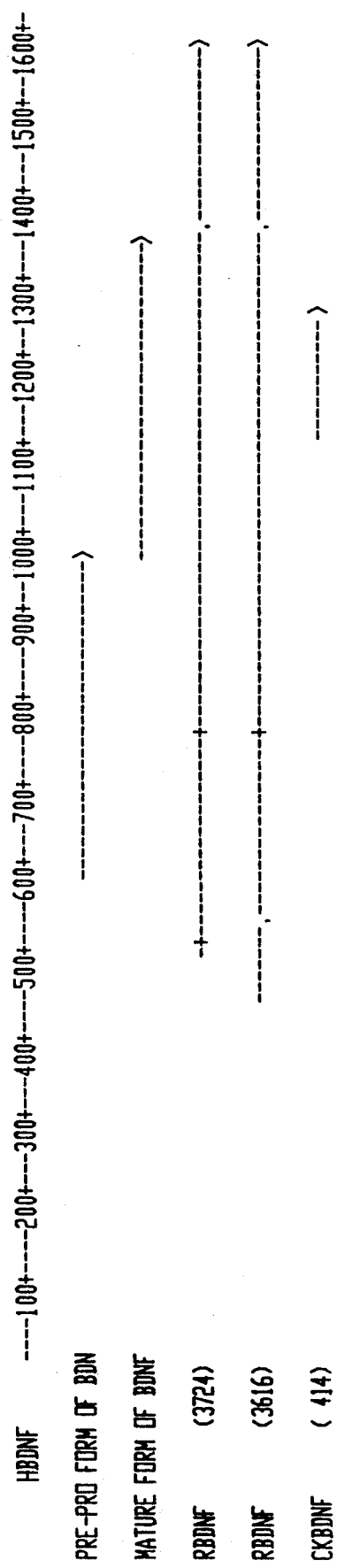
Figure 5H:
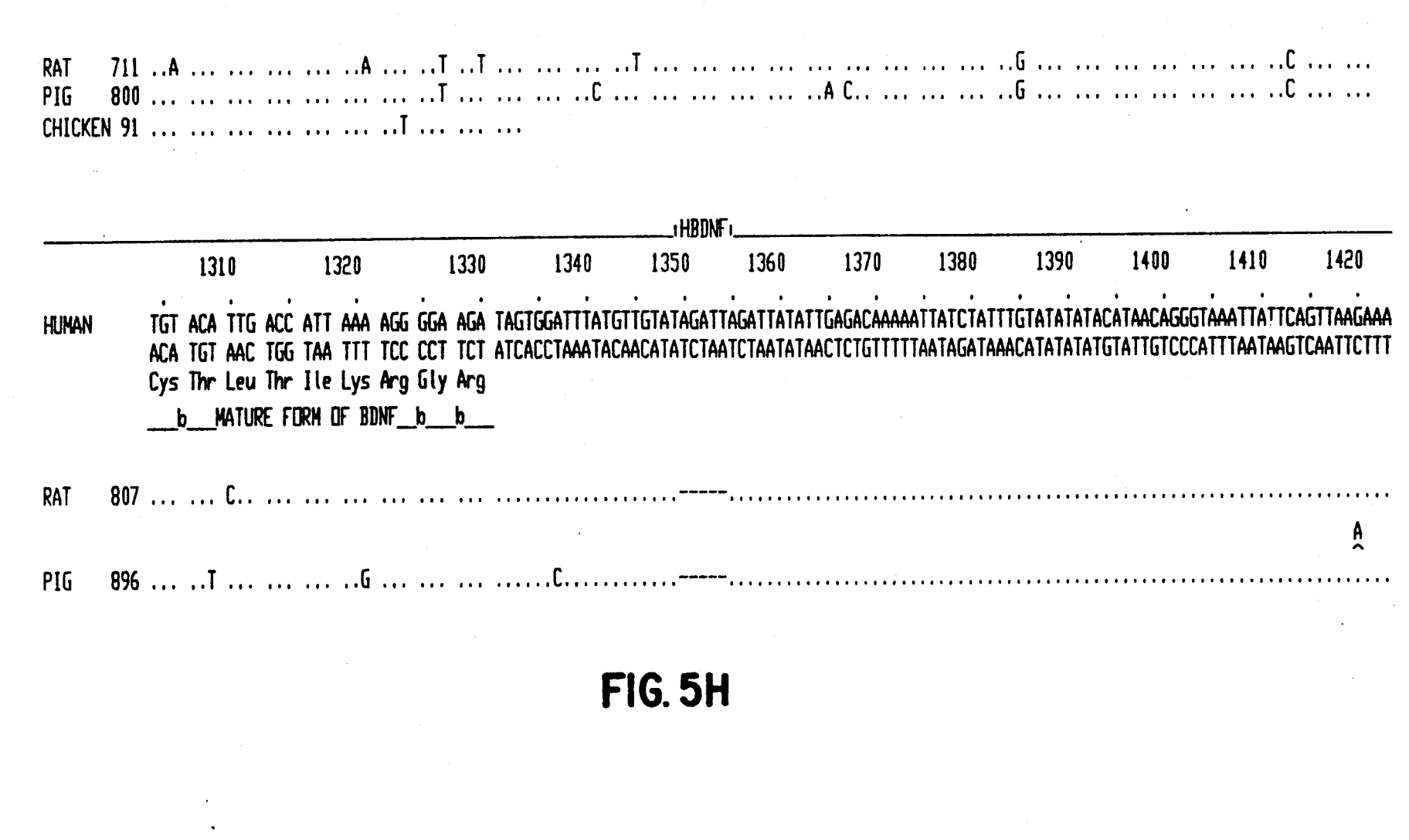

1. Introduction
2. Background of the Invention
   2.1. Neuronal Cell Death And The Role Of Neurotrophic Factors In The Development Of The Nervous System
   2.2. Nerve Growth Factor
   2.3. Other Neurotrophic Factors
      2.3.1. Comparison Of Brain Derived Neurotrophic Factor (BDNF) And Nerve Growth Factor
      2.3.2. Neuronal Targets Of Brain Derived Neurotrophic Factor
3. Summary of the Invention
   3.1. Abbreviations And Definitions
4. Description of the Figures
5. Detailed Description of the Invention
   5.1. Purification of Brain Derived Neurotrophic Factor
   5.2. Brain Derived Neurotrophic Factor Bioassays
   5.3. Microsequencing Of Brain Derived Neurotrophic Factor Protein
   5.4. Cloning Of Brain Derived Neurotrophic Factor-Encoding DNA
   5.5. Expression Of A Brain Derived Neurotrophic Factor Gene
      5.5.1 Identification And Purification Of The Expressed Gene Product
   5.6. Brain Derived Neurotrophic Factor Genes And Proteins
   5.7. Generation Of Anti-Brain Derived Neurotrophic Factor Antibodies
   5.8. Identification Of Additional Members Of The BDNF/NGF Gene Family
   5.9. Utility Of The Invention
      5.9.1. Diagnostic Applications
      5.9.2. Therapeutic Applications
   5.10. Pharmaceutical Compositions
6. Example: Molecular Cloning and Characterization of Porcine Brain Derived Neurotrophic Factor cDNA
   6.1. Materials And Methods
      6.1.1. Purification of BDNF From Porcine Brain
      6.1.2. Protein Sequencing
      6.1.3. Preparation Of DNA Templates
      6.1.4. Polymerase Chain Reaction
   6.2. Results And Discussion
      6.2.1. Results Of Protein Microsequencing
      6.2.2. Synthesis Of Oligonucleotides And Use Of PCR To Obtain DNA Encoding An Amino Acid Fragment
      6.2.3. Nucleotide Sequence Of cDNA Fragment
      6.2.4. Cloning Of The Entire Porcine BDNF cDNA
      6.2.5. Nucleotide Sequence Of Porcine BDNF cDNA
7. Example: BDNF Gene Is Distinct From The NGF Gene In Diverse Vertebrate Species
   7.1. Materials And Methods
      7.1.1. Preparation Of NGF and BDNF Probes
      7.1.2. Sequencing Of BDNF Genes From Various Species
   7.2. Results And Discussion
8. Example: Expression Of BDNF RNA In Neuronal Versus Non-Neuronal Tissues
   8.1. Materials and Methods
      8.1.1. Preparation Of RNA
      8.1.2. Preparation Of cRNA Probe
   8.2. Results And Discussion
9. Example: Molecular Cloning And Characterization Of Human And Rat BDNF Genes
   9.1. Materials And Methods
      9.1.1. Genomic DNA and cDNA Libraries
      9.1.2. Preparation Of BDNF DNA Probes
      9.1.3. Screening Of Libraries
   9.2 Results and Discussion
10. Example: Expression Of Recombinant BDNF
    10.1. Materials And Methods
       10.1.1. Preparation Of A BDNF Expression Vector
       10.1.2. Expression Of BDNF in COS Cells
    10.2. Results And Discussion
11. Example: Generation Of Antibodies To BDNF
    11.1. Materials And Methods
       11.1.1. Peptide Synthesis
       11.1.2. Immunization
       11.1.3. Detection Of Antibody Binding To BDNF
    11.2. Results
12. Example: Novel Biological Effects Of BDNF
    12.1. Materials And Methods
       12.1.1. Methods For Culturing Dopaminergic Substantia Nigra Neurons
       12.1.2. Methods For Immunocytochemical Staining Of Ventral Mesencephalon Cultures
       12.1.3. Methods Used in Measuring $^3$H-Dopamine Uptake In Ventral Mesencephalon Cultures
       12.1.4. Methods For Producing Cultures Of Basal Forebrain Cholinergic Neurons
       12.1.5. Choline Acetyl Transferase Assays
       12.1.6. Method Of Generating Purified Astroglial Cell Cultures
    12.2. Results
       12.2.1. The Effect Of BDNF On Tyrosine Hydroxylase And Gamma Aminobutyric Acid Present In Ventral Mesencephalon
       12.2.2. The Effect Of BDNF On Dopamine And Gamma Aminobutyric Acid Uptake By Ventral Mesencephalon Cultures
       12.2.3. The Effect Of BDNF On Choline Acetyltransferase Expression By Forebrain Cholinergic Neurons
       12.2.4. Effects Of BDNF Or EGF On Astroglial Cell Cultures
    12.3. Discussion
13. Example: Identification of a Novel Gene in the BDNF/NGF Gene Family
    13.1. Materials and Methods
       13.1.1. Polymerase Chain Reaction
    13.2. Results
       13.2.1. Amplification Of Both NGF and BDNF Sequences rom Genomic DNA
       13.2.2. Detection of Sequences Complementary to the BDNF/NGF Probe in Genomic DNAs of Various Species
       13.2.3. Identification of a Novel Gene Related to BDNF and NGF
       13.2.4. Characterization of a Novel Member of the BDNF/NGF Gene Family
    13.3. Discussion
14. Example: Increased Expression of BDNF in Neuroblastoma Cells
    14.1. Materials and Methods
       14.1.1. Cell Lines
       14.1.2. Preparation of RNA 14.2. Results and Discussion
15. Deposit Of Microorganisms

1. INTRODUCTION invention relates to nucleic acid sequences encoding brain derived neurotrophic factor (BDNF), to the substantially pure protein, peptide fragments or derivatives produced in quantity therefrom, and to antibodies directed toward BDNF protein, peptide fragments, or derivatives. In addition, the invention relates to genes that are members of a newly defined BDNF/NGF gene family, and to their gene products. The invention also relates to pharmaceutical compositions comprising effective amounts of BDNF gene products or, alternatively, antibodies directed toward BDNF gene products, and to methods of diagnosing and treating a variety of neurological diseases and disorders, including Alzheimer's disease and Parkinson's disease. In particular, the BDNF gene products of the invention have value in the diagnosis and therapy of disorders of sensory neurons as well as degenerative diseases of the retina.

2. BACKGROUND OF THE INVENTION

2.1. Neuronal Cell Death and the Role of Neurotrophic Factors in the Development of the Nervous System Throughout many parts of the vertebrate nervous system many more neurons are present during early development than are found in the adult animal. Periods of early development are characterized by waves of naturally occurring neuronal cell death (Carr and Simpson, 1978, J. Comp. Neurol., 182:727–740; Cowan et al., 1984, Science 225:1258–1265). The survival, differentiation and maturation of developing neurons may be regulated by environmental or 'epigenetic' factors rather than by a strict intrinsic genetic program. For example, experimental manipulations of the chick embryo have shown that transplantation or extirpation of peripheral "target fields", such as a limb bud or the eye, at early stages in chick development can result in a corresponding increase or decrease, respectively, in the number of sensory, sympathetic, parasympathetic or motorneurons adjacent to the enlarged or depleted target field (Hamburger, 1934, J. Exp. Zool. 68:449; Hollyday and Hamburger, 1976, J. Comp. Neurol., 170:311–321; Landmesser and Pilar, 1976, J. Cell. Biol., 68:357–374). A target field may only support a limited number of neurons, and a normal part of the developmental process may be the pruning of an excess number of neurons to match the "neurotrophic" capacity of the target tissue. The discovery and isolation of the protein now called nerve growth factor (NGF) has led to a molecular hypothesis of how a target may be able to regulate the number of neurons which survive and innervate that tissue (Levi-Montalcini et al., 1968, Physiol Rev., 48:524–569; Thoenen and Barde, 1980, Physiol Rev. 60:1284–1335).

It is now well established, at least in the peripheral nervous system, that neuronal target tissues synthesize and release limited quantities of various neurotrophic molecules which are critical to the survival of specific types of neurons (Korsching and Thoenen, 1983, Proc. Natl. Acad. Sci. U.S.A. 80:3513–3516; Heumann et al., 1984, EMBO J. 3:3183–3189; Shelton and Reichardt, 1984, Proc. Natl. Acad. Sci U.S.A. 81:7051–7955; Korsching and Thoenen, 1985, Neurosci. Lett. 54:201–205).

2.2. Nerve Growth Factor

Nerve growth factor (NGF) is by far the most fully characterized of these neurotrophic molecules and has been shown, both in vitro and in vivo, to be essential for the survival of sympathetic and neural crest-derived sensory neurons during early development of both chick and rat (Levi-Montalcini and Angeletti, 1963, Develop. Biol. 7:653–659; Levi-Montalcini et al., 1968, Physiol. Rev. 48:524–569). Injections of purified NGF into the developing chick embryo have been found to cause massive hyperplasia and hypertrophy of spinal sensory neurons and sympathetic neurons (Levi-Montalcini and Booker, 1960, Proc. Natl. Acad. Sci. U.S.A. 46:373–384; Hamburger et al., 1981, J. Neurosci. 1:60–71). Conversely, removal or sequestration of endogenous NGF by daily injection of anti-NGF antibodies into neonatal rats has been associated with virtual destruction of the sympathetic nervous system (Levi-Montalcini and Booker, 1960, Proc. Natl. Acad. Sci. U.S.A. 46:384–391; Levi-Montalcini and Angeletti, 1966, Pharmacol. Rev. 18:619–628). Exposure to NGF antibodies even earlier in development either by antibody injections in utero or by passive transplacental transfer of maternal antibodies has been shown to result in a substantial loss of neural crest-derived sensory neurons such as spinal and dorsomedial trigeminal sensory neurons (Goedert et al., 1984, Proc. Natl. Acad. Sci. U.S.A. 81:1580–1584; Gorin and Johnson, 1979, Proc. Natl. Acad. Sci. U.S.A. 76:5382–5386). Until recently, almost all studies of NGF had focused on its role in the peripheral nervous system, but it now appears that NGF also influences the development and maintenance of specific populations of neurons in the central nervous system (Thoenen et al., 1987, Rev. Physiol. Biochem. Pharmacol. 109:145–178; Whittemore and Seiger, 1987, Brain Res. Rev. 12:439–464).

The serendipitous discovery of large amounts of NGF protein in the submandibular gland of the adult male mouse (Cohen, 1960, Proc. Natl. Acad. Sci. U.S.A. 46:302–311) and an earlier discovery of high levels of NGF in snake venom (Cohen and Levi-Montalcini, 1956, Proc. Natl. Acad. Sci. U.S.A. 42:571–574) fortuitously provided sufficient quantities of NGF to permit studies relating to the physiology, protein chemistry, and, more recently, the molecular biology of NGF (i.e. molecular cloning of NGF and its receptor). The function of large amounts of NGF in the adult male mouse salivary gland remains unknown; however, it appears that this abundant source of NGF may not play any role in development or maintenance of the peripheral or central nervous system. In target tissues innervated by NGF sensitive neurons (neurons which have been shown to depend on NGF for survival, to possess high affinity NGF receptors and to internalize and retrogradely transport NGF with high specificity), the steady state of measurable levels of NGF have been found to be extremely low, in the range of picograms or nanograms per gram of tissue, compared to thousand-fold higher levels in adult male mouse salivary gland tissue. NGF has not been found at any appreciable level in serum and therefore does not appear to be a circulating growth factor or hormone (Suda et al., 1978, Proc. Natl. Acad. Sci. U.S.A. 75:4042–4046).

In addition to the important discovery of a major source of NGF protein in the mouse submandibular gland, the development of sensitive, reliable and efficient biological assays has played a major role in elucidating the biology and biochemistry of NGF. Dorsal root ganglia (DRG) of the developing chick embryo were one of the first neuronal types to be shown to be responsive to NGF in vitro. Explant cultures of E8-E12 chick DRG in a plasma clot, and, more recently, dissociated neuron-enriched cultures of chick DRG have proven very useful in bioassays for NGF activity (e.g. during purification) and for in vitro studies of NGF biology (Levi-Montalcini et al., 1954, Cancer Res. 4:49-57; Levi-Montalcini and Angeletti, 1963, Develop. Biol. 1:653-659; Greene, 1977, Develop. Biol. 58:96, ibid 58:106). The fact that more than forty DRG can be dissected from a single chick embryo has led to the widespread use of NGF bioassays in many laboratories.

In addition to the availability of large quantities of NGF protein and efficient NGF assay systems, a third major factor which has greatly contributed to our understanding of the biology of NGF is the relative ease with which antibodies to NGF can be raised in guinea pigs, rabbits, sheep, etc.; it appears that mouse NGF is highly immunogenic. Cohen (1960, Proc. Natl. Acad. Sci. U.S.A. 46:302-311) raised antibodies to the NGF he had purified from mouse submandibular gland and showed, with Levi-Montalcini and Booker (1960, Proc. Natl. Acad. Sci. U.S.A. 46:384-391) that these antibodies caused destruction of sympathetic ganglia, or "immunosympathectomy," when administered daily to newborn rats (Levi-Montalcini and Angeletti, 1966, Pharmacol. Rev. 18:619-628).

The abundance of NGF protein allowed the primary sequence to be determined by relatively conventional protein chemistry (Angeletti and Bradshaw, 1971, Proc. Natl. Acad. Sci. 68:2417-2420). The NGF gene has now been cloned from many species, including mouse (Scott et al., 1983, Nature 302:538-540), human (Ullrich et al., 1983, Nature 303:821-825), cow and chick (Meier et al., 1986, EMBO J. 5:1489-1493), and rat (Whittemore et al., 1988, J. Neurosci. Res., 20:402-410) using essentially conventional molecular biology based on the availability of the protein sequence of mouse NGF to design suitable oligonucleotide probes. The availability of abundant NGF has also greatly facilitated studies on the NGF receptor, which have ultimately led to the molecular cloning of the NGF receptor from human and rat (Johnson et al., 1986, Cell, 47:545-554; Radeke et al., 1987, Nature 325:593-597).

It is now well established that NGF is not a ubiquitous neurotrophic factor. Within the peripheral nervous system, NGF appears not to be a survival factor for parasympathetic neurons, neural placode-derived sensory neurons or enteric neurons, as determined both from studies in vitro and in vivo. Furthermore, NGF does not appear to be a survival factor for developing motorneurons (Oppenheim, 1982, J. Comp. Neurol. 210:174-189), although these neurons do appear to express at least a low affinity form of the NGF receptor during development (Raivich et al., 1985, EMBO J. 4:637-644). The lack of effects of NGF on these neuronal types has prompted the search for other neurotrophic factors, especially factors that would sustain the survival of spinal cord motorneurons and/or parasympathetic neurons of the ciliary ganglion.

2.3. Other Neurotrophic Factors

In the past decade there have been numerous reports of neurotrophic activity in extracts of a great variety of tissues and in the conditioned culture medium of many different cell types. In almost all cases, however, progress in purifying and characterizing these activities has been hampered by the fact that such activities are present in extremely small amounts, in the range of picograms to nanograms per gram of tissue.

Furthermore, whereas adequate bioassays have been established for peripheral neurons, designing reliable, reproducible and specific assays for central nervous system neurons has proved problematic. While individual types of peripheral neurons are found as discrete, easily dissectable ganglia, central nervous system (CNS) neurons are invariably highly heterogenous in their distribution. Thus, specific markers are required for either identification or enrichment of particular classes of CNS neurons. Progress in producing such markers, for example, antibodies directed toward cell surface or cytoskeletal components, or specific histological stains, has been very limited. Accordingly, characterization of neurotrophic factors which are (i) not as abundant as NGF, (ii) difficult to assay, and (iii) not available in sufficient quantities to elicit antibody production, has proved to be an exceedingly difficult process.

2.3.1. Comparison of a Brain Derived Neurotrophic Factor (BDNF) and Nerve Growth Factor Neurotrophic activity capable of sustaining the survival of embryonic chick dorsal root ganglion neurons in vitro was identified in the "conditioned medium" in which rat C-6 glioma cells had been cultured (Barde et al., 1978, Nature 274:818). The activity was not neutralized by antibodies to mouse NGF, suggesting the presence of another neurotrophic factor in the conditioned medium. Similar activities that could not be blocked by NGF antibodies were subsequently reported in cultures of normal adult rat brain astroglial cells (Lindsay, 1979, Nature 282:80-82; Lindsay et al., 1982, Brain Res. 243:329-343) and in extracts of developing and adult rat brain (Barde et al., 1980, Proc. Natl. Acad. Sci. U.S.A. 77:1199-1203) and developing and mature chick spinal cord (Lindsay and Peters, 1984, Neurosci. 12:45-51). However, in no case was the active factor(s) isolated or identified, and it remains questionable as to whether the observed activities were due to the same or different factor(s).

Using pig brain as a starting material, Barde et al. (1982, EMBO J. 1:549-553) reported a factor, now termed brain-derived neurotrophic factor (BDNF), which appeared to promote the survival of dorsal root ganglion neurons from E10/E11 chick embryos. The neurotrophic activity was found to reside in a highly basic protein (isoelectric point, $pI > 10.1$) which migrated during sodium dodecyl sulfate (SDS) gel electrophoresis as a single band of 12.3 kD molecular weight. The purification factor was estimated to be $1.4 \times 10^6$, but the yield was very low, with only approximately 1 µg of BDNF purified from 1.5 kg of pig brain. Furthermore, because the last step in the purification process was preparative gel electrophoresis, the activity of BDNF could not be fully renatured secondary to the presence of residual SDS (Barde and Thoenen, 1985, in "Hormones and Cell Regulation," Vol. 9, Dumont et al., eds. Elsevier Science Publishers, pp. 385-390). It was noted that the highly basic nature and molecular size of BDNF were very similar to the NGF monomer. However, BDNF appeared to have properties that differed from the known properties of NGF in that (a) in the chick dorsal root ganglion bioassay, antibodies to NGF had no apparent effect on the biological activity of BDNF; (b) the effects of BDNF and NGF appeared to be additive; and (c) unlike NGF, BDNF was found to have no effect on the survival of E12 chick sympathetic neurons. In addition, during early studies with brain extracts, it was observed that the neurotrophic activity in these sources appeared to act upon sensory neurons at later stages of development than were associated with NGF. Using dissociated cultures of chick embryo neurons cultured on a polycationic substrate such as polylysine or polyornithine, BDNF was found to support the survival of more than 30 percent of E10-11 (embryonic day ten or eleven) dorsal root ganglion neurons but seemed to have little effect on the survival of the same neurons at E6 (Barde et al., 1980, Proc. Natl. Acad. U.S.A. 77:1199-1203 supra). Under similar conditions, NGF supported the survival of 30-40 percent of E6 DRG neurons. Interestingly, it was later found that when cultured on a substrate coated with the extracellular matrix glycoprotein laminin, both NGF and BDNF supported the survival of about 50 percent of DRG neurons from chick embryos of ages E6-E12 (Lindsay et al., 1985, Develop. Biol. 112:319-328). In the latter study, the effects of NGF and BDNF were found to be additive when both were present at saturating concentrations.

Early studies by Levi-Montalcini (1966, The Harvey Lectures 60:217-259) on the neuronal specificity of NGF suggested that NGF was not a ubiquitous neurotrophic factor even for sensory neurons, as NGF appeared to have no effect upon neurons of certain cranial sensory ganglia of the chick, especially the nodose ganglion of the tenth cranial nerve. Later in vivo studies (Johnson et al., 1980, Science 210:916-918; Pearson et al., 1983 Develop. Biol. 96:32-36) showed that NGF deprivation during embryogenesis had no effect on the survival of neurons in most cranial sensory ganglia of the rat, while similar treatment greatly depleted the neuronal count in sensory ganglia derived from the neural crest. More detailed in vitro studies (Lindsay and Rohrer, 1985, Develop. Biol. 112:30-48; Davies and Lindsay, 1985, Develop. Biol. 111:62-72; Lindsay et al., 1985, J. Cell. Sci. Suppl. 3:115-129) clearly indicated that NGF supports the survival of most neural crest-derived sensory neurons but has no apparent effect on the survival of cranial sensory neurons derived from neural placodes.

The first demonstration of a neuronal specificity of BDNF distinct from that of NGF was the demonstration in vitro that purified BDNF supports the survival of 40-50% of sensory neurons dissociated from the neural placode-derived nodose ganglion of the chick embryo at E6, E9 or E12 (Lindsay et al., 1985, J. Cell. Sci. Supp. 3:115-129). NGF was without apparent effect on these neurons either by itself or in conjunction with BDNF. It was later shown in explant culture studies that BDNF appeared to support survival and neurite outgrowth from other neural placode-derived sensory ganglia, including the petrosal, geniculate and ventrolateral trigeminal ganglia (Davies et al., 1986, J. Neurosci. 6:1897-1904), none of which have been found to be sensitive to NGF. In all of the above studies antibodies to NGF had no effect upon the observed activity of BDNF. In addition to its effects on cultured neurons from peripheral ganglia, BDNF was found to stimulate survival and neuronal differentiation of cells cultured from quail neural crest (Kalcheim and Gendreau, 1988, Develop. Brain Res. 41:79-86).

Prior to the instant invention, the inability to produce sufficient amounts of BDNF for immunization prevented the production of anti-BDNF antibodies for comparison to anti-NGF antibodies in their effects on neuronal populations, and precluded BDNF/NGF cross-neutralization experiments. Two recent studies with BDNF (Kalcheim et al., 1987, EMBO J. 6:2871-2873; Hofer and Barde, 1988, Nature 331:261-262) have, however, indicated a physiological role of BDNF in avian PNS development. If a mechanical barrier was placed in ovo between E3/E4 DRG (embryonic day 3 or 4 dorsal root ganglia) and their CNS target in the neural tube, many DRG neurons were observed to die (Kalcheim and Le Douarin, 1986, Develop. Biol. 116:451-466). It Was postulated that this neuronal death may have been due to deprivation from a CNS (neural tube) derived neurotrophic factor. It was subsequently observed that BDNF attached to a laminin-coated sialastic membrane could prevent this cell death (Kalcheim et al., 1987, EMBO J. 6:2871-2873). Injections of BDNF into developing quail eggs has been found to reduce naturally occurring cell death in the nodose ganglia, an effect not seen with NGF (Hofer and Barde, 1988, Nature 331:261-262). In addition to its effect on peripheral) sensory neurons of both neural crest and neural placode origin, BDNF was found to support the survival of developing CNS neurons. Johnson et al. (1986, J. Neurosci. 6:3031-3938) presents data that indicates that BDNF supports the survival of retinal ganglion cells cultured from E17 rat embryos. This was in agreement with previous studies which showed that conditioned media and brain extracts prepared from the target regions of retinal ganglion cells appeared to support the survival of these neurons (McCaffery et al., 1982, Ex. Brain Res. 48:37-386; Sarthy et al., 1983, J. Neurosci. 3:2532-2544; Turner et al., 1983, Dev. Brain Res. 6:77-83).

In addition to its effects on the survival of developing neurons in culture, BDNF has been shown to have effects on cultured adult peripheral and central nervous system neurons. BDNF, as well as NGF, has been shown to stimulate axonal regeneration from adult rat DRG neurons in culture (Lindsay, 1988, J. Neurosci. 8:2394-2405) although adult sensory neurons did not appear to require neurotrophic factors for maintenance in vitro over 3 or 4 weeks. Furthermore, in cultures of adult rat retina, BDNF was observed to promote both survival and axonal elongation from retinal ganglion cells (Thanos et al., 1989, Eur. J. Neurosci. 1:19-26). A comparison of the biological effects of NGF and BDNF is presented in Table I.

TABLE I

COMPARISON OF BIOLOGICAL ACTIVITIES OF BDNF AND NGF*

|  |  | SURVIVAL** | |
|---|---|---|---|
|  |  | BDNF | NGF |
| PERIPHERAL NERVOUS SYSTEM | | | |
| (i) | E6 Chick DRG | − | ++ |
|  | E10 Chick DRG | − | ++ |
|  | E12 Chick Symp | − | ++ |
| (ii) | E6-E12 Chick DRG | ++ | ++ |
|  | E6-E12 Chick Nodose | ++ | − |
|  | E12 - Chick Sympathetic | − | ++ |
|  | E12 - Chick ciliary | − | − |
|  | (Lindsay et al., 1985, supra) | | |
| (iii) | E3-E14 Chick: | | |
|  | Jugular | +/++ | ++ |
|  | DM-trigeminal | +/++ | ++ |
|  | Petrosal | +/++ | − |

TABLE I-continued

COMPARISON OF BIOLOGICAL ACTIVITIES OF BDNF AND NGF*

| | SURVIVAL** | |
|---|---|---|
| | BDNF | NGF |
| Geniculate | +/++ | — |
| VL-trigeminal | ++ | — |
| Vestibular | — | — |
| Mesencephalic | ++ | — |
| (Davies et al., 1986, supra) | | |
| (Barde et al., 1987, Prog. Brain Res., 71:185-189) | | |
| CENTRAL NERVOUS SYSTEM | | |
| (i) E17 Rat Retinal Ganglion Cells (Johnson et al., 1986, J. Neurosci. 63031-3038) | ++ | — |

*in chronological order according to publication date; effects tested in vitro
**no survival: (—); moderate survival (+); good survival (++)

2.3.2. Neuronal Targets of Brain Derived Neurotrophic Factor

Sensory neurons of peripheral nerve ganglia have been found to arise from either of two distinct, transient embryological structures, namely, the neural crest and neural placodes. The neural crest appears to give rise to both neurons and satellite cells of autonomic ganglia and spinal nerve sensory ganglia, i.e. DRG. The contribution of the neural crest and neural placodes to the formation of cranial nerve sensory ganglia has been studied using the quail/chick chimera transplantation system devised by Le Douarin (Le Douarin, 1973, Develop. Biol. 20:217-222; Noden, 1978, Develop. Biol. 67:313-329; Narayanan and Narayanan, 1980, Anat. Rec. 196:71-82; Ayer-Le Lievre and Le Douarin, 1982, Develop. Biol. 94:291-310; D'Amico-Maratel and Nodem, 1983, Am. J. Anat. 166:445-468). As reviewed in Lindsay et al. (1985, J. Cell. Sci. Supp. 3:115-129), it is now believed, at least for birds, that neurons of the distal ganglia of the VIIth, IXth, and Xth cranial nerves (geniculate, petrosal and nodose ganglia, respectively) and neurons of the vestibuloacoustic complex of the VIIIth cranial nerve are exclusively of neural placode origin. The trigeminal ganglion of the Vth cranial nerve contains neurons of both crest and placode origin (with the placode-derived neurons predominant in the ventrolateral pole of the maxillo-mandibular lobe) whereas the satellite cells of all cranial ganglia have been found to be entirely of neural crest origin.

From in vitro experiments using both explant and dissociated, neuron-enriched cultures of spinal and cranial nerve sensory neurons, it has been found that sensory neurons of neural crest origin are responsive to NGF; in contrast, neurons derived from neural placodes (including neurons of the ventrolateral portion of the trigeminal ganglion and the entire neuronal population of the vestibular, geniculate, petrosal and nodose ganglia) have been observed to be largely unresponsive to NGF throughout embryonic development. In contrast to differences in their requirement and responsiveness to NGF, both placode and neural crest derived sensory neurons have been found (Table I) to be responsive to the survival and neurite-promoting activity of BDNF (Lindsay et al., 1985, J. Cell. Sci. Supp. 3:115-129; Lindsay et al., 1985, Develop. Biol. 112:319-328 Kalcheim and Gendreau, 1988, Develop. Brain Res. 41:79-86). Tebar and Barde (1988, J. Neurosci. 8:3337-3342) studied the binding parameters of radioactively labeled BDNF to chick embryo dorsal root ganglion neurons; their results are consistent with the existence of two classes of BDNF receptors, one with high affinity for BDNF, the other with low affinity. No high affinity receptors were observed on sympathetic neurons.

The known neuronal targets of BDNF were further reviewed by Barde et al. (1987, Prog. Brain Res. 71:185-189). Prior to the instant invention, identification of cells synthesizing BDNF has not been feasible due to the lack of nucleic acid or antibody probes specific for BDNF. Attempts to prepare either polyclonal or monoclonal antibodies to BDNF have been unsuccessful. This failure to raise antibodies had hindered the molecular cloning of BDNF, determination of the physiological effect of depriving developing neurons of BDNF in vivo, quantitation of BDNF in tissues using an immunoassay, and localization of BDNF using immunocytochemistry.

TABLE II

SUMMARY OF BDNF RESPONSIVE AND NON-RESPONSIVE NEURONS*

| A. | Responsive Neurons | |
|---|---|---|
| | I. | Chick sensory neurons of neural crest origin in: |
| | | (a) dorsal root ganglion |
| | | (b) jugular ganglion |
| | | (c) dorsomedial trigeminal ganglion |
| | | (d) mesencephalic trigeminal nucleus** |
| | II. | Chick sensory neurons of ectodermal placode origin in: |
| | | (a) nodose ganglion |
| | | (b) vestibular ganglion |
| | | (c) petrosal ganglion |
| | | (d) geniculate ganglion |
| | | (e) ventrolateral trigeminal ganglion |
| | III. | Rat retinal ganglion cells |
| B. | Non-Responsive Neurons | |
| | I. | Chick and rat sympathetic neurons |
| | II. | Chick parasympathetic ciliary neurons |

*From Barde et al., 1987, Prog. Brain Res. 71:185-189
**See Davies et al., 1986, Nature 319:497-499

3. SUMMARY OF THE INVENTION

The present invention relates to nucleic acid sequences encoding brain derived neurotrophic factor (BDNF), to the substantially pure protein, peptide fragments or derivatives produced in quantity therefrom, and to antibodies directed toward BDNF protein, peptide fragments, or derivatives. The present invention makes available, for the first time, sufficient quantities of BDNF to enable anti-BDNF antibody production and to support diagnostic and therapeutic applications of BDNF.

In various embodiments of the invention, the BDNF nucleic acids, proteins, peptides, derivatives, or antibodies of the invention may be utilized in methods for the diagnosis and treatment of a variety of neurologic diseases and disorders, and, in particular, in the diagnosis and treatment of sensory neuron disorders and retinal degeneration. Furthermore, in specific embodiments of the invention, BDNF nucleic acids or BDNF gene products may be used in the diagnosis and treatment of neuroblastoma tumor, Parkinson's disease, and Alzheimer's disease. BDNF gene products may also be used to facilitate incorporation of implants into nervous tissue or, alternatively, to promote nerve regeneration following damage by trauma, infarction, infection, or postoperatively, in additional specific embodiments of the invention.

The invention also relates to pharmaceutical compositions comprising effective amounts of BDNF gene products or, alternatively, antibodies directed toward BDNF gene products, which may be utilized in the diagnosis or treatment of a variety of neurological diseases and disorders.

In addition, by providing the full nucleotide sequence of BDNF, the present invention allows for the comparison of BDNF and NGF genes, thereby identifying homologous regions and defining a BDNF/NGF gene family. Accordingly, the present invention relates to a method for identifying additional members of the BDNF/NGF gene family. In a specific embodiment, the method of the invention is used to identify a novel, non-NGF, non-BDNF member of the BDNF/NGF gene family. The invention further provides for additional members of the BDNF/NGF gene family identified according to the disclosed method and to their gene products.

3.1. Abbreviations and Definitions

BDNF: brain derived neurotrophic factor
CAT: choline acetyltransferase
CNS: central nervous system
DRG: dorsal root ganglia (ganglion)
EDTA: ethylene diamine tetraacetic acid
NGF: nerve growth factor
PBS: phosphate buffered saline
PCR: polymerase chain reaction
PNS: peripheral nervous system
SDS: sodium dodecyl sulfate
Tris: tris(hydroxymethyl)aminomethane

4. DESCRIPTION OF THE FIGURES

FIG. 1. Nucleotide sequence and deduced amino-acid sequence of porcine prepro BDNF cDNA. The complete sequence of two overlapping cDNA clones is shown in this figure. The peptide sequences obtained from microsequencing (Table III) are underlined. The only consensus sequence for N-glycosylation is double underlined. The start of the mature BDNF sequence is marked by a double carat.

FIG. 2. Sequence comparison between NGF and BDNF. Areas with more than two amino acids found at identical positions are indicated. The sequences start with the first amino acids of the mature proteins and end with the last ones before the stop codons. Fifty-one amino acids are common to BDNF and the various NGFs (Schwarz et al., 1989, J. Neurochem. 52:1203-1209), including the 6 cysteine residues.

FIG. 3. Autoradiograph of Southern blots of EcoRI cut human, monkey, rat, mouse, dog, cow, rabbit, chicken, and yeast genomic DNA, hybridized to $^{32}$P-labeled NGF and BDNF probes.

Figure 4:
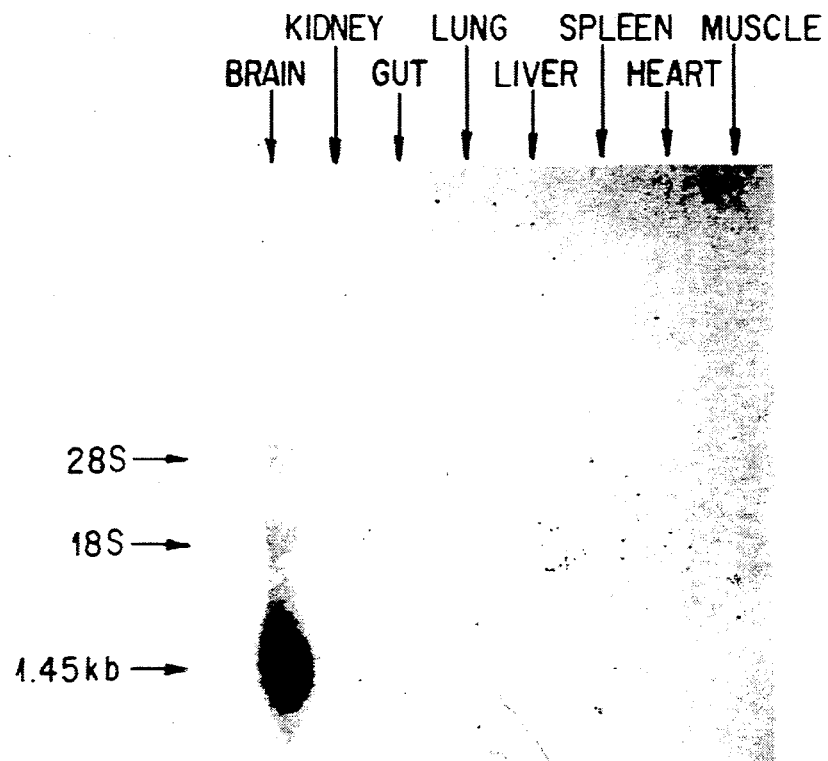

FIG. 4. Northern blot analysis. From each tissue, 20 µg total RNA was applied per lane and hybridized with a $^{32}$P-labeled cRNA mouse BDNF probe. Note that a strong signal can be seen at about 1.45 kB with brain tissue, but none with the 7 other tissues analyzed.

FIGS. 5A-5I. Sequence of human BDNF cDNA and deduced amino acid sequence, and comparison of DNA sequences from pig, rat, and chicken.

Figure 6:
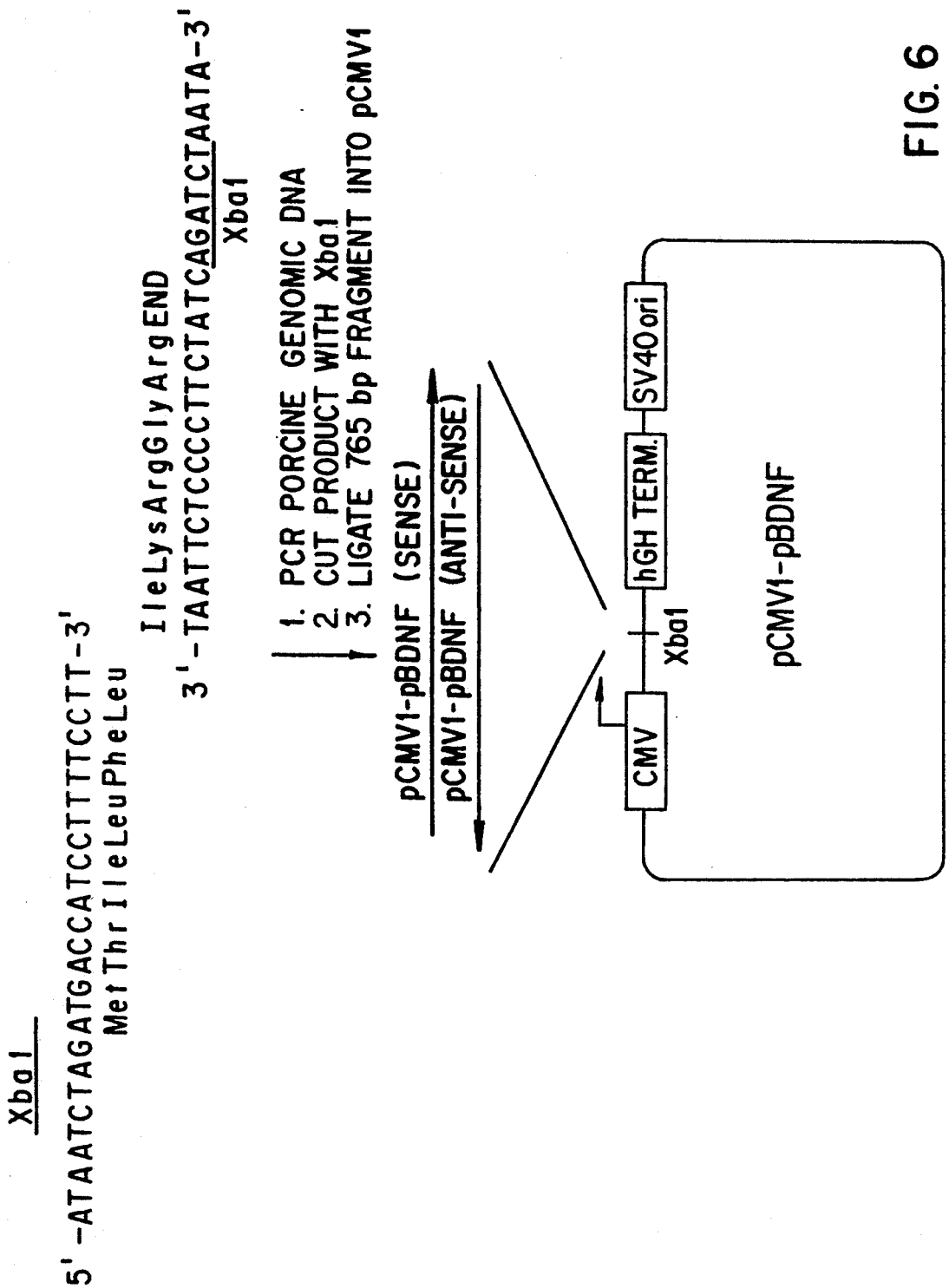

FIG. 6. BDNF expression plasmid PCMV1-pBDNF.

Figure 7A:
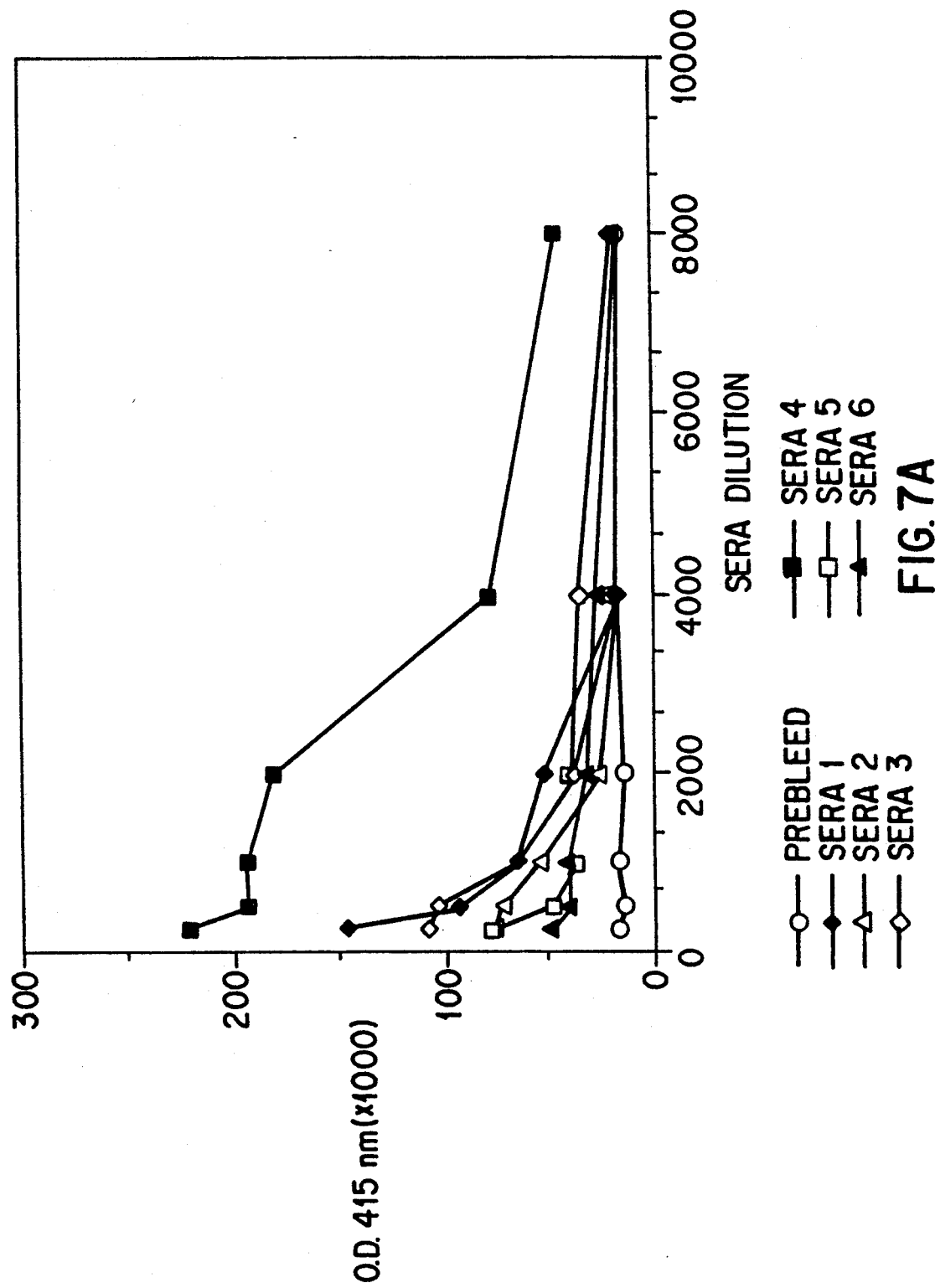

FIG. 7A. Results of ELISA determination of binding of antisera to B5 peptide, using serial dilutions of antisera.

Figure 7B:
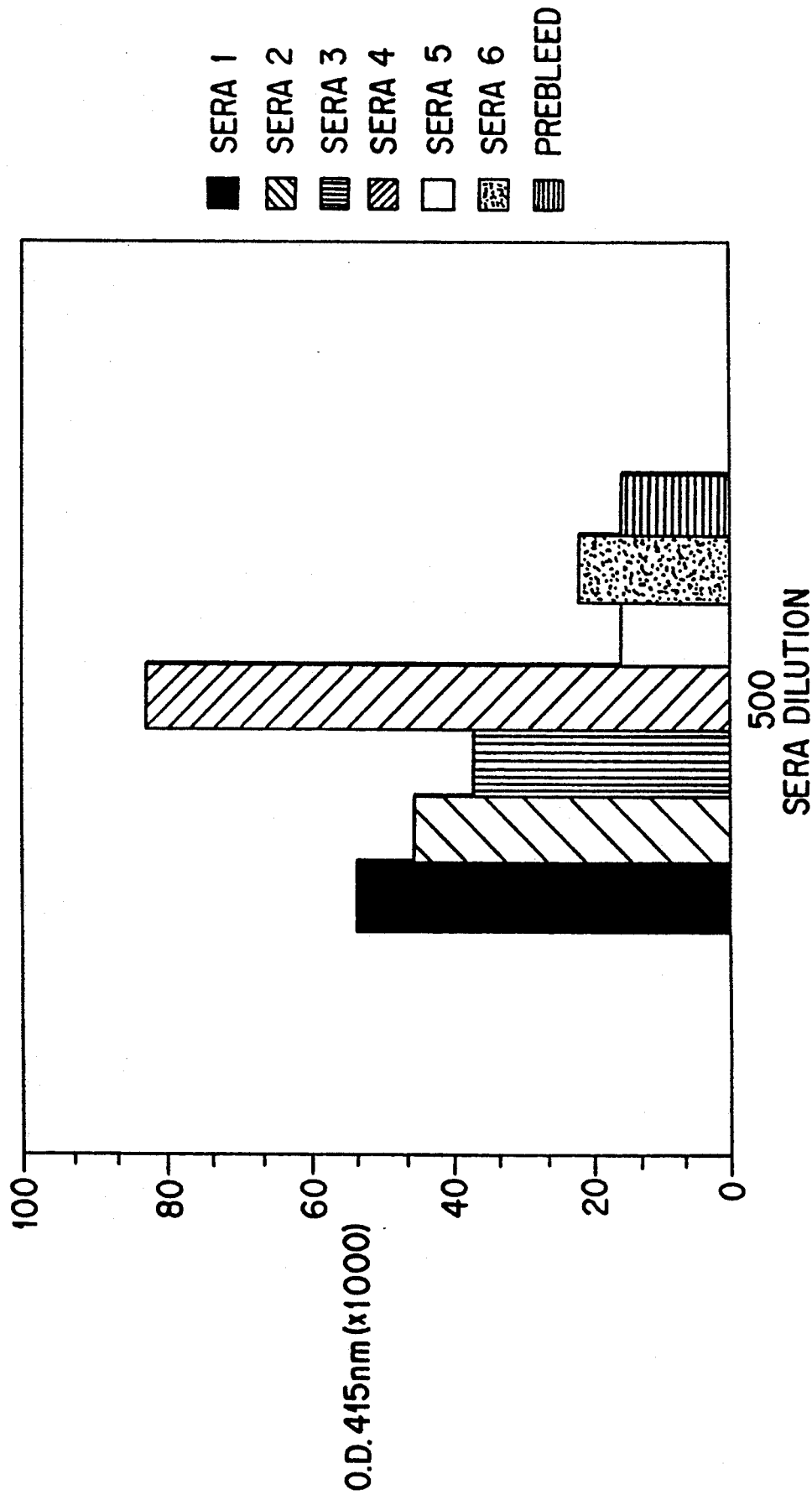

FIG. 7B. Quantitation of binding of 1:500 dilution of various antisera to 50 ng BDNF.

Figure 8:
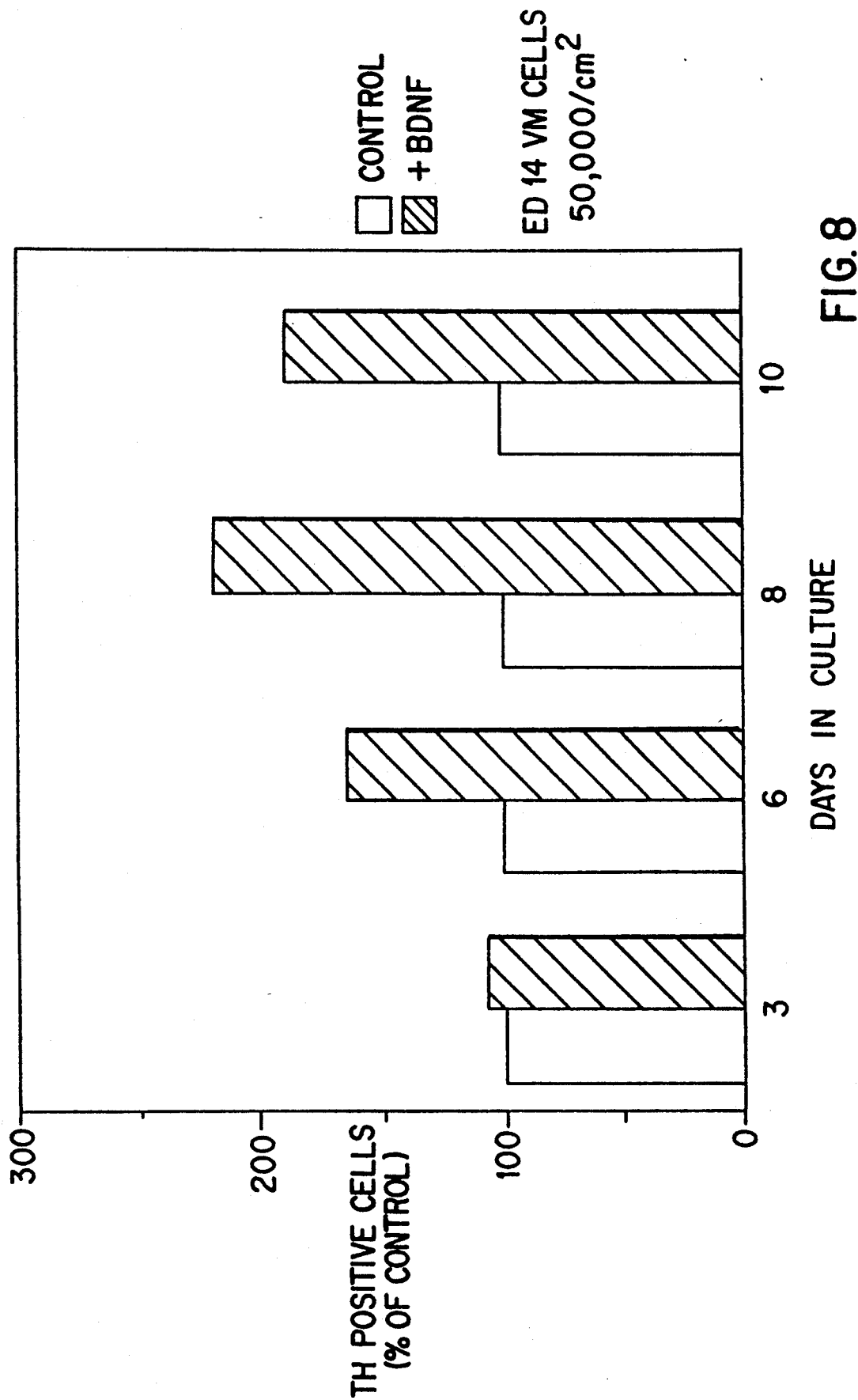

FIG. 8. Results of immunohistochemical staining for tyrosine hydroxylase in BDNF-treated (hatched bars) and control (solid bars) ventral mesencephalon cultures.

FIG. 9. Dopamine uptake by ventral mesencephalon cultures. Cultures supplemented with BDNF are denoted by hatched bars; control cultures are represented by solid bars.

FIG. 10A. The effect of BDNF on the number of CAT positive cells in forebrain cholinergic neuron cultures.

Figure 10B:
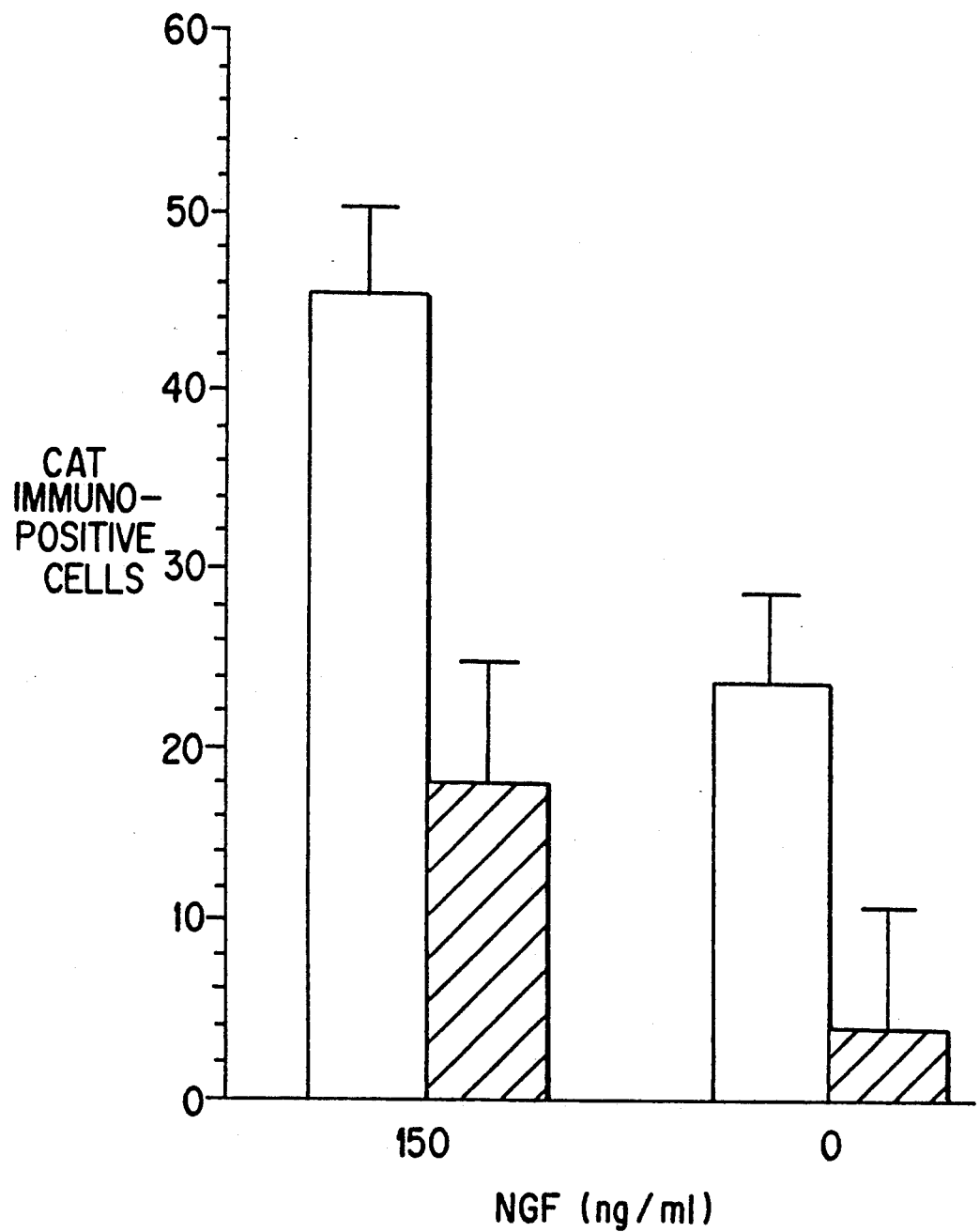

FIG. 10B. Forebrain cholinergic neuron cultures, at densities of 260,000 cells per well (black bar) or 150,000 cells per well (hatched bar), were treated with 150 ng/ml of NGF. The number of CAT immunopositive cells in NGF-treated versus untreated cells was compared.

Figure 11:
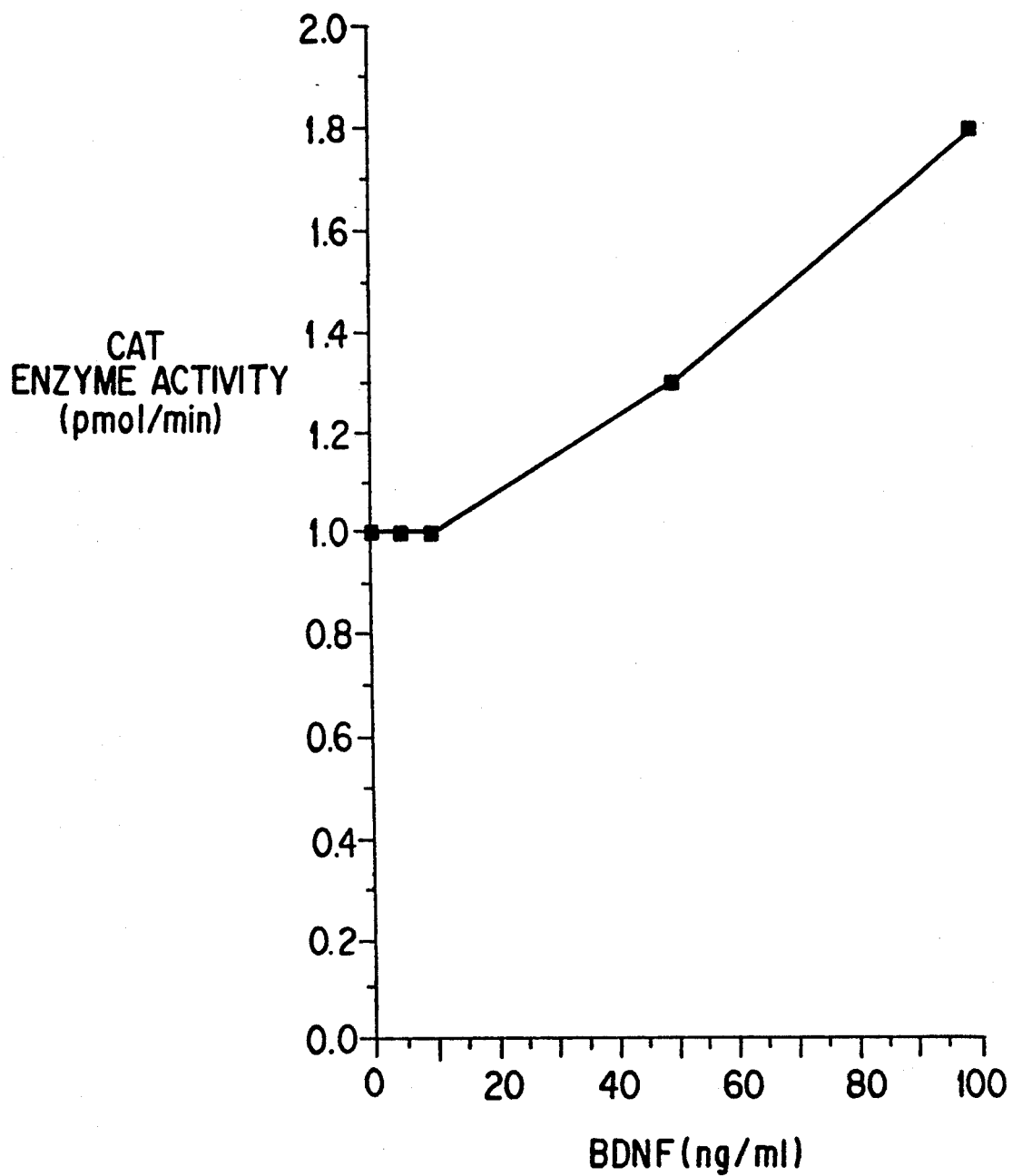

FIG. 11. Changes in the amount of CAT enzyme activity, in picomoles of substrate catalyzed per minute, as a function of BDNF concentration in forebrain cholinergic neuron cultures.

Figure 12A:
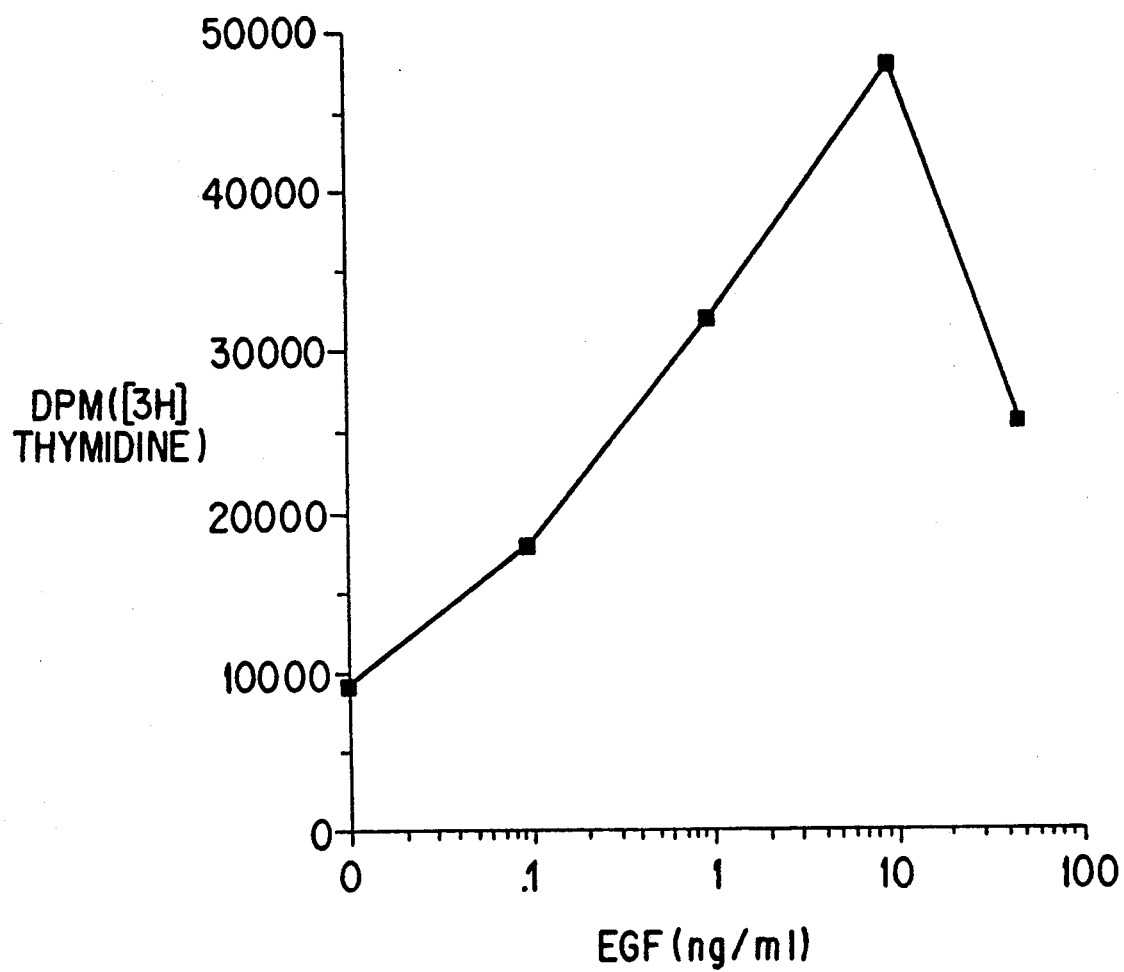

FIG. 12A. Astroglial cell cultures, at approximately 60% confluency, were treated with epidermal growth factor for 42 hours, then incubated with [$^3$H] methylthymidine. Amount of $^3$H incorporated was measured relative to EGF concentration.

FIG. 12B. Astroglial cell cultures, at approximately 60% confluency, were treated with BDNF for 42 hours, then incubated with [$^3$H] methylthymidine. Amount of $^3$H incorporated was measured relative to BDNF concentration.

Figure 13:
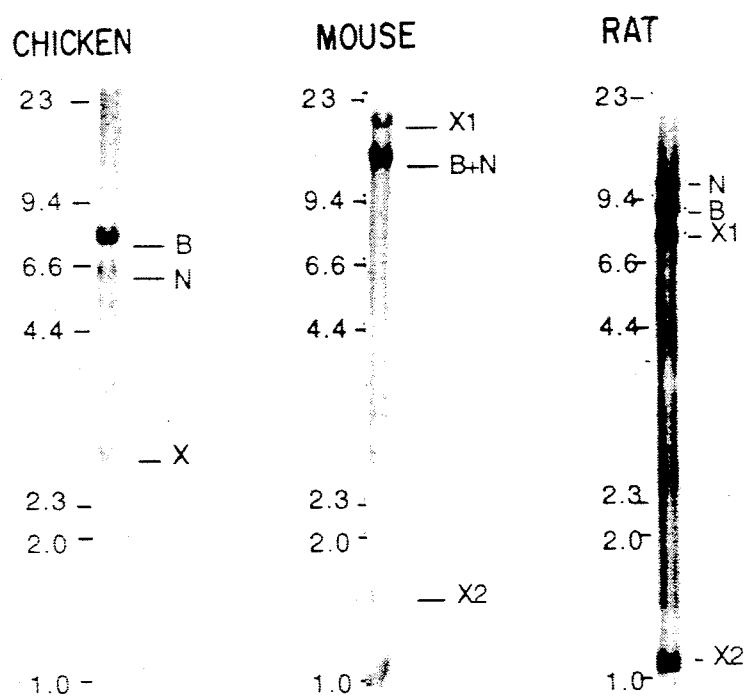

FIG. 13. Southern blot of EcoRI restricted chicken, mouse, rat, hybridized to BDNF/NGF probe R1B/2C. The positions of the NGF and BDNF genomic EcoRI fragments are indicated as N and B, respectively.

FIG. 14. Sequence comparison of NGF and BDNF with novel member of BDNF/LNGF family identified by PCR from mouse DNA with Box 3/Box 4 primers: Novel gene [designated here as M3/4(showing sequence of coding strand only, and deduced amino acid sequence aligned relative to mature mouse NGF and mature pig, rat, mouse, or human BDNF. Dashes indicate a position where a deletion of one codon in NGF is used to optimize alignment relative to BDNF and M3/4. Italics indicate matches in amino acid sequence and/or conservative amino acid substitutions).

FIG. 15. Northern blots of RNA from a variety of human tumor derived cell lines hydbridized to BDNF human probe.

5. DETAILED DESCRIPTION OF THE INVENTION

The present invention relates to nucleic acid sequences encoding brain derived neurotrophic factor (BDNF), as well as BDNF protein, peptide fragments and derivatives produced in quantity using these nucleic acid sequences. In addition, the invention relates to pharmacologic compositions and therapeutic uses of BDNF, having provided, for the first time, the means to generate sufficient quantities of substantially pure BDNF for clinical use. The invention also relates to antibodies directed toward BDNF or fragments thereof, having provided a method for generating sufficient immunogen. Further, by permitting a comparison of the nucleic acid sequences of BDNF and NGF, the present invention provides for the identification of homologous regions of nucleic acid sequence between BDNF and NGF, thereby defining a BDNF/NGF gene family; the invention provides a method for identifying and isolating additional members of this gene family.

For purposes of clarity of description, and not by way of limitation, the invention will be described in the following parts:
(i) purification of BDNF
(ii) BDNF bioassays
(iii) microsequencing of BDNF protein
(iv) cloning of BDNF encoding DNA
(v) expression of BDNF
(vi) BDNF genes and proteins
(vii) generation of anti-BDNF antibodies
(viii) identification of additional members of the BDNF/NGF gene family
(ix) utility of the invention
(x) pharmaceutical compositions

5.1. Purification of Brain Derived Neurotrophic Factor

In order to identify BDNF encoding nucleic acid, microgram amounts of BDNF protein may be obtained from tissue to permit the determination of amino acid sequences which may then be used to design oligonucleotide probes. The extreme rarity of BDNF protein practically limits the amount of amino acid sequence which may be determined. BDNF may be prepared from pig brain by methods described in Barde et al., (1982, EMBO J. 1:549-553), or Hofer and Barde (1988, Nature 331:261-262).

Preferably, BDNF may be prepared, according to the following detailed protocol which is presented by way of example, and not by way of limitation; various modifications are envisioned for use by one skilled in the art. Because of the rarity of BDNF, preferably about six kilograms of brain tissue may be used in a purification procedure. Brain tissue may be homogenized in sodium phosphate buffer at a concentration of about 0.2M sodium phosphate and a pH of approximately 6, containing 1 mM EDTA and 1 mM freshly added phenylmethanesulphonyl fluoride, such that the ratio of brain tissue to fluid is approximately 1 kg of brain to 2 liters of buffer. Hydrochloric acid may then be used to adjust the pH of the mixture to approximately 4, and the mixture may then be stirred for about 2 hours at 4° C. The mixture can then be centrifuged for 25 minutes at 20,000 g. After centrifugation, the supernatant is collected, adjusted to a pH of about 6.0 using sodium hydroxide, and then stirred with about 1 liter of preswollen carboxymethylcellulose (per 6 kg of brain tissue) which has been equilibrated with 0.1M sodium phosphate at a pH of 6. After several washes with a total of about 20 liters of 0.1M sodium phosphate, pH 6, the slurry may be poured into a column and washed with the same buffer containing 0.13M NaCl, preferably overnight. Active fractions, identified by a BDNF sensitive bioassay (see Section 5.2, infra) may then be eluted with phosphate buffer containing 0.5M NaCl and subsequently dialyzed against several changes of about 5 liters of 5 mM potassium phosphate at a pH of 6.8. The dialyzed fractions may then be applied to a hydroxyapatite column having a bed volume of about 20 ml for each kilogram of brain tissue processed; the hydroxyapatite column should be pre-equilibrated with 5 mM potassium phosphate at a pH of 6.8 prior to application of sample. The column may then be eluted with a linear gradient composed of 500 ml of 5 mM potassium phosphate and 500 ml of 700 mM potassium phosphate, both at a pH of about 6.8. The BDNF activity should optimally be eluted at approximately 500 mM potassium phosphate. Pooled active fractions may then be adjusted to a final molarity of about 700 mM potassium phosphate and applied to a phenyl-sepharose column (having a volume of about 5 ml for every 6 kg of brain tissue processed) equilibrated with a solution of 700 mM potassium phosphate having a pH of 6.8. After washing with approximately 40 ml of the same buffer, BDNF activity may be eluted with 0.1M potassium phosphate, pH 6.8, and subsequently the BDNF activity may be dialyzed against distilled water, and then lyophilized. The lyophilized material may then be taken up in an SDS-gel electrophoresis sample buffer containing 0.1% SDS but preferably containing no mercaptoethanol, and applied to an SDS gel comprised of a linear gradient of 10-25% acrylamide. After completion of electrophoretic separation, the gel may be stained for about 10 minutes with Coomassie blue, and destained for about 20 minutes. A band migrating at the level of a cytochrome c marker may be cut out and electrophoretically eluted from the gel. SDS may be largely removed as described by Weber and Kuter (1971, J. Biol. Chem. 246:4504-4509). It should be noted that removal of SDS is generally not complete.

5.2. Brain Derived Neurotrophic Factor Bioassays

Any system which qualitatively or quantitatively indicates BDNF activity may be used according to the present invention. Such bioassays may be useful in identifying and/or measuring natural or recombinant BDNF activity.

Any BDNF bioassay known in the art may be used. For example, chick embryo dorsal root ganglion (DRG) neurons may be utilized in a BDNF assay, as described in Barde et al. (1980, Proc. Natl. Acad. Sci. U.S.A. 77:1199-1203).

By way of example, dorsal root ganglia from 6 to 14 day chick embryos, and preferably 10 to 12 day chick embryos, may be collected, using dissection techniques known in the art, and immediately placed in a small volume of F14 medium (made from GIBCO F-12 powder, supplemented as in Vogel et al., 1972, Proc. Natl. Acad. Sci. U.S.A. 69:3180-3184), which should be replaced at the end of the dissection by $Ca^{2+}$ and $Mg^{2+}$-free phosphate buffered saline (PBS) containing 0.1 percent trypsin. After about 20 minutes of incubation at 37° C., the ganglia may be centrifuged and washed twice with F14 medium containing about 10 percent (vol/vol) heat-inactivated horse serum. The ganglia may then be dissociated by gentle trituration (about 10-15 aspirations) using a small (about 1 mm) diameter siliconized pasteur pipette. Remaining lumps of tissue may then, preferably, be removed by passing the cell suspension through a nylon mesh, having about 40 μm sized pores. The cell suspension may then be preplated for about 210 minutes on a plastic tissue culture dish; during this period, most of the nonneuronal cells should adhere to the plastic surface, leaving a neuron-enriched cell population in suspension. Cells may then be diluted to a concentration of about $5 \times 10^3$ cells per milliliter of plating medium (preferably F14 medium supplemented with 10 percent vol/vol heat inactivated horse serum together with antibiotics) and placed in polyornithine or, preferably, polyornithine/-laminin coated tissue culture dishes (see infra).

Alternatively, and not by way of limitation, BDNF bioassays which are relatively insensitive to NGF may, in some circumstances, be preferable to systems, such as the DRG system described supra, which may, under certain conditions, respond to both BDNF and NGF. Such relatively BDNF-specific systems would include retinal ganglion cultures as well as cultures of neurons derived from neural placodes.

Perinatal retinal cells may be cultured according to the methods described in Johnson et al. (1986, J. Neurosci. 6:3031-3038). For example, retinas may be removed from perinatal animals (in the rat the term "perinatal" here refers to embryonic day 17 embryos through postnatal pups within 48 hours after birth), washed in calcium and magnesium free phosphate buffered saline (PBS), then incubated in PBS containing about 0.05% to 0.1% trypsin for approximately 15 minutes at about 37° C. After proteolytic digestion, retinas may be washed in F14 culture medium containing about 10 per cent (vol/vol) heat-inactivated horse serum (F14-HS). The retinas may then be dissociated by gentle pipetting in a small volume (about 1-10 ml) of fresh F14-HS. Undissociated tissue may be allowed to settle, and the remaining cells and medium pipetted off for culture.

Alternatively, BDNF bioassays which comprise neural placode derived cells may be used according to the invention. Embryonic cranial nerve explants of, for example, the ventrolateral portion of the trigeminal ganglion, or the vestibular, geniculate, petrosal, or nodose ganglion may be cultured in collagen-gel overlaid with culture medium, as described in Davies et al. (1986, J. Neurosci. 6:1897-1904) or dissociated according to Barde et al. (1980, Proc. Natl. Acad. Sci. 77:1199-1203).

Because it has been observed that responsiveness to BDNF may be increased ten-fold by changing the growth substrate from polyornithine to laminin-polyornithine, (Barde et al., 1987, Prog. Brain Res. 71:185-189), BDNF assays are preferably performed on laminin-containing substrates. Culture surfaces may be prepared, for example, by (i) coating the culture surface for about 8-10 hours with a sterile solution of polyornithine; (ii) washing several times with sterile water; and (iii) coating the culture surface for about two hours with laminin at a concentration of approximately 25 μg/ml in PBS (Johnson et al., 1986, J. Neurosci. 6:3031-3038).

In any bioassay system used according to the invention, a BDNF dose-response curve may be established using methods known in the art. Using a dissociated chick sensory ganglion assay, half-maximal survival was observed with a concentration of about 5 ng/ml purified BDNF, and maximal survival was observed with a concentration of between about ten and 20 ng/ml purified BDNF (Barde et al., 1987, Prog. Brain Res. 71:185-189).

5.3. Microsequencing of Brain Derived Neurotrophic Factor Protein

BDNF protein prepared from brain may be sequenced; however, it must be emphasized that the extreme rarity of the protein makes it unlikely that a substantial portion of BDNF protein sequence may be reliably obtained. The protein may be sequenced directly or initially cleaved by any protease or other compound known in the art, including, but not limited to, *Staphylococcus aureus* V8, trypsin, and cyanogen bromide. Peptides may be sequenced by automated Edman degradation on a gas phase microsequencer according to the method of Hewick et al. (1981, J. Biol. Chem. 256:7990-7997) and Hunkapillar et al. (1983, Methods Enzymol. 91:227-236). Detection of phenylthiohydantoin amino acids may then be performed according to Lottspeich (1985, Chromatography 326:321-327). Overlapping fragments of amino acid sequence may be determined and used to deduce longer stretches of contiguous sequence.

5.4. Cloning of Brain Derived Neurotrophic Factor-Encoding DNA

The rarity of BDNF effectively precludes the use of standard strategies for cloning the BDNF gene. For example, if available protein sequence were used to generate a complementary labeled oligonucleotide probe, and this probe were used to screen cDNA libraries generated from tissue presumed to synthesize BDNF, the number of positive clones would be likely to be vanishingly small. The instant invention provides for the cloning of the BDNF gene by a combination of procedures, comprising the purification of suitable amounts of BDNF protein, microsequencing of the BDNF protein, derivation of an oligonucleotide probe, construction of a cDNA library, amplification based on the derived BDNF amino acid sequence, and finally, selection for the BDNF gene. In this method of the invention, the preferred procedure for amplification utilizes the amplification of tissue nucleic acid sequences by polymerase chain reaction (PCR) (Saiki et al., 1985, Science 230:1350-1354), in order to expand the number of BDNF sequences available for cloning. A detailed description of the preferred method follows:

Firstly, the amino acid sequence derived from purified BDNF protein may be used to deduce oligonucleotide primers for use in polymerase chain reaction. Because of the degeneracy of the genetic code, in which several nucleic acid triplets may specify the same amino acid, several oligonucleotides should be synthesized for a given amino acid sequence, in order to provide for multiple potential nucleotide sequence combinations; the resulting oligonucleotides are referred to as degenerate primers.

The polymerase chain reaction (PCR) requires sense strand as well as anti-sense strand primers. Accordingly, a degenerate oligonucleotide primer corresponding to BDNF amino acid sequence may be used as primer for one DNA strand, and a second primer, homologous to a commonly occurring DNA sequence, such as a stretch of thymidine residues resulting from reverse transcription of the polyadenosine tail of mRNAs, may be used as primer for the second DNA strand. These primers may then be used in polymerase chain reaction with nucleic acid template presumed to contain BDNF encoding sequences, such as genomic DNA or, preferably, cDNA prepared from mRNA collected from tissue presumed to synthesize BDNF. The DNA reaction products may then be analyzed by electrophoresis to determine whether the DNA reaction product has a molecular size similar to the expected size of the BDNF gene and, preferably, by nucleotide sequence analysis.

However, because the use of two degenerate primers in PCR increases the likelihood of amplifying nucleic acid sequences which do not encode BDNF, a preferred method provides for the use of only one degenerate primer, the other primer corresponding to exact BDNF sequence. In order to identify exact BDNF sequence, the amino acid sequence determined using purified BDNF protein may be used to design both degenerate sense and anti-sense oligonucleotide primers. The DNA reaction product resulting from the use of these primers in PCR reaction, using BDNF encoding nucleic acid as a template, should be a nucleic acid fragment encoding the stretch of amino acids used to design the primers, and may be of a predictable size (e.g. at minimum, the number of amino acid residues, multiplied by a factor of three, base pairs in length). Sequence analysis of the DNA reaction product may be compared to the ascertained amino acid sequence to corroborate that the amplified nucleic acid sequence may, in fact, encode the BDNF peptide fragment. Although any method of nucleic acid sequencing known in the art may be utilized, it is preferable to use the dideoxynucleotide chain termination method (Sanger et al., 1979, Proc. Natl. Acad. Sci. U.S.A. 72:3918–3921). Sequencing may be accomplished using gel purified or, preferably, cloned DNA reaction product. The sequence of the DNA reaction product may then be used toward designing an oligonucleotide primer corresponding to exact BDNF-encoding sequence. This primer may then be used together with a second primer, which may be degenerate, to extend the amount of BDNF-sequence beyond that represented by the fragment of exact sequence initially determined. For example, and not by way of limitation, the sense strand primer may correspond to exact BDNF nucleotide sequence, whereas the anti-sense primer may be a degenerate primer homologous to a region of sequence likely to be found downstream of the sequenced fragment, e.g. the polyadenosine tail of mRNA, as reverse transcribed in the cDNA. It may then be necessary to use a similar method to retrieve sequence upstream of the sequenced fragment; for example, the anti-sense strand primer may correspond to exact BDNF nucleotide sequence and the sense strand primer may be a degenerate primer homologous to a region of BDNF sequence upstream of the sequenced fragment, e.g. a 5' polyadenosine tail added at the 5' end of cDNA using terminal deoxynucleotide transferase. Accordingly, the sequence of the entire BDNF gene or mRNA may be assembled.

DNA reaction products may be cloned using any method known in the art. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322, pUC, or Bluescript ® (Stratagene) plasmid derivatives. Recombinant molecules can be introduced into host cells via transformation, transfection, infection, electroporation, etc.

The BDNF gene is inserted into a cloning vector which can be used to transform, transfect, or infect appropriate host cells so that many copies of the gene sequences are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified. It may prove advantageous to incorporate restriction endonuclease cleavage sites into the oligonucleotide primers used in polymerase chain reaction to facilitate insertion into vectors. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and BDNF gene may be modified by homopolymeric tailing.

In specific embodiments, transformation of host cells with recombinant DNA molecules that incorporate an isolated BDNF gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

According to a preferred embodiment of the invention, once a cDNA-derived clone encoding BDNF has been generated, a genomic clone encoding BDNF may be isolated using standard techniques known in the art. For example, a labeled nucleic acid probe may be derived from the BDNF clone, and used to screen genomic DNA libraries by nucleic acid hybridization, using, for example, the method set forth in Benton and Davis (1977, Science 196:180) for bacteriophage libraries and Grunstein and Hogness (1975, Proc. Natl. Acad. Sci. U.S.A. 72:3961–3965) for plasmid libraries. Retrieved clones may then be analyzed by restriction-fragment mapping and sequencing techniques according to methods well known in the art.

Furthermore, additional cDNA clones may be identified from a cDNA library using the sequences obtained according to the invention.

5.5. Expression of the Brain Derived Neurotrophic Factor Gene

The nucleotide sequence coding for a BDNF protein, or a portion thereof, can be inserted into an appropriate expression vector, i.e., a vector which contains the necessary elements for the transcription and translation of the inserted protein-coding sequence. The necessary transcriptional and translation signals can also be supplied by the native BDNF gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding BDNF protein or peptide fragment may be regulated by a second nucleic acid sequence so that BDNF protein or peptide is expressed in a host transformed with the recombinant DNA moleucle. For example, expression of BDNF may be controlled by any promoter/enhancer element known in the art. Promoters which may be used to control BDNF expression include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionine gene (Brinster et al., 1982, Nature 296:39-42); prokaryotic expression vectors such as the $\beta$-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25), see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter for the photosynthetic enzyme ribulose biphosphate carboxylase (Herrera-Estrella et al., 1984, Nature 310:115-120): promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al, 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the bran (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Expression vectors containing BDNF gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted BDNF gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the BDNF gene is inserted within the marker gene sequence of the vector, recombinants containing the BDNF insert can be identified by the absence of the marker gene function. In the third approach, recombinant expression vectors can be identified by assaying the foreign gene product expressed by the recombinant. Such assays can be based, for example, on the physical or functional properties of the BDNF gene product in bioassay systems as described supra, in Section 5.2.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered BDNF protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous BDNF protein. Furthermore, different vector/host expression systems may effect processing reactions such as proteolytic cleavages to different extents.

In a specific embodiment of the invention, DNA encoding preproBDNF may be cloned into pCMV plasmid, amplified, and then used to transfect COS cells by the calcium phosphate method (Chen and Okayama, 1987, Mol. Cell. Biol. 7:2745-2752); BDNF activity may then be collected from cell culture medium (see Example Section 10, infra).

5.5.1. Identification and Purification of the Expressed Gene Product

Once a recombinant which expresses the BDNF gene is identified, the gene product should be analyzed. This can be achieved by assays based on the physical or functional properties of the product.

Once the BDNF protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any known BDNF assay, including, but not limited to, chick embryo dorsal root ganglia, perinatal rat retinal cells, or neural placode-derived neurons.

Importantly, methods used to prepare BDNF from brain tissue, because they involve, as a final step, preparative gel electrophoresis, would produce BDNF which was not fully active due to the presence of residual SDS (Barde and Thoenen, 1985, in "Hormones and Cell Regulation," Vol. 9, Dumont et al., eds., Elsevier Science Publishers, pp. 385-390). In contrast, the present invention permits the isolation of BDNF which is produced from recombinant nucleic acid molecules and which is free of SDS and therefore possesses full activity. For example, and not by way of limitation, the anti-BDNF antibodies of the invention (such as antibody directed toward the B5-33 amino acid fragment of porcine BDNF, described in Section 11, infra) may be used to collect recombinant BDNF by immunoprecipitation or affinity chromatography, thereby producing detergent-free, fully active BDNF.

5.6. Brain Derived Neurotrophic Factor Genes and Proteins

Using the methods detailed supra and in Example Sections 6 and 9, infra, the following nucleic acid sequences were determined, and their corresponding amino acid sequences deduced. The porcine BDNF cDNA sequence was determined, and is depicted in FIG. 1. The human genomic ,cDNA BDNF sequence was determined, and is depicted in FIGS. 5A through 5I which also present DNA sequences from pig, rat, and chicken. Each of these sequences, or their functional equivalents, can be used in accordance with the invention. Additionally, the invention relates to BDNF genes and proteins isolated from porcine, bovine, feline, avian, equine, or canine, as well as primate sources and any other species in which BDNF activity exists. The invention is further directed to subsequences of BDNF nucleic acids comprising at least ten nucleotides, such subsequences comprising hybridizable portions of the BDNF sequence which have use, e.g., in nucleic acid hybridization assays, Southern and Northern blot analyses, etc. The invention also provides for BDNF protein, and fragments and derivatives thereof, according to the amino acid sequences set forth in FIGS. 1 and 5A through 5I or their functional equivalents. The invention also provides fragments or derivatives of BDNF proteins which comprise antigenic determinant(s) or which are functionally active. As used herein, functionally active shall mean having positive activity in assays for known BDNF function, e.g. chick embryo DRG assays.

For example, the nucleic acid sequences depicted in FIGS. 1 and 5A through 5I can be altered by substitutions, additions or deletions that provide for functionally equivalent molecules. Due to the degeneracy of nucleotide coding sequences, other DNA sequences which encode substantially the same amino acid sequence as depicted in FIGS. 1 and 5A through 5I may be used in the practice of the present invention. These include but are not limited to nucleotide sequences comprising all or portions of the BDNF genes depicted in FIGS. 1 and 5A through 5I which are altered by the substitution of different codons that encode a functionally equivalent amino acid residue within the sequence, thus producing a silent change. Likewise, the BDNF proteins, or fragments or derivatives thereof, of the invention include, but are not limited to, those containing, as a primary amino acid sequence, all or part of the amino acid sequence substantially as depicted in FIGS. 1 and 5A through 5I including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are BDNF proteins or fragments or derivatives thereof which are differentially modified during or after translation, e.g., by glycosylation, proteolytic cleavage, linkage to an antibody molecule or other cellular ligand, etc.

Additionally, a given BDNF can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, et al., 1978, J. Biol. Chem. 253:6551), use of TAB ® linkers (Pharmacia), etc.

5.7. Generation of Anti-Brain Derived Neurotrophic Factor Antibodies

According to the invention, BDNF protein, or fragments or derivatives thereof, may be used as immunogen to generate anti-BDNF antibodies. Previous attempts to produce an anti-BDNF immune response have been unsuccessful, possibly because of the small quantities of purified BDNF available. By providing for the production of relatively abundant amounts of BDNF protein using recombinant techniques for protein synthesis (based upon the BDNF nucleic acid sequences of the invention), the problem of insufficient quantities of BDNF has been obviated.

To further improve the likelihood of producing an anti-BDNF immune response, the amino acid sequence of BDNF may be analyzed in order to identify portions of the molecule which may be associated with increased immunogenicity. For example, the amino acid sequence may be subjected to computer analysis to identify surface epitopes, according to the method of Hopp and Woods (1981, Proc. Natl. Acad. Sci. U.S.A. 78:3824-3828) which has been successfully used to identify antigenic peptides of Hepatitis B surface antigen. Alternatively, the deduced amino acid sequences of BDNF from different species could be compared, and relatively non-homologous regions identified; these non-homologous regions would be more likely to be immunogenic across various species.

For preparation of monoclonal antibodies directed toward BDNF, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77-96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.q., Teng et al., 1983, Proc. Natl. Acad. Sci. U.S.A. 80:7308-7312; Kozbor et al., 1983, Immunology Today 4:72-79; Olsson et al., 1982, Meth. Enzymol. 92:3-16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of BDNF. For the production of antibody, various host animals can be immunized by injection with BDNF protein, or fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and, *Corynebacterium parvum*.

A molecular clone of an antibody to a BDNF epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the F(ab')₂ fragment which can be produced by pepsin digestion of the antibody molecule; the Fab' fragments which can be generated by reducing the disulfide bridges of the F(ab')₂ fragment, and the 2 Fab or Fab fragments which can be generated by treating the antibody molecule with papain and a reducing agent.

Example Section 11 describes the preparation of polyclonal antisera directed toward the B5-33 peptide fragment of BDNF protein.

5.8. Identification of Additional Members of the BDNF/NGF Gene Family

Sequence analysis of the gene encoding BDNF and deduction of its amino acid sequence revealed that this protein has many structural similarities to NGF (FIG. 2). The primary sequence of mature BDNF, as well as the general structure and probable mode of processing from a precursor protein, suggest strongly that the NGF and BDNF genes may have evolved from a common ancestral gene. Within the region of the mature polypeptides, if only three gaps are introduced in the NGF sequences to optimize matching, a total of 51 amino acid identities are common to the previously known NGFs from many species and to porcine and human BDNF. These identities include all six cysteine residues, suggesting that the NGFs and BDNF share very similar secondary structure. Furthermore, four segments of six or more amino acids can be seen in which NGFs from all of the species listed above and from porcine BDNF are either identical, or differ by no more than about one conservative amino acid substitution. Thus, it is reasonable to conclude that NGF and BDNF appear to be closely related members of a gene family.

A rational search for additional members of the BDNF/NGF gene family may be carried out using an approach that takes advantage of the unanticipated existence of the conserved segments of strong homology between NGF and BDNF. For example, additional members of the BDNF gene family may be identified by selecting, from among a diversity of nucleic acid sequences, those sequences that are homologous to BDNF and NGF, and further identifying, from among the selected sequences, those that also contain nucleic acid sequences which are non-homologous to NGF and BDNF. The term "non-homologous" may be construed to mean a region which contains at least about 6 contiguous nucleotides in which at least about two nucleotides differ from NGF and BDNF sequence.

A preferred embodiment of the invention provides the following method. Corresponding to each of the four conserved segments ("boxes") described above and set forth in Table III, infra, sets of degenerate oligonucleotide probes of at least 18 nucleotides may be synthesized, representing all of the possible coding sequences for the amino acids found in either NGF or BDNF over six contiguous codons. Numbering with respect to the amino terminus of the mature polypeptides (so that His134 of preproBDNF is treated as His1 in the mature protein), the four boxes may be characterized as follows (numbered relative to human mature proteins; DNA sequence as depicted in FIG. 1).

TABLE III

| | | | DNA Sequence |
|---|---|---|---|
| Box 1: | NGF | Gly10—Ser19 | |
| | BDNF | Gly8—Ser17 | 587–616 |
| Box 2: | NGF | Lys50—Cys58 | |
| | BDNF | Lys50—Cys58 | 713–739 |
| Box 3: | NGF | Gly67—Asp72 | |
| | BDNF | Gly67—Asp72 | 764–781 |
| Box 4: | NGF | Trp99—Cys110 | |
| | BDNF | Trp100—Cys111 | 863–898 |

Synthetic oligonucleotides derived from sequence pairs from the boxes set forth in Table III may be utilized as primers to amplify by PCR sequences from a source (RNA or DNA) of potential interest. This might include mRNA or cDNA or genomic DNA from any eukaryotic species that could express a polypeptide closely related to BDNF or NGF. By carrying out as few as six PCR reactions (namely: a primer from Box 1 with a primer from Box 2; Box 1 with Box 3; Box 1 with Box 4; Box 2 with Box 3; Box 2 with Box 4; Box 3 with Box 4), it may be possible to detect a gene or gene product sharing any two of the four above segments of conserved sequence between NGF and BDNF. If one chooses to synthesize several different degenerate primers for each box, it may still be possible to carry out a complete search with a reasonably small number of PCR reactions. It is also possible to vary the stringency of hybridization conditions used in priming the PCR reactions, to allow for greater or lesser degrees of nucleotide sequence similarity between the unknown gene and NGF or BDNF. If a segment of a previously unknown member of the BDNF/NGF gene family is amplified successfully, that segment may be molecularly cloned and sequenced, and utilized as a probe to isolate a complete cDNA or genomic clone. This, in turn, will permit the determination of the unknown gene's complete nucleotide sequence, the analysis of its expression, and the production of its protein product for functional analysis.

The approach described above has been used to identify a novel gene related to both BDNF and NGF, and described in Example Section 13, infra.

In addition, the present invention provides for the use of the BDNF/NGF sequence homologies in the design of novel recombinant molecules which are members of the BDNF/NGF gene family but which may not occur in nature. For example, and not by way of limitation, a recombinant molecule can be constructed according to the invention, comprising portions of both NGF and BDNF genes. Such a molecule could exhibit properties associated with both BDNF and NGF and portray a novel profile of biological activities, including agonists as well as antagonists. Primary sequence of BDNF and NGF may also be used to predict tertiary structure of the molecules using computer simulation (Hopp and Woods, 1981, Proc. Natl. Acad. Sci. U.S.A. 78:3824-3828); BDNF/ NGF chimeric recombinant genes could be designed in light of correlations between tertiary structure and biological function. Likewise, chimeric genes comprising portions of any one or more members of BDNF/NGF gene family, including the novel member described in Section 13 may be constructed.

5.9. Utility of the Invention

The present invention relates to the nucleic acid sequence of BDNF and to the substantially pure protein, peptide fragments, or derivatives produced therefrom. BDNF may be produced, for the first time, in quantities sufficient for diagnostic and therapeutic applications. Likewise, anti-BDNF antibodies, also available for the first time as a consequence of the invention, and BDNF nucleic acid probes, may be utilized in diagnostic and therapeutic applications. For most purposes, it is preferable to use BDNF genes or gene products from the same species for diagnostic or therapeutic purposes, although cross-species utility of BDNF may be useful in specific embodiments of the invention.

5.9.1. Diagnostic Applications

The present invention, which relates to nucleic acids encoding BDNF and to proteins, peptide fragments, or derivatives produced therefrom, as well as antibodies directed against BDNF protein, peptides, or derivatives, may be utilized to diagnose diseases and disorders of the nervous system which may be associated with alterations in the pattern of BDNF expression.

In various embodiments of the invention, BDNF genes and related nucleic acid sequences and subsequences, including complementary sequences, may be used in diagnostic hybridization assays. The BDNF nucleic acid sequences, or subsequences thereof comprising about 15 nucleotides, can be used as hybridization probes. Hybridization assays can be used to detect, prognose, diagnose, or monitor conditions, disorders, or disease states associated with changes in BDNF expression, including, in particular, conditions resulting in sensory neuron damage and degeneration of retinal neurons. Such diseases and conditions include but are not limited to CNS trauma, infarction, infection, degenerative nerve disease, malignancy, or post-operative changes including but not limited to Alzheimer's Disease, Parkinson's Disease, Huntington's Chorea, and degenerative diseases of the retina. For example, total RNA in a tissue sample from a patient can be assayed for the presence of BDNF mRNA, wherein the decrease in the amount of BDNF mRNA is indicative of neuronal degeneration. Relatively high levels of BDNF mRNA have been identified in neuroblastoma tumor cells (see Section 14, infra, for details); accordingly, in a specific embodiment of the invention, detection of increased levels of mRNA using BDNF nucleic acid probes can be utilized to diagnose neuroblastoma tumor. The extremely low levels of BDNF synthesized by most tissues render BDNF mRNA a particularly useful tumor marker.

In alternate embodiments of the invention, antibodies directed toward BDNF protein, peptide fragments, or derivatives can be used to diagnose diseases and disorders of the nervous system, including, in particular, sensory disorders and degenerative diseases of the retina, as well as those disorders and diseases listed supra. The antibodies of the invention can be used, for example, in in situ hybridization techniques using tissue samples obtained from a patient in need of such evaluation. In a further example, the antibodies of the invention can be used in ELISA procedures to detect and/or measure amounts of BDNF present in tissue or fluid samples; similarly, the antibodies of the invention can be used in Western blot analysis to detect and/or measure BDNF present in tissue or fluid samples. An antibody of the invention which binds to BDNF in ELISA and Western blots is described in Section 11, infra.

In further embodiments of the invention, BDNF protein, peptide fragments or derivatives can be used to diagnose diseases and disorders of the nervous system. In a particular embodiment and not by way of limitation, labeled BDNF protein or peptide fragments can be used to identify tissues or cells which express the BDNF receptor in order to identify aberrancies of BDNF receptor expression and consequently, potential abnormalities in the tissue or cellular response to BDNF.

5.9.2. Therapeutic Applications

The present invention, which relates to nucleic acids encoding BDNF, and to proteins, peptide fragments, or derivatives produced therefrom, as well as to antibodies directed against BDNF protein, peptides, or derivatives, may be utilized to treat diseases and disorders of the nervous system which may be associated with alterations in the pattern of BDNF expression or which may benefit from exposure to BDNF or anti-BDNF antibodies.

In various embodiments of the invention, BDNF protein, peptide fragments or derivatives can be administered to patients in whom the nervous system has been damaged by trauma, surgery, ischemia, infection, metabolic disease, nutritional deficiency, malignancy, or toxic agents. The invention in particular can be used to treat conditions in which damage has occurred to sensory neurons or retinal ganglion cells by administering effective therapeutic amounts of BDNF protein or peptide fragments or derivatives. In various specific embodiments of the invention, BDNF can be locally administered to sensory neurons which have been severed, including, but not limited to, neurons in dorsal root ganglia or in any of the following tissues: the geniculate, petrosal, and nodose ganglia; the vestibuloacoustic complex of the VIIIth cranial nerve; the ventrolateral pole of the maxillo-mandibular lobe of the trigeminal ganglion; and the mesencephalic trigeminal nucleus. It may be desirable to administer the BDNF-related peptides or BDNF protein by adsorption onto a membrane, e.g. a silastic membrane, that could be implanted in the proximity of the severed nerve. The present invention can also be used for example in hastening the recovery of patients suffering from diabetic neuropathies, e.g. mononeuropathy multiplex. In further embodiments of the invention, BDNF protein or peptide fragments or derivatives derived therefrom, can be used to treat congenital conditions or neurodegenerative disorders, including, but not limited to, Alzheimer's disease, Parkinson's disease, and Huntington's chorea; in particular, the invention can be used to treat congenital or neurodegenerative disorders associated with sensory nerve dysfunction and degenerative diseases of the retina. For example, the BDNF protein, or peptide fragments, or derivatives of the invention can be used in the treatment of hereditary spastic paraplegia with retinal degeneration (Kjellin and Barnard-Scholz syndromes), retinitis pigmentosa, Stargardt disease, Usher syndrome (retinitis pigmentosa with congenital hearing loss), and Refsum syndrome (retinitis pigmentosa, hereditary hearing loss, and polyneuropathy), to name but a few. It is possible that a defect in BDNF synthesis or responsiveness may be the underlying etiology for syndromes characterized by a combination of retinal degeneration and other sensory dysfunction.

In a specific embodiment of the invention, administration of BDNF protein, or peptide fragments or derivatives derived therefrom, can be used in conjunction with surgical implantation of tissue in the treatment of Alzheimer's disease and/or Parkinson's disease. It has been shown that approximately 35 per cent of patients with Parkinson's disease suffer from Alzheimer-type dementia; BDNF produced according to the invention may prove to be useful single agent therapy for this disease complex. Similarly, BDNF produced according to the invention may be used therapeutically to treat Alzheimer's disease in conjunction with Down's Syndrome. BDNF produced according to the invention can be used in the treatment of a variety of dementias as well as congenital learning disorders. As described in Example Section 12, BDNF is capable of stimulating both dopaminergic and cholinergic neurons in culture, supporting its utility in the treatment of diseases involving these populations of neurons, including but not limited to, Parkinson's disease and Alzheimer's disease.

In further embodiments of the invention, BDNF protein, fragments or derivatives can be used in conjunction with other cytokines to achieve a desired neurotrophic effect. For example, and not by way of limitation, according to the invention BDNF can be used together with NGF or with skeletal muscle extract to achieve a synergistic stimulatory effect on growth of sensory neurons wherein synergistic is construed to mean that the effect of the combination of BDNF protein, peptide fragment, or derivative and a second agent achieves an effect greater than the same amount of either substance used individually. It is envisioned that BDNF may function synergistically with other CNS-derived peptide factors yet to be fully characterized, in the growth, development, and survival of a wide array of neuronal subpopulations in the central nervous system.

It is further envisioned that, based on the full characterization of the BDNF molecule, novel peptide fragments, derivatives, or mutants of BDNF may be developed which are capable of acting as antagonists of some, or all of the biological functions of BDNF. Such BDNF antagonists may be useful in the selective ablation of sensory neurons, for example, in the treatment of chronic pain syndromes.

In still further embodiments of the invention, antibodies directed toward BDNF protein, or peptide fragments or derivatives thereof, can be administered to patients suffering from a variety of neurologic disorders and diseases and who are in need of such treatment. For example, patients who suffer from excessive production of BDNF may be in need of such treatment. Anti-BDNF antibodies can be used in prevention of aberrant regeneration of sensory neurons (e.g. post-operatively), or, as discussed supra, in the treatment of chronic pain syndromes. In light of the high levels of BDNF mRNA found in neuroblastoma tissue, it is possible that BDNF serves as an autocrine tumor growth factor for neuroblastoma; accordingly, anti-BDNF antibodies can be administered therapeutically to achieve tumor regression in a specific embodiment of the invention.

5.10. Pharmaceutical Compositions

The active compositions of the invention, which may comprise all or portions of the BDNF gene product, including protein, peptide fragments or derivatives produced therefrom, or antibodies (or antibody fragments) directed toward BDNF protein, peptide fragments, or derivatives, or a combination of BDNF and a second agent, such as NGF or skeletal muscle extract, may be administered in any sterile biocompatible pharmaceutical carrier, including, but not limited to, saline, buffered saline, dextrose, and water.

BDNF protein, peptide fragment or derivative may comprise an amino acid sequence or subsequence thereof substantially as depicted in FIG. 1 or FIG. 5A through 5I; it may be preferable to use BDNF protein comprising, in particular, all or a portion of the amino acid sequence from about amino acid 134 to about amino acid 252, as depicted in FIG. 1, or a functionally equivalent sequence, as this subsequence is believed to comprise the functional portion of the BDNF molecule. BDNF may be derived from sequences corresponding to the BDNF genes of any suitable species, including, but not limited to, human, pig, rat, chicken, cow, dog, sheep, goat, cat, rabbit, etc.

The amount of BDNF protein, peptide fragment, derivative, or antibody which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, e.g. in the BDNF bioassay systems described supra, and then in useful animal model systems prior to testing in humans. Based on in vitro data, in a specific embodiment of the invention, a pharmaceutical composition effective in promoting the survival of sensory neurons may provide a local BDNF protein concentration of between about 5 and 25 ng/ml, and, preferably, between 10 and 20 ng/ml of BDNF. In an additional specific embodiment of the invention, a pharmaceutical composition effective in promoting the growth and survival of dopaminergic or cholinergic neurons may provide a local BDNF protein concentration of between about 10 ng/ml and 100 ng/ml.

Methods of introduction include but are not limited to intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

Further, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers.

The invention also provides for pharmaceutical compositions comprising BDNF proteins, peptide fragments, or derivatives administered via liposomes, microparticles, or microcapsules. In various embodiments of the invention, it may be useful to use such compositions to achieve sustained release of BDNF and BDNF-related products.

It is envisioned that it may be possible to introduce cells actively producing BDNF, BDNF related substances, BDNF antagonists, or anti-BDNF antibodies into areas in need of increased or decreased concentrations of BDNF.

6. EXAMPLE: MOLECULAR CLONING AND CHARACTERIZATION OF PORCINE BRAIN DERIVED NEUROTROPHIC FACTOR cDNA

The extreme rarity of BDNF protein in tissues precluded the use of standard strategies toward cloning the BDNF gene. Instead, a limited amount of protein sequence data was expanded, utilizing DNA amplification technology, as follows:

(i) Microgram quantities of BDNF were purified from kilogram quantities of porcine brain.

(ii) Purified BDNF was analyzed by protein microsequencing techniques, and the amino acid sequence of a stretch of 36 amino acid residues was determined.

(iii) Based on the amino acid sequence determined in (ii), oligonucleotides were synthesized and then used as primers in polymerase chain reaction, using porcine superior colliculus cDNA as template in order to amplify DNA encoding the defined amino acid fragment.

(iv) The DNA reaction product of (iii) was sequenced, and (v) Corresponding oligonucleotide primers were synthesized and utilized in polymerase chain reaction with porcine superior colliculus cDNA to generate overlapping fragments of DNA representing BDNF mRNA upstream as well as downstream of sequences encoding the original 36 amino acid fragment. Thus, the complete coding region for porcine BDNF was molecularly cloned in two overlapping fragments.

The details of each of these steps, as well as further characterization of the BDNF gene, are set forth below.

6.1. Materials And Methods

6.1.1. Purification Of BDNF From Porcine Brain

Purification of BDNF from porcine brain was performed by the procedure essentially as set forth in Hofer and Barde (1988, Nature 331:261-262).

Six kg of pig brain was homogenized with an Ultra-Turrax homogenizer in 0.2M sodium phosphate buffer, pH 6.0, containing 1 mM EDTA and freshly added phenylmethanesulphonyl fluoride (1 mM) at a ratio of 1 kg of brain to 2 liters of buffer. The pH of the supernatant was brought to pH 4.0 with 1 N HCl and stirred for 2 hr at 4° C. After centrifugation for 25 min at $20,000 \times g$ the combined supernatants (adjusted to pH 6.0 with 1N NaOH), corresponding to 3 kg of brain, were stirred for 2 hr with 1 liter of preswollen carboxymethyl-cellulose which had been equilibrated with 0.1M sodium phosphate, pH 6.0. After two washes with a total of 20 liter of 0.1M sodium phosphate, pH 6.0, the slurry was poured into a column and washed overnight in the same buffer containing 0.13M NaCl. Active fractions were eluted with phosphate buffer containing 0.5M NaCl and subsequently dialyzed against $2 \times 5$ liter of 5 mM potassium phosphate, pH 6.8. The dialyzed fractions resulting from processing $2 \times 3$ kg of starting material were applied to a 130 ml bed volume hydroxyapatite column which had been previously equilibrated with 5 mM potassium phosphate, pH 6.8. The column was then eluted with a linear gradient composed of 500 ml of 5 mM and 500 ml of 700 mM potassium phosphate, both pH 6.8, whereby the BDNF activity was eluted at approximately 500 mM potassium phosphate (see Barde et al., 1982, EMBO J. 1:549-553). By addition of 1.0M potassium phosphate, the pooled active fractions were adjusted to a final molarity of 700 mM potassium phosphate and applied to a 5 ml phenyl-sepharose column equilibrated with 700 mM potassium phosphate, pH 6.8. After washing with 40 ml of the same buffer, BDNF activity was eluted with 0.1M potassium phosphate, pH 6.8 dialyzed against distilled water, and lyophilized. The lyophilized material was taken up in an SDS-gel electrophoresis sample buffer containing 0.1% SDS and no mercaptoethanol as described in Barde et al. (1982, EMBO J., 1:549-553), before being applied to an SDS-gel comprised of a linear (rather than exponential) gradient of 10-25% acrylamide. After completion of electrophoretic separation, the gel was briefly stained (10 min) with Coomassie blue, destained for 20 min, and a band migrating at the level of cytochrome c was cut out and electrophoretically eluted from the gel. SDS was removed as described Barde et al. (1982, EMBO J., 1:549-553).

6.1.2. Protein Sequencing

BDNF was either sequenced directly (55 pmole as determined by amino acid analysis, with an initial yield of 40 pmole for the amino terminal histidine) or cleaved as follows: 5 to 10 μg BDNF (from 5 different preparations) were cleaved according to the following procedures. V8:1μg S. aureus V8 (Miles) was added to 5 μg BDNF in 0.2M NH4CO3, pH 8.0 containing 10% acetonitrile (total volume: 50 μl) and incubated overnight at room temperature. Trypsin: 1 μg TPCK-treated trypsin (bovine pancreas, Sigma Type XIII) was added to 8 μg BDNF in Tris-HCl (0.1M, pH 8.0) containing 10 mM CaCl2 (total volume: 40 μl) and incubated overnight at 37° C. Cyanogen bromide (CNBr): 10 μg BDNF were incubated for 3 hours at room temperature (total volume: 60 μl) with 10% (w/v) CNBr in 70% (v/v) formic acid (final concentrations). After addition of 500 μl H2O at the end of the reaction, the sample was concentrated to 50 μl in a speed-vac. 50 μl Tris-HCl (1.0M, pH 8.0) were added together with 5 μl β-mercaptoethanol and the sample was incubated overnight at 37° C. After addition of 5 μl iodomethane, the sample was evaporated to dryness on a speed-vac. Reduction and alkylation of BDNF after CNBr cleavage were found to be necessary: no fragments were obtained without reduction, as revealed by HPLC and Swank-Munkres SDS-gel electrophoresis (Swank and Munkres, 1971, Anal. Biochem. 39:462–477). This indicates that disulfide bridges are present in BDNF, and arranged in such a way that none of the cleavages can give rise to free peptides. After all cleavages, the dried samples were resuspended in 0.1% trifluoroacetic acid (TFA) and applied onto a reverse phase C8 microbore HPLC column (Applied Biosystems) and the peptides eluted at 0.1 ml/min, using a 60 min linear gradient of 0–60% acetonitrile in 0.1% TFA. Detection was at 214 nm with a Waters 441 UV detector. The peptides were sequenced by automated Edman degradation on a gas phase microsequencer (model 470A Applied Biosystems), according to Hewick (1981, J. Biol. Chem. 256:7990–7997) and Hunkapillar (1983, Methods Enzymol. 91:227–236). Detection of the PTH amino acids was as described by Lottspeich (1985, J. Chromatogr. 326:321–327).

6.1.3. Preparation Of DNA Templates

Pig genomic DNA was isolated according to the method of Herrmann and Frischauf (1987, Methods Enzymol. 152:180–183).

For preparation of cDNA, total RNA was Obtained from a 6 gram sample of superior colliculus of pig brain. The tissue specimen was obtained, dissected and frozen in liquid nitrogen at a local slaughterhouse. Standard methods (Okayama et al., 1987, Methods Enzymol. 154:3–28) were utilized to extract the RNA. Eighty μg total RNA was transcribed with the reverse transcriptase of the Moloney murine leukemia virus (BRL, according to the manufacturer's instructions except for the addition of 1 μl RNasin and the omission of actinomycin D), using the primer mixture CGGATCCGAATTCTGCAGTTTTTTTTTTTTT with A, C or G as terminal 3' nucleotide (oligo3, designed to match a 3' poly-A stretch and containing recognition sites for BamHI, EcoRI and PstI).

6.1.4. Polymerase Chain Reaction

Polymerase chain reaction (PCR) was performed according to the method described in Saiki et al., (1985, Science 230:1350–1354).

6.2. Results And Discussion

6.2.1. Results of Protein Microsequencing

The results of protein microsequencing are presented in Table IV.

TABLE IV

| Experimentally determined peptide sequence of BDNF |  |
|---|---|
| N-terminal | HSDPARRGELSV |
| V8 | XVTAADKKTAVD |
| V8 | KVPVSKGQLKQYFYE |
| CNBr | XGGTVTVLEKVP(V)(S) |
| CNBr | GYTKEGXRGIXRGI |
| Trypsin | (T)AVDMSGGTVTVLEK |
| Trypsin | ALTMDSK |
| Combined sequence | |
| VTAADKKTAVDMSGGTVTVLEKVPVSKGQL KQYFYE | |
| underlined amino acids represent sequences encoded by oligonucleotide primers used in PCR; see Section 6.1.2. | |

Seven contiguous segments of amino acid sequences were determined using Edman degradation, which could, in turn, be used to deduce a sequence of 36 amino acids representing approximately one-third of the entire amino acid sequence.

62.2. Synthesis Of Oligonucleotides and Use Of PCR To Obtain DNA Encoding An Amino Acid Fragment Two fully degenerate 17-mer oligonucleotide primers were chemically synthesized, based on the coding sequences for segments of six amino acids near the amino-terminal and carboxyl-terminal ends, respectively, of the 36 amino acid residue fragment described in Section 6.2.1., supra. In particular, two separate mixtures of 17-mer oligonucleotides (corresponding to all possible codons and designated oligo1 and oligo2) based on the sequence AADKKT (sense) and KQYFYE (antisense) (underlined in Table III) were chemically synthesized, and 150 pmole of each primer were added to 1 μg pig genomic DNA template. Thirty-Five amplification cycles were performed using the polymerase chain reaction (PCR) according to the instructions of the manufacturers (GeneAmp ™, Perkin-Elmer Cetus). Denaturation was at 94° C. for one minute, primer annealing at 45° C. for 2 min. and primer extension at 72° C. for 2 min. A DNA band of the predicted size (101 bp) was cut out from a 3% agarose gel (stained with ethidium bromide) and asymmetrically amplified as described by Innis et al. (1988, Proc. Natl. Acad. Sci. U.S.A. 85:9436–9440) with a 100-fold exoess of either oligo1 or oligo2.

6.2.3. Nucleotide Sequence Of cDNA Fragment

The resulting sense and antisense DNA fragments were sequenced by the dideoxynucleotide chain termination method (Sanger et al., 1979, Proc. Natl. Acad. Sci. U.S.A. 72:3918–3921) using the $^{32}$p end-labelled oligonucleotides 1 and 2 as primers. The observed nucleotide sequence contained only one open reading frame uninterrupted by a chain termination codon. The deduced amino acid sequence for this open reading frame was completely consistent with the actual amino acid sequence determined for this region of porcine BDNF.

6.2.4. Cloning Of The Entire Porcine BDNF cDNA

The complete coding region for porcine BDNF was molecularly cloned in two overlapping segments. In order to obtain the 3' portion (relative to the sense strand) of the BDNF cDNA, a 30-mer oligonucleotide primer containing 21 bases of exact sense strand BDNF sequence, from within the region described above, was synthesized to serve as a "sense primer". The nucleotide sequence of this primer was oligo 4, (5')AAACTAGT- CGACGGCAGTGGACATGTCGGG(3') [underlining indicates the sequence corresponding to sense strand of BDNF, from positions 643 to 663 on FIG. 1, encoding the amino acid sequence Thr-Ala-Val-Asp-Met-Ser-Gly (first two bases of Gly codon)]. The additional 9 nucleotides at the 5' end of this primer were included to provide convenient restriction endonuclease cleavage sites for Spe I and Sal I for use in molecular cloning. A three-fold degenerate 31-mer oligonucleotide primer was designed to be complementary to a stretch of poly-A preceded by any nucleotide (T, G, or C) on the sense strand of cDNA, and to contain recognition sites for the restriction endonucleases BamHI, EcoRI, and PstI. The sequence of this "antisense" primer (oligo 3) was (5')CGGATCCGAATTCT-GCAGTTTTTTTTTTTTX(3'), where X=A, C, or G. The synthetic oligonucleotide primers were utilized to amplify sequences from the porcine superior colliculus cDNA preparation described above, by PCR. Specifically, the 3' amplified DNA was obtained by using 10 μl of the reverse transcription reaction, 150 pmole of the sense primer (oligo 4) and 150 pmole of oligo3 as antisense primer in a PCR reaction. A Southern blot analysis was performed on the amplified DNA products and the band giving a hybridization signal with the $^{32}$P-end-labelled oligonucleotide AAGGATCCT-GCAGTTGGCCTTTCGAGACGG (oligo5, used as antisense primer in the 5' reaction described below and containing recognition sequences for BamHI and PstI) was cut out, extracted by the glassmilk method (gene clean), digested with EcoRI and SalI, cloned into a Bluescript SK+ plasmid (Stratagene) and sequenced.

In order to obtain the remainder (upstream or 5' portion) of the BDNF coding sequence, cDNA was prepared as described above, and poly-A tails were added at the 5' ends using terminal deoxynucleotide transferase. The same mixture of three 31-mer oligonucleotides each containing a stretch of 12 consecutive T residues, described above, was used to give a primer complementary to these added poly-A tails. A unique 30-mer oligonucleotide primer containing 17 bases corresponding to the complementary strand of the BDNF coding sequence, and with recognition sites for restriction endonucleases BamHI and PstI was synthesized. The sequence of this primer was (5')AAGGATCCT-GCAGTTGGCCTTTCGAGACGG(3') (oligo5, supra; underlining indicates the region complementary to the sense strand of the coding sequence of BDNF, from positions 709 to 693 on FIG. 1); this corresponds to the segment encoding the amino acid sequence Pro(last two bases of codon)-Val-Ser-Lys-Gly-Gln. The primers were added to the poly-A-tailed cDNA, and amplification by PCR was carried out as above. The reaction products were cut with PstI and cloned into Bluescript vector and the nucleotide sequence was determined by the dideoxynucleotide chain termination method.

6.2.5. Nucleotide Sequence Of Porcine BDNF cDNA

The combined nucleotide sequence determined from the overlapping porcine BDNF cDNA clones is shown in FIG. 1 together with the deduced amino acid sequence. The sequence comprises an open reading frame for a polypeptide of 252 amino acids. The identification of the initiator Met codon (ATG) is based on the presence of two adjacent chain termination codons (TAG-TGA) in the same reading frame, beginning 36 basepairs upstream. The amino terminus of porcine BDNF, determined by direct sequence analysis on purified protein corresponds to residue His134 of this polypeptide. Thus, the sequencing data show that mature BDNF is derived by processing from a precursor polypeptide. The residue His134 is preceded immediately by the sequence Arg-Val-Arg-Arg. Such sequences of one basic amino acid residue followed by a neutral residue and then two more basic residues have been implicated as target sites for proteolytic processing of precursor polypeptides. The deduced amino acid sequence of mature BDNF predicts a protein of 119 amino acids (molecular weight 13,511 daltons) with basic charge (pI =9.99), properties consistent with previous characterization of BDNF by evaluation of biologically active factor after fractionation by two-dimensional gel electrophoresis. The amino acid sequence of portions of BDNF determined by protein microsequencing (a total of 64 amino acid residues) is in complete agreement with the amino acid sequence deduced from the nucleotide sequence of cDNA clones (underlined in FIG. 1). The sequence of the precursor polypeptide is consistent with processing of BDNF in at least two steps: first, a signal peptide of perhaps 18 residues would be cleaved from the amino terminus, followed by cleavage between Arg133 and His134 to liberate the mature polypeptide. If this model is correct, then the precursor could be designated preproBDNF.

7. EXAMPLE: BDNF GENE IS DISTINCT FROM THE NGF GENE IN DIVERSE VERTEBRATE SPECIES 7.1. Materials And Methods 7.1.1. Preparation Of NGF And BDNF DNA Probes A plasmid containing a synthetic gene encoding mature human NGF, incorporating the normal human NGF coding sequence with a few conservative codon substitutions to introduce convenient restriction endonuclease cleavage sites, was purchased from British Biotechnologies Limited. A pair of 18-mer oligonucleotide primers were synthesized to permit amplification of a 270 base pair segment of this gene, corresponding to the coding region for amino acid residues 9 to 111, by PCR. In order to obtain a labeled DNA probe, a PCR reaction of 10 cycles was carried out with $^{32}$P-dCTP. A BDNF probe was obtained by similar procedures, except that amplification was carried out using porcine genomic DNA as the original template, and the segment amplified corresponded to the coding region for amino acids 28 to 111 of mature BDNF. A complementary strand ("antisense") primer corresponding to the region of amino acids 106 to 111 was synthesized, and had the sequence (5,)ACATACACAGGAAGTGTC(3'). A sense strand oligonucleotide primer was prepared for the region of amino acid residues 28-33 [(5')GCAGT-GGACATGTCGGGT(3,)]. Southern blot hybridization (Southern, 1975, J. Mol. Biol. 98:503-517) with these two probes was carried out under stringent conditions in 2×SSC at 68° C.

7.1.2. SEQUENCING OF BDNF GENES FROM VARIOUS SPECIES

The same two 18-mer oligonucleotides bracketing the coding region for amino acids 28 to 111 of mature porcine BDNF, described above, were used as primers to amplify, under standard PCR conditions, 252 base pair segments of genomic DNA of pig, rat, chicken, and human, and the resulting DNA reaction products were sequenced by the dideoxynucleotide chain termination method (Sanger et al., 1979, Proc. Natl. Acad. Sci. U.S.A. 72:3918-3921). In some cases the band of amplified DNA was cut out and extracted after agarose gel electrophoresis, and reamplified prior to sequencing. In other cases reamplification was not essential.

7.2 RESULTS AND DISCUSSION

Prior to the instant invention, BDNF protein had been purified only from pig. It was of paramount importance to demonstrate unequivocally that BDNF is not simply the porcine nerve growth factor beta subunit (betaNGF, or simply referred to herein as NGF), the purification and molecular cloning of which has not been reported to date. This was especially critical because the previously reported physical properties of porcine BDNF are virtually identical to those of the β-NGF monomer from a variety of species. The lack of a neutralizing antibody against porcine BDNF, and the previous lack of amino acid or nucleotide sequence information on porcine BDNF made it impossible to determine the exact relationship between BDNF and NGF. It was conceivable that the observed differences in biological activity between BDNF and NGF might, for example, simply reflect differences in NGF between pig and certain other species (e.g. mouse), or might result from differential modification of the NGF protein molecule in different tissues (e.g. pig brain versus mouse salivary gland), or from modifications inadvertently introduced into the protein at some step(s) during purification from pig brain.

If BDNF were found to be clearly distinct from NGF, it was of great interest to determine whether the BDNF gene is present in other species, notably man. Prior to the instant invention, no information was available concerning this point, because BDNF was purified from only one species. The presence of neurotrophic activity apparently distinct from NGF in a variety of crude extracts and conditioned media did not imply the existence of a substance identical or substantially equivalent to porcine BDNF.

Comparison of the predicted amino acid sequence of porcine BDNF with the known sequences of NGF from a number of species (human, bovine, guinea pig, mouse, chicken, and snake) indicated that BDNF is significantly less closely related to any vertebrate NGF than the NGF's are to each other (FIG. 2). A striking feature of the primary structure of mature BDNF is its similarity to that of NGF; with only 3 gaps introduced in the NGF sequences to optimize matching, 51 identities are common to the various NGFs (from snake to man) and BDNF (FIG. 2). Importantly, those identities include all 6 cysteine residues. Though the exact arrangement of BDNF's disulfide bridges are not yet known, it is clear that such bridges are present (Table III, legend). The 3 tryptophan and 2 phenylalanine residues found in BDNF are found at identical positions in NGF. We also note that 6 aspartic acid residues (out of 7 in BDNF) and 7 valine (out of 9) are present at identical positions in mammalian NGFs and BDNF. These 5 amino acids account for about half of the amino acid identities between the 2 proteins. Conversely, there are some striking differences between BDNF and all NGFs: in addition to the 3 gaps already mentioned, there are also 21 positions at which the amino acids are identical in all NGFs, but different in BDNF.

Most of BDNF's precursor sequence is unrelated to that of NGF, with 2 exceptions: the putative secretory signal sequence of BDNF shows 5 amino acid identities (out of 18 amino acids) and an overall striking relatedness with the signal sequence of mouse NGF, where cleavage has been demonstrated to occur after an alanine residue found in position 18 after the translation initiation methionine (Edwards et al., 1988, Mol. Cell Biol. 8:2456-2464). It seems likely that the alanine also found in position 18 in BDNF represents a potential cleavage site for the removal of BDNF's signal sequence. The other similarity with NGF starts at the only N-glycosylation consensus sequence (double underlined in FIG. 1), corresponding to asparagine 126. This asparagine is located 8 amino acids before the cleavage site giving rise to mature BDNF. The same arrangement is found in several NGFs, as well as the sequence Arg-X-Basic-Arg as the last 4 amino acids of the precursor (Schwarz et al., 1989, J. Neurochem. 52:1203-1209)

Proof that NGF and BDNF are encoded by distinct genes in a variety of vertebrate species was obtained by preparing DNA probes from molecularly cloned human NGF and porcine BDNF, and carrying out Southern blot hybridization with genomic DNA digested with restriction endonuclease EcoRI. Genomic DNAs were analyzed from the following sources: human, monkey, rat, mouse, dog, bovine, rabbit, chicken, and yeast. DNA was digested with EcoRI, and analyzed by Southern blotting, on duplicate filters, with a $^{32}$P-labeled human NGF probe and a porcine BDNF probe. Single bands were observed with each probe in all organisms tested except yeast. In most cases the bands hybridizing with the NGF and BDNF probes in any one organism were of different electrophoretic mobility, although in some cases (e.g. mouse DNA), the EcoRI fragments hybridizing to NGF and BDNF probes were of approximately the same size, and could not be resolved under the electrophoretic conditions used (FIG. 3).

A portion of the coding sequences for mature BDNF was amplified by PCR from genomic DNA of pig, rat, chicken, and human, and the nucleotide sequences determined. DNA sequence analysis of the amplified region from porcine genomic DNA exactly confirmed the sequence results obtained with molecular clones from porcine brain cDNA. The genomic sequences of rat, human, and chicken BDNF for this 252 base pair segment were also determined (FIGS. 5A through 5I). Remarkably, in rat and human the deduced amino acid sequence for the region of at least amino acids 28 to 111 was identical to that of porcine BDNF, although a number of nucleotide differences (e.g. conservative changes in the third position of a codon) were observed among the various species. In chicken a single amino acid substitution was observed in this region; residue 61 of the mature protein is a lysine in chicken compared to a methionine in mammalian BDNFs. The sequence data, together with the Southern blot hybridization experiment described above, provided unequivocal proof that BDNF is encoded by a highly conserved gene distinct from that encoding NGF.

8. EXAMPLE: EXPRESSION OF BDNF RNA IN NEURONAL VERSUS NON-NEURONAL TISSUES

8.1. Materials and Methods

8.1.1. Preparation of RNA

Total RNA was extracted from adult female mice tissues according to Okayama et al. (1987, Methods Enzymol 154:3-28). Briefly, frozen tissue was homogenized in 5.5M guanidinium thiocyanate, the lysate centrifuged to remove debris, and the supernatant overlaid onto a cushion of cesium trifluoroacetate adjusted to a density of 1.51 g/ml. After a 24 hour centrifugation at 125,000×g in a SW 27 swinging bucket rotor (Beckmann), the RNA was resuspended and precipitated with ethanol and 8M ammonium acetate and stored at −70° C. Electrophoresis was according to Lehrach et al. (1977, Biochemistry 16:4743-4751) on 1.3% agarose formaldehyde gels. The RNA was transferred to nylon membranes (Hybond-N, Amersham) and hybridized overnight at 62° C. in 1 ml 2×SSC containing 50% formamide with a $^{32}$P-cRNA mouse BDNF probe (10$^7$ cpm, see below). Washing was for 60 min at 65° C. in 0.1 X SSC. After washing, the blot was incubated for 60 min at room temperature with 0.1 μg/ml RNAse A (Pharmacia) and the film exposed at −70° C. (with intensifying screen) for 48 hours.

8.1.2. Preparation of cRNA Probe

A mouse brain cDNA library was screened with 2 independent BDNF oligonucleotides. Double positive clones were isolated and subcloned into the EcoRI site of a Bluescript SK+ plasmid (Stratagene). The nucleotide sequence corresponding to nucleotides 350 to 829 of the pig sequence (see FIG. 1) was determined. In this sequence, a total of only 4 amino acid differences were found between mouse and pig BDNF, indicating a remarkable degree of conservation of this domain between pig and mouse BDNF. A single stranded RNA probe was prepared using this template and the T3 polymerase (Promega). The specific activity of this probe was $10^8$ cpm/μg.

8.2. Results and Discussion

Northern blot analysis was used to evaluate the expression of BDNF mRNA in neuronal versus non-neuronal tissues. Northern blot analyses were performed using mouse tissues, allowing more rapid processing for RNA extraction than pig tissues. A 32P-cRNA probe detected a signal at about 1.45 kb in the brain (FIG. 4) and spinal cord (data not shown). Significantly, no signal was detected in any other tissue including kidney, gut, lung, liver, spleen, heart and muscle (FIG. 4). Assuming the size of the pig mRNA to be similar to that of the mouse, the cDNA sequence shown in FIG. 2 represents over 80% of the complete mRNA sequence.

A significant observation in the delineation of BDNF's physiology is that the mRNA coding for this protein was only found in the central nervous system and not in 7 non-CNS tissues. BDNF mRNA was found not only in total brain (FIG. 4), but also in the spinal cord and the superior colliculus (the sequence presented in FIG. 1 derives entirely from a superior colliculus cDNA template). These data support the idea that BDNF is a target-derived neurotrophic factor and that BDNF-responsive neurons are either intrinsic to the CNS or directly connected with CNS structures. Indeed, all the neurons known to respond to BDNF so far either project into the CNS, like the dorsal root or the cranial sensory ganglia (Lindsay et al., 1985, Dev. Biol. 112:319-328; Davies et al., 1986, J. Neurosci. 6:1897-1904), or are CNS neurons like the retinal ganglion cells (Johnson et al., 1986, J. Neurosci. 6:3031-3038). Clearly, detailed studies need to be done to examine the exact distribution of the sites of synthesis of BDNF in the CNS, but it is already evident that the distribution of BDNF mRNA is very different from that NGF mRNA, found in many non-CNS tissues (Heumann et al., 1984, EMBO J. 3:3183-3189; Shelton et al., 1984, Proc. Natl. Acad. Sci. U.S.A. 81:7951-7955).

9. EXAMPLE: MOLECULAR CLONING AND CHARACTERIZATION OF HUMAN AND RAT BDNF GENES

9.1. Materials and Methods

9.1.1. Genomic DNA and cDNA Libraries

An adult human retina cDNA library, in lambda-ZAPII was obtained from Stratagene. A human placenta genomic DNA library in EMBL3/SP6/T7 was obtained from Clontech. A rat fetal brain cDNA library in λgt11 was obtained from Clontech. A rat genomic DNA library in EMBL3/SP6/T7 was obtained from Clontech. Both genomic libraries were prepared by partial digestion of genomic DNA with Sau 3A restriction endonuclease and ligation into the BamHI site of the vector. A rat brain cDNA library in lambda-ZAPII was obtained from Stratagene.

9.1.2. Preparation of BDNF DNA Probes $^{32}$P-labeled BDNF DNA probes were prepared using the same oligonucleotide primers described in Section 7.1.1., supra in PCR reaction with human genomic DNA in order to amplify the coding region for residues 28-111 of human BDNF. In parallel, a rat BDNF-specific $^{32}$P-labeled probe was obtained, using rat genomic DNA as a template for PCR.

9.1.3. Screening of Libraries

Lambda phage libraries were screened according to standard methods (Benton and Davis, 1977, Science 196:180-182; Maniatis et al., 1978, Cell. 15:687-701), hybridizing in 50% formaldehyde with dextran sulfate and Denhardt's solution at 42° C. Filters were prehybridized at 42° C. in 50% formamide, 5XSSCPE, 10% Denhardt's, 0.5 mg/ml Salmon sperm DNA, 0.1% SDS, and 10% dextran sulfate. Hybridization was carried out in the same buffer except that Denhardt's solution was at 2%, Salmon sperm DNA was at 0.1 mg/ml, and SDS and dextran sulfate were omitted. After hybridization filters were washed at 68° C. Human BDNF probe was used to screen human genomic DNA and retina cDNA libraries; rat BDNF probe was used to screen rat genomic DNA and brain cDNA libraries. Libraries were also screened with human and rat NGF probes, prepared as described in Section 7.1.1. supra.

9.2. Results and Discussion

At least 670,000 plaques were screened from each library. Positive human clones were considered to be those which hybridized with the human BDNF probe, but not with the human NGF probe described above. BDNF genomic clones were obtained from both the human and rat libraries at a frequency consistent with representation of the BDNF gene at one copy per haploid genome. For both rat and human genomic libraries, approximately one million plaques were screened. Three positives were obtained from the rat genomic library and one was obtained from the human genomic library. Positive clones from the human retinal and rat brain cDNA libraries were obtained at a frequency consistent with a gene expressed at very low levels; in rat brain cDNA, 2 positives were identified in 670,000;

in human retinal cDNA library, one in 670,000 clones were identified. No positive clones were detected among 670,000 from the commercial cDNA library prepared from human fetal brain. Nucleotide sequencing was carried out on human BDNF cDNA and genomic clones, using synthetic oligonucleotide primers representing exact sequences from within the human and rat BDNF coding region, as determined in Section 7.1.2., supra. The longest human cDNA clone obtained had an insert of approximately 1.6 to 1.8 kbp, and, as expected, contained the exact sequence of the portion of human BDNF determined after direct amplification from human genomic DNA, as described in Section 7.2., supra. Detailed sequence analysis of this cDNA (FIGS. 5A through 5I) clone revealed an open reading frame encoding a polypeptide of 247 amino acids, similar but not identical to the full-length precursor to porcine BDNF. Within the region corresponding to the mature BDNF polypeptide (e.g. from the codon for His134 to the chain termination codon) no differences in deduced amino acid sequence were found; all nucleotide substitutions between pig and man were conservative with respect to coding specificity. The remainder of the putative BDNF precursor polypeptide showed some amino acid sequence differences between human and pig, most notably the absence in the human BDNF gene of 5 of 6 consecutive Ser codons seen in pig, resulting in a slightly shorter polypeptide (247 versus 252 amino acids).

Libraries prepared in vector EMBL3 have inserts of between 10 to 23 kbp of foreign DNA. The exact insert size in the human genomic BDNF clone analyzed in detail was not determined. However, the clone contained a single EcoRI restriction endonuclease fragment of approximately 4 kbp that hybridized with the labeled BDNF probe used to screen the library. This fragment is the expected size, based on the results of Southern blot hybridization of human genomic DNA with the porcine BDNF probe described above. Sequence analysis was carried out on the human clone, using synthetic oligonucleotides representing cDNA sequence to prime DNA synthesis from the bacteriophage DNA template. The sequence of the coding sequence for the putative human BDNF precursor was found to be identical to that in the human cDNA clone, with the exception of a single nucleotide substitution in the prepro region, corresponding to an amino acid substitution of methionine (ATG) for Valine (GTG), at nucleotide 785, in FIG. 5D. This change may reflect a polymorphism in the human genome. As in the case of the human NGF gene, no intervening sequences were detected within the coding sequence for the putative human preproBDNF. Rat cDNA sequence data is also presented in FIGS. 5A through 5I.

10. EXAMPLE: EXPRESSION OF RECOMBINANT BDNF

10.1. Materials and Methods

10 1.1. Preparation of a BDNF Expression Vector

The sequence corresponding to pig preproBDNF was obtained by using the oligonucleotide primers (150 pmole each) ATAATCTAGATGAC-CATCCTTTTTCCTT (sense) ATAATCTAGAC-TATCTTCCCCTCTTAAT (antisense) in a PCR reaction using 1 µg of pig genomic template (each primer has an added XbaI site). The amplification reaction was as described, except that the annealing temperature was 50° C. After digestion with XbaI, the amplified DNA was ligated in the XbaI site of the plasmid pCMV$^1$ to produce pCMV$^1$-pBDNF$^{-1}$ (−1 denotes sense orientation in FIG. 6 and corresponds to COS+ in Table V), and the plasmid was introduced into XL-1 bacteria by electroporation.

10.1.2. Expression of BDNF in COS Cells pCMV1-pBDNF plasmid DNA from positive clones (checked by hybridization with oligo5, FIG. 2) was cut with both XbaI and PstI. The size of the resulting products allowed us to determine the orientation of the inserts, and both plasmids were used to transfect COS cells by the calcium phosphate method (Chen et al., 1987, Mol. Cell Biol. 7: 2745-2752), and the growth medium collected after 24 h. BDNF activity was tested in the chick embryo dorsal root ganglion bioassay discussed in detail supra.

10.2. Results and Discussion

E8 chick spinal sensory neurons were plated (6,000 per well), incubated for 24 h and counted after 24 h (Lindsay et al., 1985, Develop. Biol. 112: 319-328). The values are the means of triplicate determinations ±standard deviation. BDNF and NGF were used at 1 ng/ml, concentrations at which maximal survival is observed with either factor. COS+ refers to cells transfected with plasmids containing the BDNF insert in the sense orientation, COS− to cells transfected with plasmids containing the BDNF inserts in the reverse orientation. COS refers to non-transfected cells. At dilutions higher than 1:20, no survival above control was seen with either COS− or COS conditioned medium. In all experiments without NGF, a monoclonal anti-NGF antibody (Korsching et al., 1988, Proc. Natl. Acad. Sci. U.S.A. 80:3513-3516) was used at 1 µg/ml.

As shown in Table V, only the medium obtained from cultures of COS cells bearing pCMV1-pBDNF plasmid in the sense orientation was associated with chick sensory neuron survival above control values. Therefore, the recombinant BDNF is biologically active. Further, addition of BDNF isolated from pig brain did not increase the survival of sensory neurons significantly above survival levels resulting from recombinant BDNF alone, indicating that the recombinant BDNF is capable of saturating BDNF receptors. Recombinant BDNF was also observed to have an additive or synergistic effect toward promoting chick sensory neuron survival when used together with NGF.

TABLE V

| COS medium (final dilution) | Survival of cultured chick sensory neurons | | |
|---|---|---|---|
| | 1:20 | 1:50 | 1:200 |
| COS+ | | 2,510 ± 263 | 2,833 ± 171 |
| COS− | 211 ± 16 | | |
| COS | 250 ± 87 | | |
| BDNF + COS+ | | 2,516 ± 209 | |
| NGF + COS+ | | 5,770 ± 72 | |
| BDNF alone | | 2,718 ± 424 | |

11. EXAMPLE: GENERATION OF ANTIBODIES TO BDNF

11.1. Materials and Methods

A polyclonal antiserum specific for BDNF, designated sera 4, was generated in a NZ white rabbit by immunization with a synthetic peptide.

11.1.1. Peptide Synthesis and Coupling to Carrier a peptide consisting of 34 amino acid residues, designated B5, was synthesized by conventional methods. It has the following amino acid sequence, corresponding to 33 residues of mature BDNF (residues 153 to 185 of the complete porcine preproBDNF sequence shown in FIG. 1) with an additional cysteine residue at the amino-terminus (shown in italics) to permit coupling to a carrier protein using m-maleimidobenzoic acid-N-hydroxysuccinimide (MBS), if desired:

*Cys*—Val—Thr—Ala—Ala—Asp—Lys—Lys—Thr—Ala—Val—Asp—Met—Ser—Gly—Gly—Thr—Val—Thr—Val—Leu—Glu—Lys—Val—Pro—Val—Ser—Lys—Gly—Gln—Leu—Lys—Gln—Tyr

The B5 peptide was coupled to bovine serum albumin (BSA) using bis-diazo benzidine (BDB). Fresh BDB was prepared by dissolving 46 mg benzidine-HCl (p-diaminodiphenyl-HCl, obtained from Sigma) in 9.0 ml of 0.2N HCl. 35 mg $NaNO^2$ was dissolved in 1.0 ml $H_2O$ and added to the benzidine solution, and stirred for 1 hour at 4° C. 21 mg of BSA was dissolved in 3.0 ml of 0.16M borate, 0.13M NaCl, pH 9.0. Approximately 15 mg of B5 peptide was dissolved in 1.5 ml borate-NaCl buffer, pH 0.0. The peptide solution was added to the BSA solution, and placed in ice. 1.0 ml of BDB was added to the BSA-peptide solution, and the reaction mixture was incubated with stirring for 2 hours at 4° C.; the pH was monitored and maintained in the range of 9.0 by the addition of small amounts of 0.5M NAOH, as required. The reaction was terminated by addition of 0.2 ml of 1% phenol-buffered solution. Excess reagents were removed by dialysis against phosphate buffered saline (PBS).

11.1.2. Immunization

A total of six rabbits were immunized according to the following protocol:

Rabbits 1 and 4—peptide B5 coupled at its C-terminus to BSA, using BDB;

Rabbits 2 and 3—peptide B5 coupled at its N-terminus to BSA, using MBS;

Rabbits 5 and 6—peptide B5 mixed with powdered nitrocellulose.

In all cases the first immunization used 1 mg of immunogen (100 μg B5/500 μg nitrocellulose for rabbits 5 and 6) in 0.5 ml PBS plus 0.5 ml ml complete Freund's adjuvant. This mixture was injected subcutaneously into multiple sites on the back. The second immunization was carried out three weeks later, and was identical to the first except that incomplete Freund's adjuvant was used in place of complete Freund's adjuvant. Subsequent boosts occurred at intervals of 4–6 weeks. Rabbits were bled 1 week after immunization, and the antisera routinely checked for binding to the pure B5 peptide by enzyme-linked immunosorbent assay (ELISA).

11.1.3. Detection of Antibody Binding to BDNF

100 μg of antigen (B5 peptide) in $H_2O$ was added to wells on a microtiter plate and allowed to dry overnight, then washed briefly with $H_2O$ and blocked with 100 μg 1% gelatin for 30 minutes at room temperature. Wells were washed three times with distilled water, and then 100 μg of antisera was added and allowed to incubate at 4° C. overnight. Wells were then washed three times in PBS/0.05% triton X-100, after which 100 μg peroxidase labeled anti-rabbit immunoassay (1/1000 dilution) was added to wells and incubated at room temperature for three hours. Wells were washed twice, and 100 μg ABTS solution (10 mg ABTS (Sigma) dissolved in 10 ml 0.1M NaCitrate pH 4.0 plus 10 μg $H_2O_2$) was added and incubated for about 5 minutes, until color developed. The reaction was stopped by the addition of 10 μg 1% $NaN_3$. Samples were diluted 1:5 with $H_2O$ and optical density was measured at 415 nm.

11.2. Results and Discussion

The antiserum from rabbit 4 (sera 4) showed the highest titre, (FIG. 7A) and was utilized in subsequent experiments. Antibodies from sera 4 were partially purified by precipitation with ammonium sulphate; to a portion of antiserum an equal volume of saturated ammonium sulfate was added slowly, with stirring, and the solution was stirred for a further 15 minutes, then centrifuged at 2,000×g. The pellet was washed twice in 50% saturated ammonium sulphate, then redissolved in PBS in a volume corresponding to the original volume of serum. Ammonium sulphate was removed by dialysis against several changes of PBS. The dialyzed solution was aliquoted in 1.0 ml volumes and subjected to lyophilization using a speed-vac. A sample of sera 4 antibody was resuspended in 0.5 ml $H_2O$ and tested for reactivity with peptide B5 by ELISA, and was found to react to a dilution of 1:4000.

Polyclonal antibodies to a synthetic peptide (B5) corresponding to a 33 amino acid fragment of porcine BDNF were generated by immunizing rabbits as described above. Sera 4, which showed the highest titre against the synthetic peptide, showed reactivity with purified BDNF from porcine brain by ELISA (FIG. 7B). Weak reactivity was also detected by immunoblotting (DATA NOT SHOWN). However, the antiserum was unable to block the activity of BDNF in a biological assay on chick embryo dorsal root ganglion sensory neurons.

12. EXAMPLE: NOVEL BIOLOGICAL EFFECTS OF BDNF

The following observations indicate that BDNF is capable of (i) sustaining the survival and inducing the fully differentiated state of CNS dopaminergic neurons; (ii) sustaining the survival of CNS cholinergic neurons; and (iii) suppressing the proliferation of astroglial cells. These biological effects of BDNF have not been described previously. As dopaminergic neurons, cholinergic neurons, and astroglial cells may each be associated with neurological diseases or disorders, BDNF may prove to be useful in the treatment of neuropathologies involving these cell populations.

12.1. Materials and Methods

12.1.1. Methods for Culturing Dopaminergic Substantia Nigra Neurons

Ventral mesencephalon was dissected from brains of rat embryos varying in age from embryonic day 13 to embryonic day 15. Typically, two litters were used in each experiment. The dissection solution had the following composition: NaCl, 136.8 mM, KCl, 2.7 mM, $Na_2HOP_4.7H_2O$, 8.0 mM, $KH_2PO_4$, 1.5 mM, glucose, 6 mg/ml, and BSA, 0.1 mg/ml, pH 7.4. This solution was prepared and subsequently filter sterilized through a 0.2 μM pore filter. The dissection was performed under non-sterile conditions. Once the tissue was dissected from all the brains, the rest of the procedure was carried out under sterile conditions. The tissue fragments were placed in a 35 mm culture dish and minced using a fine scissors. Two ml of F-12 nutrient media containing 0.125% trypsin was then added to the tissue, and an incubated at 37° C. At the end of this incubation period, DNAseI was added to the slurry such that the final concentration was 80 ng/ml. Another identical incubation was carried out, and the tissue slurry was subsequently added to 8.0 ml of growth medium consisting of Minimal Essential Medium (MEM) supplemented with 2 mM glutamine, 6 mg/ml glucose, 5 units/ml penicillin, 5 mg/ml streptomycin, and 7.5% fetal calf serum (FCS). The sample was centrifuged in a tabletop centrifuge at room temperature at 500 rpm for a period of 5 minutes. The medium was aspirated, and 2 ml growth medium was added to the cell pellet. A fire polished pipette with an opening of 1 mm was used to triturate the cells eight times. The remaining tissue fragments were allowed to settle by gravity, and a small aliquot of the supernatant was taken to assess cell number by counting in a hemocytometer. After cell density was determined, the cells were plated into tissue culture plates at a density of 50,000/cm$^2$.

The culture plates were prepared on the day prior to dissection. Tissue plates (24 well, 2 cm$^2$/well) were precoated with polyornithine (molecular weight 30,000–70,000 g/mol), 0.5 mg/ml, at room temperature for 3 hours. The plates were extensively washed with water, and subsequently treated with mouse laminin, 5 μg/ml, at room temperature for 3 hours. The plates were then washed with water as above, and incubated overnight at 37° C. in a humidified atmosphere consisting of 5% $CO_2$, 95% air, in the presence of growth medium. The medium in the plates was removed the following day and replaced with fresh growth medium.

Once the cells were plated into the culture plates, the cells were placed in an incubator set at 37° C. and 5% $CO_2$/95% air for a period of 24 hours. The culture medium was changed to a serum-free formulation (SFM) having the following composition: a 1:1 (vol:vol) mixture of Basal Eagle Medium (BEM) and nutrient mixture F-12 with glucose (33 mM), glutamine (2 mM), $NaHCO_3$ (15 mM), HEPES (10 mM), supplemented with insulin (25 μg/ml), transferrin (100 μg/ml), putrescine (60 μM), progesterone (20 nM), sodium selenite (30 nM), penicillin (5 U/ml), streptomycin (5 mg/ml), and $T_3$ (30 nM). In some experiments, purified BDNF was added to the cultures after the media change to SFM on culture day 2.

The solutions used for culturing dopaminergic neurons were prepared using water taken from a Milli-Q reagent water system. The tissue culture media formulations were obtained through Gibco Laboratories (Santa Clara, Calif.), as was the fetal calf serum (lot number 43N1086) and the mouse laminin. All other media components were purchased from Sigma Chemical (St. Louis, Mo.), and were cell culture tested grade. The polyornithine and DNAseI were also obtained from Sigma. Trypsin was obtained from Worthington (Freehold, N.J.), lot number 3667. Commercial chemicals were of analytical grade, purchased from Baker Chemical (Phillipsburg, N.J.). The BDNF used in these experiments was purified from pig brain by Dr. Y.-A. Barde, according to the procedure of Barde et al., 1982.

12.1.2. Methods for Immunocytochemical Staining of Ventral Mesencephalon Cultures Fixative solutions were prepared fresh for each experiment. For the staining of tyrosine hydroxylase (TH), the fixative was 4.0% paraformaldehyde in Sorenson's phosphate buffer. The Sorenson buffer was prepared by adding a 0.2M solution of $KH_2PO_4$ to a stock of 0.2M $Na_2HPO_4$ until the pH reached 7.3. The paraformaldehyde was subsequently added to the solution and briefly heated, to allow it to be dissolved, and cooled to room temperature before use.

To begin the procedure, culture medium was removed from the culture dishes by gentle suction, and the proper fixative solution was gently added to the dish. A room temperature incubation of 20 minutes was carried out. Three washes in Sorenson's phosphate buffer, for 5 minutes each, with gentle rotation, followed. The cells were then incubated in a quench solution for 30 minutes at room temperature with gentle rotation. The quench solution for the cultures to be stained for TH consisted of Sorenson's phosphate buffer containing 2% normal horse serum. Next, the cultures were incubated in permeabilization buffer at room temperature for 30 minutes with gentle rotation. The solution consisted of Sorenson's buffer containing 0.2% saponin, and 1.5% of normal horse serum for the cultures to be stained for TH. Following the permeabilization step, the cultures were incubated in the presence of primary antibody overnight at 4° C. The antibody against rat TH was a mouse monoclonal antibody of isotype IgG2a. It was used at 40 μg/ml in a solution of 10 mM $NaPO_4$, 50 mM NaCl, 0.2% saponin pH 7.5. Following the primary antibody incubation, the cultures were washed 5 times for 15 minutes each in the appropriate permeabilization buffer. Next, the cultures were incubated with secondary antibody conjugated to biotin, that is biotinylated horse anti-mouse IgG. This incubation was carried out at room temperature for two hours with gentle rotation. Washes identical to those described above followed, and the cultures were then incubated in the presence of a preformed avidin-biotinylated horseradishperoxidase complex (ABC reagent, Vector Laboratories, Burlingame, Calif.) prepared according to manufacturer's protocol. After a 30 min. incubation at room temperature with gentle rotation, the cultures were washed as described above. The cultures were subsequently incubated with 55 mM Tris-Cl pH 7.3 containing 0.5 mg/ml diaminobenzidine and 0.01% hydrogen peroxide. The development of reaction product was allowed to proceed for 2–5 min. after which the solution was removed and the cultures were washed several times with ice cold PBS. The number of positive cells/cm$^2$ was then ascertained.

The paraformaldehyde and the glutaraldehyde were obtained from Fluka Chemical. Vectastain kits containing normal serum (used as a blocking agent), biotinylated, affinity-purified anti-immunoglobulin, avidin DH, and biotinylated HRP-H were purchased from Vector Laboratories. The diaminobenzidine was obtained from BRL (Gaithersberg, Md.).

12.1.3. Methods Used in Measuring $^3$H-dopamine Uptake in Ventral Mesencephalon Cultures $^3$H-dopamine ($^3$H-DA) uptake was performed as described by Dal Toso et al. (1988, J. Neurosci. 8:733–745) with minor modifications. The uptake buffer had the following composition: NaCl, 136.8 mM, KCl, 2.7 mM, Na$_2$HPO$_4$.7H$_2$O, 8.0 mM, KH$_2$PO$_4$, 1.5 mM, glucose, 5.0 mM, caCl$_2$2, 1.0 mM, MgSO$_4$, 1.0 mM, ascorbic acid, 0.1 mM, pargyline, 0.1 mM, pH 7.4 When necessary, 5.0 µM benztropine mesylate (BZT) was added to the uptake buffer.

The cells were washed once with prewarmed (37° C.) uptake buffer, and replaced with 0.4 ml uptake buffer/2 cm$^2$ well. The cultures were then preincubated for 5 min. at 37° C. At the end of this preincubation 0.1 ml $^3$H-DA, in uptake buffer (250 nM, 40 Ci/mMol), was added such that the final concentration of $^3$H-DA in the buffer was 50 nM. The cultures were incubated at 37° C. for 15 min., followed by four washes at 4° C., 0.5 ml each, with uptake buffer. Two additional washes with ice cold PBS (10 mM NaPO$_4$, 150 mM NaCl, pH 7.6) were carried out as well. After the last wash was completed, 0.2 ml/2 cm$^2$ well 0.5N NaOH was added to the cells, and allowed to stand at room temperature for two hours. The NaOH extract was subsequently collected, and counted in a scintillation counter (Packard, LS 500TD) with 10 ml "ultimagold" scintillation fluid. Specific uptake was defined as that uptake which was abolished in the presence of 5 µM BZT. Typically, this represented 70-90% of the total uptake observed.

$^3$H-DA was obtained from NEN (Boston, MA). Ascorbate, pargyline, BZT, and glucose were obtained from Sigma (St. Louis, Mo.). The ultimagold scintillation fluid was purchased from Packard (Sterling, Va.).

12.1.4. Methods for Producing Cultures of Basal Forebrain Cholinergic Neurons Primary cultures of basal forebrain cholinergic cells were produced from embryonic day 17 rats. Specifically, the cholinergic neurons used in this study were derived from the medial septal nucleus and the nucleus of the diagonal band of Broca. This neuronal population projects primarily to the hippocampus. The dissociated mixed cultures (neurons and glia) were produced by the following procedure. The septal region was dissected free from the surrounding tissue, and removed from the fetal brain. The tissue pieces were then pooled, minced with scissors, and treated for 20 minutes at 37° C. with 125% trypsin. The trypsin was inactivated by dilution in the plating medium (Dulbecco's modified Eagle medium (DMEM) containing 1% penicillin and streptomycin, 5% horse serum, and 1% N3, a hormone supplement). A single cell suspension was produced by trituration of the digested tissue fragments with a fire polished pasteur pipette. The dissociated cells were counted on a hemocytometer and plated at the appropriate density in the plating medium. Test ligands were added to the cultures five to six hours after plating and the cells were then grown in vitro for ten days with medium changes being made every three days.

12.1.5. Choline Acetyl Transferase Assays

Following the treatment period the cells were either used for choline acetyltransferase (CAT) enzyme assays or processed for immunohistochemical staining for CAT by the following protocol. The monoclonal antibody to CAT was purchased from Boehringer Mannheim Biochemical Co. and has been characterized elsewhere. At the end of the experimental period the cells were rinsed twice with DMEM. The cultures were fixed by a two step procedure; 50 µl of 4% paraformaldehyde was added to 50 µl of DMEM for a 10 minute incubation period. This solution was removed and replaced with 100 µl of 4% paraformaldehyde and the incubation was continued for 30 minutes at room temperature. Following the fixation, the cells were rinsed three times with phosphate buffered saline (PBS) and permeabilized by a 30 minute incubation with saponin (0.5 mg/ml). The detergent was removed with three washes of PBS, and a blocking solution of 5% normal rabbit serum was added for 30 minutes. The primary antibody was added at a dilution of 1:3 in 1% normal rabbit serum, subsequent to the removal of the blocking solution, and the cultures were incubated overnight at 4° C. The solution containing the primary antibody was removed with a PBS wash. The bound immunoglobulin was detected by the Vectastain "ABC" method. Diaminobenzidene tetrahydrochloride (DAB) was used as the substrate for the peroxidase reaction which was usually carried out for one to five minutes. The reaction was stopped by rinsing the cultures two times with 0.1M tris-HCl pH 7.2. The cultures were stored in 50 mM tris, pH 7.6 containing 0.15M NaCl, 42% glycerol, and 0.15% Zephiran (Pierce Chemical Co., Rockville, Ill.) at 4° C.

12.1.6. Method of Generating Purified Astroglial Cell Cultures

Purified glial cultures were prepared essentially by the method of McCarthy and DeVellis (McCarthy, K. D., and DeVellis, J., 1980, *J. Cell Biol.* 85:890-902) from postnatal day 1-2 rat hippocampus. Hippocampi were removed from five pups and minced with scissors. The tissue pieces were then digested in 2 mls of 0.125% trypsin for 20 minutes at 37° C. The protease was inactivated by dilution, with plating medium (10% fetal bovine serum Gibco, DMEM, 0.5% penicillin (5000 mcg/ml) and 0.5% glutamine). A single cell suspension was produced by passing the digested tissue fragments through a constricted pasteur pipette. The cells were pelleted by centrifugation at 900 rpm for five minutes, resuspended in plating medium, and then counted on a hemocytometer. The single cell suspension was divided into three, 75 cm$^2$ tissue culture flask and the cells were grown to approximately 80% of confluency. The cells were then subcultured by a trypsinization protocol similar to that just described. The glial were counted and plated at a density of 10,000 cells/0.9 cm$^2$.

12.2. Results

12.2.1. The Effect of BDNF on Tyrosine Hydroxylase Present in Ventral Mesencephalon Cultures Immunocytochemical staining, as described in section 12.1.2, supra, was used to measure the effect of BDNF on the number of tyrosine hydroxylane (TH) positive cells (FIG. 8). A maximal increase of more than 200 percent of control was observed by day 8 in BDNF stimulated cultures of ventral mesencephalon cells. A very slight increase was observed as early as culture day 3 in BDNF-stimulated cultures.

12.2.2. The Effect of BDNF on Dopamine Uptake Uptake by Ventral Mesencephalon Cultures $^3$H-dopamine ($^3$H-DA) uptake was measured according to the method of Dal Taso et al. (1988, *J. Neurosci.* 8:733-745) with minor modifications, as described in section 12.1.3, supra. A slight increase in dopamine uptake was observed in BDNF stimulated ventral mesencephalon cultures by day 8 in culture (FIG. 9).

12.2.3. The Effect of BDNF on Choline Acetyltransferase Expression by Forebrain Cholinergic Neurons FIG. 10(A) depicts the effect of BDNF on the number of CAT positive cells following a growth period of 12 days in vitro. A 5.9 fold increase in CAT cell number was observed with the addition of 100 ng/ml of BDNF, while the EC50 was calculated to be 10 ng/ml. As a positive control, cultures at 260,000 (Black bar) or 150,000 (hatched bar) cells per well were treated in an identical manner with NGF (FIG. 10(B)). The 260,000 cell per well density corresponds to that used for the BDNF study. This increase in the number of CAT immunopositive cells is similar to that which has been reported previously. The potential for BDNF to act on cholinergic neurons was also examined by measuring CAT enzyme activity (F. Fonnum; J. Neurochemistry, 1975, 24:407–409). FIG. 11 depicts the changes in CAT produced with a BDNF treatment. In this case, a 1.8 fold increase was achieved with 100 ng/ml of BDNF and the EC50 was calculated to be 61 ng/ml.

12.2.4. Effects of BDNF or EGF on Astroglial Cell Cultures

Type II astrocytes have been demonstrated to have high affinity receptors for a variety of neurotransmitters and neuropeptides. Thus astrocytes are capable of responding to neuronally derived signals. For this reason and because the type II astrocytes represent a cellular component in the primary cultures, a possible direct effect of BDNF on glial cells was tested. The cells were kept in vitro for four days prior to the addition of growth factors to allow them to reach approximately 60% of confluency and were then treated for 42 hours with EGF or BDNF. For the last 18 hours of the incubation [$^3$H]methylthymidine was present in the medium. The effect of EGF is shown in FIG. 12(A). As has been previously reported, EGF was found to be mitogenic for the astrocytes. The maximal response was observed with 10 ng/ml of EGF which produced at 5.2-fold increase in [$^3$H]methylthymidine incorporation. FIG. 12(B) depicts the effect of BDNF on [$^3$H]methylthymidine incorporation. The response to BDNF appears to be biphasic: very low doses (0.1 ng/ml) produced a slight increase in thymidine incorporation; while doses greater than 1 ng/ml BDNF inhibited the incorporation of [$^2$H]methylthymidine. BDNF at a dosage of 5 ng/ml produced an inhibition of 24% suggesting a decrease in the rate of glial cell proliferation over the treatment period.

12.3. Discussion

These in vitro experiments clearly show that BDNF sustains the survival or induces the fully differentiated state of dopaminergic neurons of the developing rat substantia nigra, as shown by staining for tyrosine hydroxylase and dopamine uptake in cultures of these neurons derived from embryonic rat mesencephalon. As these are the neurons which degenerate in Parkinson's disease, it is highly probable that BDNF has therapeutic potential in Parkinson' disease either by reducing loss of neurons or by increasing the levels of tyrosine hydroxylase (the rate limiting enzyme in dopamine synthesis) or possibly both.

Furthermore, like nerve growth (NGF), BDNF appears to have an effect on the survival of cholinergic neurons of the rat basal forebrain as shown by increased choline acetyltransferase (CAT) staining, increased CAT activity and increased acetylcholinesterase staining in cultures of rat embryo medial septal nucleus and nucleus of the diagonal band of Broca. Accordingly, BDNF alone or in conjunction with NGF may be useful in the treatment of diseases or disorders that affect the cholinergic neurons of the basal forebrain, including, for example, Alzheimer's disease.

13. Example: Identification of a Novel Gene in the BDNF/NGF Gene Family

The approach of identifying novel members of the NGF/BDNF gene family by utilizing PCR with degenerate oligonucleotides, based on the segments of amino acid sequence conservation between NGF and BDNF (Boxes 1–4, see section 5.8), was first tested by determining whether pairs of such primers could be utilized to amplify both NGF and BDNF gene sequences from genomic DNA of several species. This method was then used to identify a novel gene which shares homology with NGF and BDNF in all four boxes of homology noted.

13.1. Materials and Methods

13.1.1. Polymerase Chain Reaction

PCR was performed essentially as described in Section 6, supra.

13.2. Results

13.2.1. Amplification of both NGF and BDNF Sequences from Genomic DNA

Degenerate synthetic oligonucleotide primers were synthesized corresponding to portions of Box 1 and Box 2 of amino acid sequence conservation between NGF and BDNF (see section 5.8 above), and utilized in a PCR reaction with rat genomic DNA as template. The exact primer sequences were as follows (positions of degeneracy, with mixture of two or more bases included in oligonucleotide synthesis step, shown in parentheses; underlining italics indicate tails with multiple restriction endonuclease cleavage sites provided to facilitate ligation to vector in a subsequent cloning step; A=adenine, G=guanine, C=cytosine, T=thymine, N=mixture of A,G,C,T):

Box 1 (sense), primer 1B:
5'-<u>GACTCGAGTCGACTCGG</u>TGTG(C,T)GACAG(C,T)(A,G)T(C,T,A)AG-3'

Box 2 (antisense), primer 2C:
5'-<u>CCAAGCTTCTAGAATTCC</u>A(C,T)TT(N)GT(C,T)TC(A,G)(A,T)A(A,G)AA(A,G),TA(C,T)TG-3'

300 ng of each degenerate primer mixture was added to 500 ng of rat genomic DNA in 100 microliters of the standard reaction mixture for PCR. 35 cycles were carried out, each consisting of incubation for 1 minute at 94° C., 2 minutes at 43° C., and 2 minutes at 72° C. The anticipated size of the product of PCR amplification of either the BDNF or NGF gene using these primers would be 175 base pairs, including the two 17-mer "tails" (underlined) included for convenience in subsequent cloning steps. Electrophoresis of the reaction mixture on an 8% polyacrylamide/5% glycerol gel yielded a major band of amplified DNA of the anticipated size, 175 bp.

13.2.2. Detection of Sequences Complementary to the BDNF/NGF Probe in Genomic DNAS of Various Species The 175 bp band was removed from the acrylamide gel by electroelution, and amplified further in a second PCR reaction of seven cycles, under identical reaction conditions to the first except that the concentrations of DGtp, dATP, and TTP were lowered to 50 μM each, and alpha-$^{32}$P-dCTP tracer was utilized in place of unlabeled dCTP. The radiolabeled DNA product was separated from reaction components by chromatography on a sizing column. This probe, designated "R1B/2C" (for rat DNA amplified from primers 1B and 2C), was then utilized to detect complementary sequences in genomic DNAs of various vertebrate species (results with rat, mouse, and chicken are shown in FIG. 13), after digestion with EcoRI restriction endonuclease and blotting to nitrocellulose by the method of Southern hybridization on EcoRI-digested genomic DNAs, as shown in FIG. 13.

The sizes of the EcoRI fragments of genomic DNA containing NGF and BDNF sequences were determined in controls on parallel blots using radiolabeled human NGF and BDNF probes, prepared by PCR from cloned genes. The positions of the NGF and BDNF genomic EcoRI fragments are indicated in FIG. 13 as N and B, respectively. The results of a similar analysis were presented in FIG. 3, and equivalent results were obtained using a human BDNF probe as with the porcine BDNF probe shown in FIG. 3. As noted above, NGF and BDNF probes each hybridized to single EcoRI fragments in a variety of vertebrate genomic DNAs. For example in rat DNA the BDNF probe detected a band of approximately 8.8 kb, while the NGF probe detected a band of approximately 10.4 kb.

As seen in FIG. 13, in every species tested (data shown for chicken, mouse and rat) the R1B/2C probe hybridized to a DNA band indistinguishable from that identified by the NGF probe as well as to a band indistinguishable from that identified by the BDNF probe (in mouse, the NGF and BDNF genomic EcoRI fragments have the same electrophoretic mobility, corresponding to approximately 11.5–12.0 kb). This demonstrates that the degenerate oligonucleotide primers 1B and 2C can be utilized to amplify sequences from both the NGF and BDNF genes. It was noteworthy that in some cases additional bands were observed in the genomic Southern blot hybridized with the R1B/2C probe. For example, in EcoRI-digested mouse genomic DNA at least two additional bands (labeled X1 and X2, of approximately 19.0 kb and 1.5 kb, respectively), corresponding to neither NGF nor BDNF, of were observed. Similarly, at least two additional bands were observed in hybridization to rat DNA (X1, X2, of approximately 7.3 and 1.2 kb, respectively), and at least one in chicken DNA (X, approximately 2.6 kb). Additional bands, not labeled explicitly in this figure, were also observed in some cases. The presence of bands not attributable to NGF or BDNF suggested the possible existence of additional member(s) of the gene family. Similarly, bands clearly distinct from those known to contain the BDNf and NGF gene sequences were found utilizing other sets of primer pairs and genomic DNA templates (data not shown).

13.2.3. Identification of a Novel Gene Related to BDNF and NGF

A specific test of the hypothesis that novel genes related to NGF and BDNF could be identified by PCR using degenerate oligonucleotide primers was carried out using primers for Box 3 and Box 4 (see section 5.8 above), and mouse genomic DNA as template. Degenerate primers were synthesized of the sequences:

Box 3 (sense):
5'-GGGGATCCGCGGITG(T,C)(C,A)GIGGIAT(T,C,A)GA-3'

Box 4 (anti-sense):
5'-TCGAATTCTAGATIC(T,G)IAT(AG)AAIC(T,G)LCCA-3'

(G=guanine, A=adenine, C-cytosine, T=thymine, I=inosine; mixtures of more than one base at a single position in the oligonucleotide shown in parentheses). Note that inosine was utilized at some positions corresponding to the third ("wobble") base of a codon, to allow for the degeneracy of the genetic code. It is also possible to utilize a mixture of the four conventional DNA bases rather than inosine, and essentially identical results have been obtained with such primers.

With the degenerate Box 3/Box 4 primer pair, PCR from the genomic NGF and BDNF sequences in mouse DNA would be expected to amplify a segment of approximately 90 bp. Utilizing the primers shown above, PCR was carried out for four cycles with an annealing temperature of 45° C., followed by 31 cycles with an annealing temperature of 49° C. The products were analyzed by gel electrophoresis, and a major band of the expected size was observed. In the mouse the NGF gene contains a HindII restriction endonuclease cleavage site in the region between Box 3 and Box 4, while the BDNF gene contains a site of cleavage for the enzyme Apal in this region. Therefore, digestion of the product of PCR amplification with HindII and Apal would be expected to eliminate NGF and BDNF sequences from the major product band. however, when the PCR product was digested to apparent completion with these two restriction enzymes, a digestion-resistant band was found to persist in the amplified DNA. This suggests that, in addition to NGF and BDNF genes, at least one novel gene had been amplified.

13.2.4. Characterization of a Novel Member of The BDNF/NGF Gene Family

The digestion-resistant PCR product was eluted from a gel, and utilized as template in asymmetric PCR reactions in which either one of the original degenerate primers was present in 100-fold molar excess over the other primer. This asymmetric amplification permitted the production of single-stranded DNA templates suitable for sequencing by the chain termination method. The sequence analysis of the novel gene (designated here as "M3/4") was extended further by PCR amplification of sequences between an exact primer located between Boxes 3 and 4 and the polyA sequence at the 3' end of the gene's transcript, using the strategy for "rapid amplification of cDNA ends" (RACE) described by M. A. Frohman, M. K. Dush, and G. R. Martin, Proc. Natl. Acad. Sci. USA, 85:8998–9002 (1988). The results of DNA sequencing revealed that a novel gene had been amplified, comprising an open reading frame capable of encoding a polypeptide distinct from both NGF and BDNF but closely related in amino acid sequence to both (FIG. 14).

Preliminary evidence that this new gene encodes a neurotrophic factor was obtained by determining its pattern of expression in rat tissues by northern blot hybridization. This analysis indicated that the novel gene is expressed much more strongly in brain tissue than in any other tissue examined.

13.3. Discussion

As shown above (FIG. 13), the DNA probe obtained by PCR amplification using primers for Boxes 1 and 2 with rat genomic DNA as template (R1B/2C) hybridized to novel bands in addition to those known to contain NGF and BDNF gene sequences in EcoRI-digested DNA of every species tested. A similar analysis was carried out using a radioactively labeled probe for the novel gene amplified using Box 3 and 4 primers on mouse genomic DNA (M3/4). In each case, the M3/4 probe hybridized to a single major band of EcoRI-digested genomic DNA, that was distinct from the bands known to contain BDNF and NGF sequences. It should e noted that the EcoRI fragments of genomic mouse, rat, and chicken DNA observed by hybridization with the M3/4 probe are in every case coincident with one of the novel bands obtained by hybridization with the R1B/2C probe. These are the 19.0 kb EcoRI fragment in mouse DNA (XI in FIG. 14), the 7.3 kb fragment in rat DNA (X1 in FIG. 14), and the 2.6 kb band in chicken DNA (X in FIG. 14). This suggests that portions of the same gene were amplified from rat DNA using the 1B/2C primer pair, and from mouse DNA using the ¾ primer pair. Thus, at least one novel gene apparently shares homology with NGF and BDNF genes in all four of the boxes of homology noted above.

The concept of the homology boxes between NGF, BDNF, and additional members of the gene family (e.g. "M3/4") has been expressed here primarily in terms of primary amino acid sequence, and methods for the identification of novel genes in the family. However, it is important to note that there are likely to be additional implications for the secondary and tertiary structure of these neurotrophic factors, their interactions with specific receptors, and rational design of novel molecules with potential therapeutic value.

For example, there are 6 Cys residues in NGF, and all have been shown to be involved in disulfide bonds. Numbering them from most N-terminal to most C-terminal as Cys1-Cys6, it is known that the disulfide bridges involve Cys1-Cys4, Cys2-Cys5, Cys3-Cys6. The positions of all 6 Cys residues are conserved between NGF and BDNF, and the positions of 3 Cys residues in the portion of "M3/4" sequenced to date line up exactly with Cys4, Cys5, Cys6, of NGF and BDNF. This suggests that the secondary structure of all members of the gene family may be closely related, and largely determined by the conserved Cys residues. It should be noted that the homology boxes pointed out for BDNF and NGF cover 5 of the 6 Cys residues (Cys1 in Box 1, Cys2 in Box 2, Cys3 and Box 3, Cys5 and Cys6 in Box 4). This supports the idea that these Cys residues and their immediate neighbors play an important role in determining the general structure of these neurotrophic factors. The structural determinants for specific interaction with high affinity receptors for each of the neurotrophic factors presumably reside in unique portions of each molecule.

Accordingly, novel chimeric genes may be produced by recombination between family members (e.g. by in vitro recombination, or by direct gene synthesis) at any of the four homology boxes already described, or elsewhere in the molecule. Such chimeric proteins are likely to have similar secondary structure, because of conservation of Cys residues, and other amino acid residues, but may have novel biological properties. For example, a BDNF/NGF chimeric protein may be bifunctional in terms of interaction with both BDNF and NGF receptors. Chimeric proteins may also differ from parent molecule(s) in terms of dimerization, and other physico-chemical properties. Chimeric proteins might also be able to function as antagonists of either parent molecule.

Active fragments of BDNF/NGF may be used to design other family members based on knowledge of critical "core" regions for appropriate folding, plus information regarding which regions are required for type-specific interaction with receptors.

Comparison of new family members (e.g. "M3/4") with already known family members may be used to reveal new boxes of homology that can help guide the search for additional members of the BDNF/NGF gene family. For example, "M3/4" comparison with BDNF reveals some useful homology boxes. One of particular interest involves the fourth conserved Cys residue, the only one not in the previously noted Boxes 1-4. There is actually a rather long segment of identity or conserved amino acid substitution shared by BDNF and "M3/4", which includes this Cys residue, namely: His-Trp-Asn-Ser-Gln-Cys-(Arg or Lys)-Thr(Thr or Ser)-Gln-(Ser or Thr)-Tyr-Val-Arg-Ala-Leu-Thr. Within this region one could choose at least two homology boxes for the synthesis of useful degenerate oligonucleotide primers (e.g. His-Trp-Asn-Ser-Gln-Cys requires only 96-fold degeneracy for an 18-mer primer, or 48-fold degeneracy for a 17-mer; Tyr-Val-Arg-Ala-Leu-Thr would also be a useful box).

14. EXAMPLE: INCREASED EXPRESSION OF BDNF IN NEUROBLASTOMA CELLS

14.1. Materials and Methods

14.1.1. Cell Lines

CHP100, CHP126, CHP134, CHP234, LAN1, LAN5, NB9, SY5Y, Y79, FO1, BU2, HO1, HL60, and COL320 are cell lines maintained in the laboratory of Dr. Fred Alt, who provided RNA for the Northern blot used in FIG. 15. All cell lines were human tumor cell lines. CHP100 is a neuroepithelioma cell line; CHP126, CHP134, CHP234, LAN1, LAN5, NB9, and SY5Y are neuroblastoma cell lines; Y79 is a retinoblastoma cell line; FO1, BU2, HO1 are melanoma cell lines, HL60 is a promyelocytic leukemia cell line, COL320 is a neuroendocrine colon carcinoma cell line.

14.1.2. Preparation of RNA

RNA was prepared and Northern blots performed essentially as described in Section 8.1.1, supra, using a full-length human cDNA probe. 10 μg of total RNA was in each lane of the gel used to produce the Northern blot of FIG. 15, except that the RNA in LAN1 was less heavily loaded and for SY5Y one microgram of poly(A)+ RNA was used.

14.2. Results and Discussion

FIG. 15 depicts the results of Northern blot analysis of BDNF probe hybridized to a panel of RNA samples obtained from a variety of human cell lines. An abundance of RNA which hybridized to BDNF probe was detected in CHP234 and LAN5 cell lines, and lower amounts were found in CHP126 and CHP134. All of the positive lines were derived from human neuroblastoma tumors.

15. DEPOSIT OF MICROORGANISMS

The following recombinant bacteriophage and recombinant plasmid DNA were deposited on Aug. 30, 1989 with the American Type Culture Collection in Rockville, Md.:

|  | ATCC Accession No. |
| --- | --- |
| phBDNF-C-1 | 40648 |
| λhBDNF-G-1 | 40649 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A purified nucleic acid that comprises a sequence that encodes a mature human brain derived neurotrophic factor protein having an amino acid sequence as follows:

His Ser Asp Pro Ala
Arg Arg Gly Glu Leu Ser Val Cys Asp Ser Ile Ser Glu Trp Val
Thr Ala Ala Asp Lys Lys Thr Ala Val Asp Met Ser Gly Gly Thr
Val Thr Val Leu Glu Lys Val Pro Val Ser Lys Gly Gln Leu Lys
Gln Tyr Phe Tyr Glu Thr Lys Cys Asn Pro Met Gly Tyr Thr
Lys Glu Gly Cys Arg Gly Ile Asp Lys Arg His Trp Asn Ser Gln
Cys Arg Thr Thr Gln Ser Tyr Val Arg Ala Leu Thr Met Asp
Ser Lys Lys Arg Ile Gly Trp Arg Phe Ile Arg Ile Asp Thr Ser
Cys Val Cys Thr Leu Thr Ile Lys Arg Gly Arg.

* * * * *